(12) United States Patent
Stupp et al.

(10) Patent No.: US 7,390,526 B2
(45) Date of Patent: Jun. 24, 2008

(54) METHODS AND MATERIALS FOR NANOCRYSTALLINE SURFACE COATINGS AND ATTACHMENT OF PEPTIDE AMPHIPHILE NANOFIBERS THEREON

(75) Inventors: Samuel I. Stupp, Chicago, IL (US); Erik D. Spoerke, Albuquerque, NM (US); Shawn G. Anthony, New Stanton, PA (US); Krista L. Niece, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 10/777,030

(22) Filed: Feb. 11, 2004

(65) Prior Publication Data

US 2004/0258726 A1 Dec. 23, 2004

Related U.S. Application Data

(60) Provisional application No. 60/495,965, filed on Aug. 18, 2003, provisional application No. 60/446,421, filed on Feb. 11, 2003.

(51) Int. Cl.
*A61K 27/32* (2006.01)

(52) U.S. Cl. .................. 427/2.27; 427/2.26; 514/2; 514/17; 514/18

(58) Field of Classification Search .............. 427/2.26, 427/2.27; 514/2, 17–18
See application file for complete search history.

(56) References Cited

U.S. PATENT DOCUMENTS

| | | | |
|---|---|---|---|
| 4,554,101 A | 11/1985 | Hopp | |
| 4,930,077 A | 5/1990 | Fan | |
| 5,130,123 A | 7/1992 | Reynolds et al. | |
| 5,208,111 A | 5/1993 | Decher et al. | |
| 5,670,483 A | 9/1997 | Zhang et al. | |
| 5,733,868 A | 3/1998 | Peterson et al. | |
| 5,843,780 A | 12/1998 | Thomson | |
| 5,871,767 A | 2/1999 | Dionne et al. | |
| 5,955,343 A | 9/1999 | Holmes et al. | |
| 5,993,541 A | 11/1999 | Litvin et al. | |
| 6,051,272 A | 4/2000 | Stupp et al. | |
| 6,085,206 A | 7/2000 | Domini et al. | |
| 6,096,863 A | 8/2000 | Fields et al. | |
| 6,156,321 A | 12/2000 | Thorpe et al. | |
| 6,181,909 B1 | 1/2001 | Burstein et al. | |
| 6,201,065 B1 | 3/2001 | Pathak et al. | |
| 6,265,539 B1 | 7/2001 | Arlinghaus | |
| 6,269,368 B1 | 7/2001 | Diamond | |
| 6,270,765 B1 | 8/2001 | Deo et al. | |
| 6,391,297 B1 | 5/2002 | Halvorsen | |
| 6,458,924 B2 | 10/2002 | Knudsen et al. | |
| 6,473,730 B1 | 10/2002 | McKeown et al. | |
| 6,548,048 B1 | 4/2003 | Cuthbertson et al. | |
| 6,548,630 B1 | 4/2003 | Zhang et al. | |
| 6,562,619 B1 | 5/2003 | Gearhart et al. | |
| 6,800,481 B1 | 10/2004 | Holmes et al. | |
| 6,855,329 B1 | 2/2005 | Shakesheff et al. | |
| 6,890,654 B2 | 5/2005 | Stupp et al. | |
| 2002/0007217 A1 | 1/2002 | Jacob et al. | |
| 2002/0046018 A1 | 4/2002 | Marcu et al. | |
| 2002/0142277 A1 | 10/2002 | Burstein et al. | |
| 2002/0160471 A1 | 10/2002 | Kisiday et al. | |
| 2003/0059906 A1 | 3/2003 | Hubbell et al. | |
| 2003/0092672 A1 | 5/2003 | Darcy et al. | |
| 2003/0176335 A1 | 9/2003 | Zhang et al. | |
| 2004/0001893 A1* | 1/2004 | Stupp et al. | 424/488 |
| 2004/0018961 A1* | 1/2004 | Stupp et al. | 514/7 |
| 2004/0022718 A1 | 2/2004 | Stupp et al. | |
| 2004/0258726 A1 | 12/2004 | Stupp et al. | |
| 2005/0208589 A1 | 9/2005 | Stupp et al. | |
| 2005/0209145 A1 | 9/2005 | Stupp et al. | |
| 2005/0214257 A1 | 9/2005 | Zhao et al. | |
| 2005/0272662 A1 | 12/2005 | Stupp et al. | |
| 2006/0149036 A1 | 7/2006 | Stupp et al. | |
| 2006/0247165 A1* | 11/2006 | Stupp et al. | 214/12 |

FOREIGN PATENT DOCUMENTS

| | | |
|---|---|---|
| WO | 97/14713 A1 | 4/1997 |
| WO | 97/20639 A1 | 6/1997 |
| WO | WO 98/07752 A1 | 2/1998 |
| WO | 99/36107 A1 | 7/1999 |
| WO | 00/13710 A2 | 3/2000 |
| WO | 00/44808 A1 | 8/2000 |
| WO | 00/52145 A2 | 9/2000 |
| WO | 00/64481 A1 | 11/2000 |
| WO | 01/00650 A1 | 1/2001 |
| WO | 02/062969 A2 | 8/2002 |
| WO | 03/040336 A2 | 5/2003 |
| WO | 03/054146 A2 | 7/2003 |
| WO | 03/070749 A2 | 8/2003 |
| WO | 03/084980 A2 | 10/2003 |
| WO | 03/090255 A2 | 10/2003 |
| WO | 2004/003561 A1 | 1/2004 |

(Continued)

OTHER PUBLICATIONS

Gergely (Key Engineering Materials 240-242 (Bioceramics) 287-290, 2003).*
English Abstract of Shimizu (JP 03099096, issued Apr. 1991).*
Nomizu, Motoyoshi, Atsushi Utani, Norio Shiraishi, Maura C. Kibbey, Yoshihiko Yamada, and Peter P. Roller. Jul. 15, 1992. "The All-D-Configuration Segment Containing the IKVAV Sequence of Laminin A Chain Has Similar Activities to the All-L-Peptide in Vitro and in Vivo." The Journal of Biological Chemistry. vol. 267, No. 20, pp. 14118-14121.

(Continued)

*Primary Examiner*—David Lukton

(57) ABSTRACT

Biocompatible composites comprising peptide amphiphiles and surface modified substrates and related methods for attachment thereon.

7 Claims, 12 Drawing Sheets

FOREIGN PATENT DOCUMENTS

| WO | 2004/018628 A2 | 3/2004 |
|---|---|---|
| WO | 2004/024778 A2 | 3/2004 |
| WO | 2004/046167 A2 | 6/2004 |
| WO | 2004/072104 A2 | 8/2004 |
| WO | 2004/106359 A2 | 12/2004 |
| WO | 2005/003292 A2 | 1/2005 |
| WO | 2005/056039 A1 | 6/2005 |
| WO | 2005/056576 A2 | 6/2005 |
| WO | 2006/096614 A2 | 9/2006 |

OTHER PUBLICATIONS

Margomenou-Leonidopoutou, G. 1994. "Thermotropic Mesophases of Ionic Amphiphiles. II. Ionic Amphiphiles in Aqueous Media." Journal of Thermal Analysis. vol. 42, pp. 1041-1061.

Rappolt, Michael and Gert Rapp. 1996. "Structure of the Stable and Metastable Ripple Phase of Dipalmitoylphosphatidylcholine." Eur. Biophys. J. vol. 24, pp. 381-386.

Goveas, J. L. and S. T. Milner. 1997. "Dynamics of the Lamellar—Cylindrical Transition in Weakly Segregated Diblock Copolymer Melts." Macromolecules. vol. 30, No. 9, pp. 2605-2612.

Munson, John B. and Stephen B. McMahon. 1997. "Effects of GDNF on Axotomized Sensory and Motor Neurons in Adult Rats." European Journal of Neuroscience. vol. 9, pp. 1126-1129.

Fernandez, A., M. A. Alsina, I. Haro, R. Galantai, and F. Reig. 1998. "Synthesis and Physicochemical Characterization of Cyclic Laminin Related Peptides." Langmuir. vol. 14, No. 13, pp. 3625-3630.

Yagi, Nobuhiro, Yoshikatsu Ogawa, Masato Kodaka, Tomoko Okada, Takenori Tomohiro, Takeo Konakahara, and Hiroaki Okuno. 1999. "A Surface-Modified Functional Liposome Capable of Binding to Cell Membranes." Chem. Commun. pp. 1687-1688.

Luo, Yi and Glenn D. Prestwich. 2001. "Novel Biomaterials for Drug Delivery." Expert Opin. Ther. Patents. vol. 11, No. 9, pp. 1395-1410.

Marchi-Artzner, Valerie, Barbara Lorz, Ulrike Hellerer, Martin Kantlehner, Horst Kessler, and Erich Sackmann. 2001. "Selective Adhesion of Endothelial Cells to Artificial Membranes with a Synthetic RGD-Lipopeptide." Chem. Eur. J. vol. 7, No. 5, pp. 1095-1101.

Blight, Andrew R. Nov. 2002. "Miracles and Molecules—Progress in Spinal Cord Repair." Nature Neuroscience Supplement. vol. 5, pp. 1051-1054.

Rodger, Alison, Jascindra Rajendra, Rachel Marrington, Malin Ardhammar, Bengt Norden, Jonathan D. Hirst, Andrew T. B. Gilbert, Timothy R. Dafforn, David J. Halsall, Cheryl A. Woolhead, Colin Robinson, Teresa J. T. Pinheiro, Jurate Kazlauskaite, Mark Seymour, Niuvis Perez, and Michael J. Hannon. 2002. "Flow Oriented Linear Dichroism to Probe Protein Orientation in Membrane Environments." Phys. Chem. Chem. Phys. vol. 4, pp. 4051-4057.

Silva, G. A., K. L. Kehl, K. L. Niece, and S. I. Stupp. May 4, 2003. "Nanoengineered Peptide Amphiphile Network for Photoreceptor Replacement in Degenerative Retinal Disorders." Investigative Ophthalmology & Visual Science. Abstract No. 492 from Annual Meeting of the Association for Research in Vision and Opthalmology.

Brandenburg, Klaus, Frauke Wagner, Mareike Muller, Holger Heine, Jorg Andra, Michel H. J. Koch, Ulrich Zahringer, and Ulrich Seydel. 2003. "Physicochemical Characterization and Biological Activity of a Glycoglycerolipid from Mycoplasma fermentans." Eur. J. Biochem. vol. 270, pp. 3271-3279.

Czeisler, C., V. M. Tysseling-Mattiace, G. A. Silva, S. I. Stupp, and J. A. Kessler. 2003. "Behavoral Improvement and Increased Survival Rate after Treatment with a Self Assembling Gel in a Rat Model of Spinal Cord Injury." 2003 Abstract Viewer/Itinerary Planner. Program No. 245.22. Washington, DC: Society for Neuroscience. Printed Feb. 5, 2007. p. 1. http://sfn.scholarone.com/itin2003/main.html?new_page_id=126&abstract_id=1554.

Schmidt, Christine E. and Jennie Baier Leach. 2003. "Neural Tissue Engineering: Strategies for Repair and Regeneration." Annu. Rev. Biomed. Eng. vol. 5, pp. 293-347.

t' Hart, Bert A. and Sandra Amor. 2003. "The Use of Animal Models to Investigate the Pathogenesis of Neuroflammatory Disorders of the Central Nervous System." Current Opinion in Neurology. vol. 16, pp. 375-383.

Beniash, Elia, Jeffery D. Hartgerink, Hannah Storrie, John C. Stendahl, and Samuel I. Stupp. 2005. "Self-Assembling Peptide Amphiphile Nanofiber Matrices for Cell Entrapment." Acta Biomaterialia. vol. 1, pp. 387-397.

Hoke, Ahmet. Aug. 2006. "Mechanisms of Disease: What Factors Limit the Success of Peripheral Nerve Regeneration in Humans?" Nature Clinical Practice Neurology. vol. 2, No. 8, pp. 448-454.

Kokkoli, Efrosini, Anastasia Mardilovich, Alison Wedekind, Emilie L. Rexeisen, Ashish Garg, and Jennifer A. Craig. 2006. "Self-Assembly and Applications of Biomimetic and Bioactive Peptide-Amphiphiles." Soft Matter. vol. 2, pp. 1015-1024.

The LabRat.com. 2007, updated. Hank's Buffered Salt Solution (HBSS) Recipe. http://www.thelabrat.com/protocolsHanks.shtml. Printed Jan. 19, 2007, pp. 1-2.

Brown, Walter E. Dec. 15, 1962. "Octacalcium Phosphate and Hydroxyapatite." Nature. vol. 196, pp. 1048-1050.

Liang, W. Y. and A. D. Yoffe. Jan. 8, 1968. "Transmission Spectra of ZnO Single Crystals." *Physical Review Letters.* vol. 20, No. 2, pp. 59-62.

Greenfield, Norma and Gerald D. Fasman. Oct. 1969. "Computed Circular Dichroism Spectra for the Evaluation of Protein Conformation." *Biochemistry.* vol. 8, No. 10, pp. 4108-4116.

Hantke, Klaus and Volkmar Braun. 1973. "Covalent Binding of Lipid to Protein: Diglyceride and Amide-Linked Fatty Acid at the N-Terminal End of the Murein-Lipoprotein of the *Escherichia coli* Outer Membrane." *Eur. J. Biochem.* vol. 34, No. 2, pp. 284-296.

Balcerski, James S., E. S. Pysh, G. M. Bonora, and C. Toniolo. Jun. 9, 1976. "Vacuum Ultraviolet Circular Dichroism of β-Forming Alkyl Oligopeptides." *Journal of the American Chemical Society.* vol. 98, No. 12, pp. 3470-3473.

Jacobson, Bruce S. and Daniel Branton. Jan. 21, 1977. "Plasma Membrane: Rapid Isolation and Exposure of the Cytoplasmic Surface by Use of Positively Charged Beads." *Science.* vol. 195, No. 4275, pp. 302-304.

Biesecker, G., J. Ieuan Harris, J. C. Thierry, J. E. Walker, and A. J. Wonacott. Mar. 24, 1977. *Nature.* vol. 266, pp. 328-333.

Kelly, Margaret M., E. S. Pysh, G. M. Bonora, and C. Toniolo. May 11, 1977. "Vacuum Ultraviolet Circular Dichroism of Protected Homooligomers Derived from L-Leucine." *Journal of the American Chemical Society.* vol. 99, No. 10, pp. 3264-3266.

Blumenthal, N. C., A. S. Posner, L. D. Silverman, and L. C. Rosenberg. 1979. "Effect of Proteoglycans on in Vitro Hydroxyapatite Formation." *Calcified Tissue International.* vol. 27, No. 1, pp. 75-82.

Lim, Franklin and Anthony M. Sun. Nov. 21, 1980. "Microencapsulated Islets as Bioartificial Endocrine Pancreas." *Science.* vol. 210, No. 4472, pp. 908-910.

Jain, Rakesh K., Chhitar M. Gupta, and Nitya Anand. 1981. "Synthesis of Peptidylglycophospholipids, Novel Derivatives of Muramyl-Dipeptide." *Tetrahedron Letters.* vol. 22, No. 24, pp. 2317-2320.

Sarin, Virender K., Stephen B. H. Kent, James P. Tam, and R. B. Merrifield. 1981. "Quantitative Monitoring of Solid-Phase Peptide Synthesis by the Ninhydrin Reaction." *Analytical Biochemistry.* vol. 117, pp. 147-157.

Yannas, I. V., J. F. Burke, D. P. Orgill, E. M. Skrabut. Jan. 8, 1982. "Wound Tissue Can Utilize a Polymeric Template to Synthesize a Functional Extension of Skin." *Science.* vol. 215, No. 4529, pp. 174-176.

Montesano, R., L. Orci, and P. Vassalli. Nov., 1983. "In Vitro Rapid Organization of Endothelial Cells into Capillary-like Networks Is Promoted by Collagen Matrices." *The Journal of Cell Biology.* vol. 97, pp. 1648-1652.

Pierschbacher, Michael D. and Erkki Ruoslahti. May 3, 1984. "Cell Attachment Activity of Fibronectin Can Be Duplicated by Small Synthetic Fragments of the Molecule." *Nature.* vol. 309, pp. 30-33.

Landis, W. J. and J. R. Martin. Apr.-Jun. 1984. "X-Ray Photoelectron Spectroscopy Applied to Gold-Decorated Mineral Standards of Biological Interest." *J. Vac. Sci. Technol.* vol. A 2, No. 2, pp. 1108-1111.

Thompson, Nancy L., Adrienne A. Brian, and Harden M. McConnell. 1984. "Covalent Linkage of a Synthetic Peptide to a Fluorescent Phospholipid and Its Incorporation into Supported Phospholipid Monolayers." *Biochimica et Biophysica Acta.* vol. 772, pp. 10-19.

Yamada, Kimiho, Hirotaka Ihara, Toshio Ide, Takanori Fukumoto, and Chuichi Hirayama. 1984. "Formation of Helical Super Structure from Single-Walled Bilayers by Amphiphiles with Oligo-L-Glutamic Acid-Head Group." *Chemistry Letters.* No. 10, pp. 1713-1716.

Addadi, L. and S. Weiner. Jun. 15, 1985. "Interactions Between Acidic Proteins and Crystals: Stereochemical Requirements in Biomineralization." *Proceedings of the National Academy of Sciences of the United States of America.* vol. 82, No. 12, pp. 4110-4114.

"Public Health Service Policy on Humane Care and Use of Laboratory Animals." Sep. 1986. Office for Protection from Research Risks (OPRR), National Institutes of Health.

Weiner, Stephen and Wolfie Traub. Oct. 1986. "Organization of Hydroxyapatite Crystals Within Collagen Fibrils." *FEBS Letters.* vol. 206, No. 2, pp. 262-266.

Mann, Stephen, John P. Hannington, and R. J. P. Williams. Dec. 11, 1986. "Phospholipid Vesicles as a Model System for Biomineralization." *Nature.* vol. 324, pp. 565-567.

Krimm, Samuel and Jagdeesh Bandekar. 1986. "Vibrational Spectroscopy and Conformation of Peptides, Polypeptides, and Proteins." *Advances in Protein Chemistry.* vol. 38, pp. 181-364.

de Groot, K., R. Geesink, C. P. A. T. Klein, and P. Serekian. Dec. 1987. "Plasma Sprayed Coatings of Hydroxylapatite." *Journal of Biomedical Materials Research.* vol. 21, No. 12, pp. 1375-1381.

Bresnahan, J. C., M. S. Beattie, F. D. Todd III, and D. H. Noyes. 1987. "A Behavioral and Anatomical Analysis of Spinal Cord Injury Produced by a Feedback-Controlled Impaction Device." *Experimental Neurology.* vol. 95, pp. 548-570.

Moscatelli, David. 1987. "High and Low Affinity Binding Sites for Basic Fibroblast Growth Factor on Cultured Cells: Absence of a Role for Low Affinity Binding in the Stimulation of Plasminogen Activator Production by Bovine Capillary Endothelial Cells." *Journal of Cellular Physiology.* vol. 131, pp. 123-130.

Lambert, Joseph B., Herbert F. Shurvell, David A. Lightner, and R. Graham Cooks. 1987. "Group Frequencies: Infrared and Raman." *Introduction to Organic Spectroscopy.* New York: Macmillan Publishing Company. pp. 169-182.

Cook, Stephen D., Kevin A. Thomas, John F. Kay, and Michael Jarcho. Jul. 1988. "Hydroxyapatite-Coated Titanium for Orthopedic Implant Applications." *Clinical Orthopaedics and Related Research.* No. 232, pp. 225-243.

Saksela, Olli, David Moscatelli, Andreas Sommer, and Daniel B. Rifkin. Aug. 1988. "Endothelial Cell-Derived Heparan Sulfate Binds Basic Fibroblast Growth Factor and Protects It from Proteolytic Degradation." *The Journal of Cell Biology.* vol. 107, pp. 743-751.

Cardin, Alan D. and H. J. R. Weintraub. Jan./Feb. 1989. "Molecular Modeling of Protein-Glycosaminoglycan Interactions." *Arteriosclerosis.* vol. 9, No. 1, pp. 21-32.

Oonishi, H., M. Yamamoto, H. Ishimaru, E. Tsuji, S. Kuskitani, M. Aono, and Y. Ukon. Mar. 1989. "The Effect of Hydroxyapatite Coating on Bone Growth into Porous Titanium Alloy Implants." *The Journal of Bone and Joint Surgery.* vol. 71-B, No. 2, pp. 213-216.

Friedmann, Theodore. Jun. 16, 1989. "Progress Toward Human Gene Therapy." *Science.* vol. 244, No. 4910, pp. 1275-1281.

Traub, Wolfie, Talmon Arad, and Stephen Weiner. Dec. 15, 1989. "Three-Dimensional Ordered Distribution of Crystals in Turkey Tendon Collagen Fibers." *Proceedings of the National Academy of Sciences of the United States of America.* vol. 86, No. 24, pp. 9822-9826.

Knorr, Reinhard, Arnold Trzeciak, Willi Bannwarth, and Dieter Gillessen. 1989. "New Coupling Reagents in Peptide Chemistry." *Tetrahedron Letters.* vol. 30, No. 15, pp. 1927-1930.

Sambrook, Joseph, Edward F. Fritsch, and Thomas Maniatis. 1989. "Genes Encoding Selectable Markers." *Molecular Cloning: A Laboratory Manual.* 2$^{nd}$ ed. New York: Cold Spring Harbor Laboratory Press. pp. 16.9-16.15.

Veis, A. 1989. "Biochemical Studies of Vertebrate Tooth Mineralization." *Biomineralization.* S. Mann, J. Webb, and R. J. P. Williams, editors. Weinheim, Federal Republic of Germany: VCH Verlagsgesellschaft and New York: VCH Publishers. pp. 189-222.

Schnell, Lisa and Martin E. Schwab. Jan. 18, 1990. "Axonal Regeneration in the Rat Spinal Cord Produced by an Antibody Against Myelin-Associated Neurite Growth Inhibitors." *Nature.* vol. 343, pp. 269-272.

Ahn, Sang Tae and Thomas A. Mustoe. Jan. 1990. "Effects of Ischemia on Ulcer Wound Healing: A New Model in the Rabbit Ear." *Annals of Plastic Surgery.* vol. 24, No. 1, pp. 17-23.

Van de Pol, Frans C. M. Dec. 1990. "Thin-Film ZnO—Properties and Applications." *Ceramic Bulletin.* vol. 69, No. 12, pp. 1959-1965.

Addadi, L., A. Berman, J. Moradian-Oldak, and S. Weiner. Dec. 28, 1990. "Tuning of Crystal Nucleation and Growth by Proteins: Molecular Interactions at Solid-Liquid Interfaces in Biomineralization." *Croatica Chemica Acta.* vol. 63, No. 3, pp. 539-544.

Sukenik, Chaim N., Natarajan Balachander, Lloyd A. Culp, Kristine Lewandowska, and Katherine Marritt. 1990. "Modulation of Cell Adhesion by Modification of Titanium Surfaces with Covalently Attached Self-Assembled Monolayers." *Journal of Biomedical Materials Research.* vol. 24, pp. 1307-1323.

Fields, C. G., D. H. Lloyd, R. L. Macdonald, K. M. Otteson, and R. L. Noble. Mar./Apr. 1991. "HBTU Activation for Automated Fmoc Solid-Phase Peptide Synthesis." *Peptide Research.* vol. 4, No. 2, pp. 95-101.

Murata, Masayuki, Satoshi Kagiwada, Sho Takahashi, and Shun-ichi Ohnishi. Aug. 5, 1991. "Membrane Fusion Induced by Mutual Interaction of the Two Charge-Reversed Amphiphilic Peptides at Neutral pH." *The Journal of Biological Chemistry.* vol. 56, No. 22, pp. 14353-14358.

Harris, Robin, Editor. 1991. *Electron Microscopy in Biology: A Practical Approach.* New York: Oxford University Press.

Jackson, David Y., David S. King, Jean Chmielewski, Sunil Singh, and Peter G. Schultz. 1991. "General Approach to the Synthesis of Short α-Helical Peptides." *Journal of the American Chemical Society.* vol. 113, pp. 9391-9392.

Polverini, Peter J., Noel P. Bouck, and Farzan Rastinejad. 1991. "Assay and Purification of Naturally Occurring Inhibitor of Angiogenesis." *Methods in Enzymology.* vol. 198, pp. 440-450.

Weiner, Stephen and Wolfie Traub. Feb. 1992. "Bone Structure: From Ångstroms to Microns." *The FASEB Journal.* vol. 6, pp. 879-885.

Addadi, Lia and Stephen Weiner. 1992. "Control and Design Principles in Biological Mineralization." *Angew. Chem. Int. Ed. Engl.* vol. 31, pp. 153-169.

Beresford, J. N., J. H. Bennett, C. Devlin, P. S. Leboy, and M. E. Owen. 1992. "Evidence for an Inverse Relationship Between the Differentiation of Adipocytic and Osteogenic Cells in Rat Marrow Stromal Cell Cultures." *Journal of Cell Science.* vol. 102, pp. 341-351.

Cook, Stephen D., Kevin A. Thomas, Jeanette E. Dalton, Todd K. Volkman, Thomas S. Whitecloud III, and John F. Kay. 1992. "Hydroxylapatite Coating of Porous Implants Improves Bone Ingrowth and Interface Attachment Strength." *Journal of Biomedical Materials Research.* vol. 26, pp. 989-1001.

Geahlen, Robert L., G. Marc Loudon, Lisa A. Paige, and David Lloyd. 1992. "A General Method for Preparation of Peptides Biotinylated at the Carboxy Terminus." *Analytical Biochemistry.* vol. 202, pp. 68-70.

Ghadiri, M. Reza, Christopher Soares, and Chong Choi. 1992. "Design of an Artificial Four-Helix Bundle Metalloprotein via a Novel Ruthenium(II)-Assisted Self-Assembly Process." *Journal of the American Chemical Society.* vol. 114, No. 10, pp. 4000-4002.

Kunitake, Toyoki. 1992. "Synthetic Bilayer Membranes: Molecular Design, Self-Organization, and Application." *Angew. Chem. Int. Ed. Engl.* vol. 31, pp. 709-726.

Stupp, Samuel I. and Glenn W. Ciegler. 1992. "Organoapatites: Materials for Artificial Bone. I. Synthesis and Microstructure." *Journal of Biomedical Materials Research.* vol. 26, pp. 169-183.

Surewicz, Witold K., Henry H. Mantsch, and Dennis Chapman. Jan. 19, 1993. "Determination of Protein Secondary Structure by Fourier Transform Infrared Spectroscopy: A Critical Assessment." *Biochemistry.* vol. 32, No. 2, pp. 389-394.

Zhang, Shuguang, Todd Holmes, Curtis Lockshin, and Alexander Rich. Apr. 15, 1993. "Spontaneous Assembly of a Self-Complementary Oligopeptide to Form a Stable Macroscopic Membrane." *Proceedings of the National Academy of Sciences of the United States of America.* vol. 90, No. 8, pp. 3334-3338.

Langer, Robert and Joseph P. Vacanti. May 14, 1993. "Tissue Engineering." *Science.* vol. 260, No. 5110, pp. 920-926.

Mulligan, Richard C. May 14, 1993. "The Basic Science of Gene Therapy." *Science.* vol. 260, No. 5110, pp. 926-932.

Massas, R., S. Pitaru, and M. M. Weinreb. Jun. 1993. "The Effects of Titanium and Hydroxyapatite on Osteoblastic Expression and Proliferation in Rat Parietal Bone Cultures." *Journal of Dental Research.* vol. 72, No. 6, pp. 1005-1008.

Archibald, Douglas D. and Stephen Mann. Jul. 29, 1993. "Template Mineralization of Self-Assembled Anisotropic Lipid Microstructures." *Nature.* vol. 364, pp. 430-433.

Atala, Anthony, Linda G. Cima, Wooseob Kim, Keith T. Paige, Joseph P. Vacanti, Alan B. Retik, and Charles A. Vacanti. Aug. 1993. "Injectable Alginate Seeded with Chondrocytes as a Potential Treatment for Vesicoureteral Reflux." *The Journal of Urology.* vol. 150, No. 2, pp. 745-747.

Ross-Murphy, S. B. and K. P. Shatwell. May-Aug. 1993. "Polysaccharide Strong and Weak Gels." *Biorheology.* vol. 30, Nos. 3 & 4, pp. 217-227.

Margalit, Hanah, Nurit Fischer, and Shmuel A. Ben-Sasson. Sep. 15, 1993. "Comparative Analysis of Structurally Defined Heparin Binding Sequences Reveals a Distinct Spatial Distribution of Basic Residues." *The Journal of Biological Chemistry.* vol. 268, No. 26, pp. 19228-19231.

Fowler, Bruce O., Milenko Marković, and Walter E. Brown. 1993. "Octacalcium Phosphate. 3. Infrared and Raman Vibrational Spectra." *Chem. Mater.* vol. 5, No. 10, pp. 1417-1423.

Fuhrhop, Jürgen-Hinrich, Dragan Spiroski, and Christoph Boettcher. 1993. "Molecular Monolayer Rods and Tubules Made of α-(L-Lysine),ω-(Amino) Bolaamphiphiles." *Journal of the American Chemical Society.* vol. 115, No. 4, pp. 1600-1601.

Graham, Stephan and Paul W. Brown. 1993. "The Low Temperature Formation of Octacalcium Phosphate." *Journal of Crystal Growth.* vol. 132, pp. 215-225.

Shimizu, Toshimi and Masakatsu Hato. 1993. "Self-Assembling Properties of Synthetic Peptidic Lipids." *Biochimica et Biophysica Acta.* vol. 1147, pp. 50-58.

Stupp, Samuel I., Jacqueline A. Hanson, Jo Ann Eurell, Glenn W. Ciegler, and Ann Johnson. 1993. "Organoapatites: Materials for Artificial Bone. III. Biological Testing." *Journal of Biomedical Materials Research.* vol. 27, pp. 301-311.

Stupp, Samuel I., George C. Mejicano, and Jacqueline A. Hanson. 1993. "Organoapatites: Materials for Artificial Bone. II. Hardening Reactions and Properties." *Journal of Biomedical Materials Research.* vol. 27, pp. 289-299.

Wald, Heidi L., Georgios Sarakinos, Michelle D. Lyman, Antonios G. Mikos, Joseph P. Vacanti, and Robert Langer. 1993. "Cell Seeding in Porous Transplantation Devices." *Biomaterials.* vol. 14, No. 4, pp. 270-278.

Walsh, Dominic, Joanne L. Kingston, Brigid R. Heywood, and Stephen Mann. 1993. "Influence of Monosaccharides and Related Molecules on the Morphology of Hydroxyapatite." *Journal of Crystal Growth.* vol. 133, pp. 1-12.

Wang, B. C., T. M. Lee, E. Chang, and C. Y. Yang. 1993. "The Shear Strength and Failure Mode of Plasma-Sprayed Hydroxyapatite Coating to Bone: The Effect of Coating Thickness." *Journal of Biomedical Materials Research.* vol. 27, pp. 1315-1327.

San Antonio, James D., Arthur D. Lander, Morris J. Karnovsky, and Henry S. Slayter. Jun. 1994. "Mapping the Heparin-Binding Sites on Type I Collagen Monomers and Fibrils." *The Journal of Cell Biology.* vol. 125, No. 5, pp. 1179-1188.

Ban, S., S. Maruno, H. Iwata, and H. Itoh. 1994. "Calcium Phosphate Precipitation on the Surface of HA-G-Ti Composite Under Physiologic Conditions." *Journal of Biomedical Materials Research.* vol. 28, pp. 65-71.

de Bruijn, J. D., Y. P. Bovell, and C. A. van Blitterswijk. 1994. "Structural Arrangements at the Interface Between Plasma Sprayed Calcium Phosphates and Bone." *Biomaterials.* vol. 15, No. 7, pp. 543-550.

Hunter, Graeme K. and Harvey A. Goldberg. 1994. "Modulation of Crystal Formation by Bone Phosphoproteins: Role of Glutamic Acid-Rich Sequences in the Nucleation of Hydroxyapatite by Bone Sialoprotein." *Biochem. J.* vol. 302, pp. 175-179.

Klein, C. P. A. T., J. G. C. Wolke, J. M. A. de Blieck-Hogervorst, and K. de Groot. 1994. "Calcium Phosphate Plasma-Sprayed Coatings and Their Stability: An in Vivo Study." *Journal of Biomedical Materials Research.* vol. 28, pp. 909-917.

Mikos, Antonios G., Michelle D. Lyman, Lisa E. Freed, and Robert Langer. 1994. "Wetting of Poly(L-Lacid Acid) and Poly(DL-Lactic-co-glycolic Acid) Foams for Tissue Culture." *Biomaterials.* vol. 15, No. 1, pp. 55-58.

Bond, G. M., R. H. Richman, and W. P. McNaughton. Jun. 1995. "Mimicry of Natural Material Designs and Processes." *Journal of Materials Engineering and Performance.* vol. 4, No. 3, pp. 334-345.

Hubbell, Jeffrey A. Jun. 1995. "Biomaterials in Tissue Engineering." *Bio/technology.* vol. 13, pp. 565-576.

Fromm, J. R., R. E. Hileman, E. E. O. Caldwell, J. M. Weiler, and R. J. Linhardt. Nov. 10, 1995. "Differences in the Interaction of Heparin with Arginine and Lysine and the Importance of these Basic Amino Acids in the Binding of Heparin to Acidic Fibroblast Growth Factor." *Archives of Biochemistry and Biophysics.* vol. 323, No. 2, pp. 279-287.

Wakitani, Shigeyuki, Tomoyuki Saito, and Arnold I. Caplan. Dec. 1995. "Myogenic Cells Derived from Rat Bone Marrow Mesenchymal Stem Cells Exposed to 5-Azacytidine." *Muscle & Nerve.* vol. 18, pp. 1417-1426.

Aletras, Alexios, Kleomenis Barlos, Dimitrios Gatos, Sophia Koutsogianni, and Petros Mamos. 1995. "Preparation of the Very Acid-Sensitive Fmoc-Lys(Mtt)-OH." *International Journal of Peptide & Protein Research.* vol. 45, pp. 488-496.

Berndt, Peter, Gregg B. Fields and Matthew Tirrell. 1995. "Synthetic Lipidation of Peptides and Amino Acids: Monolayer Structure and Properties." *Journal of the American Chemical Society.* vol. 117, No. 37, pp. 9515-9522.

Gage, Fred H., Jasodhara Ray, and Lisa J. Fisher. 1995. "Isolation, Characterization, and Use of Stem Cells from the CNS." *Annual Review of Neuroscience.* vol. 18, pp. 159-192.

Nomizu, Motoyoshi, Benjamin S. Weeks, Christi A. Weston, Woo Hoo Kim, Hynda K. Kleiman, and Yoshihiko Yamada. 1995. "Structure-Activity Study of a Laminin α1 Chain Active Peptide Segment Ile-Lys-Val-Ala-Val (IKVAV)." *FEBS Letters.* vol. 365, pp. 227-231.

Saito, Tomoyuki, James E. Dennis, Donald P. Lennon, Randell G. Young, and Arnold I. Caplan. 1995. "Myogenic Expression of Mesenchymal Stem Cells Within Myotubes of *mdx* Mice in Vitro and in Vivo." *Tissue Engineering.* vol. 1, No. 4, pp. 327-343.

Sasanuma, Michio. 1995. "Optical Processes in ZnO." *J. Phys.: Condens. Matter.* vol. 7, pp. 10029-10036.

Zhang, Shuguang, Todd C. Holmes, C. Michael DiPersio, Richard O. Hynes, Xing Su, and Alexander Rich. 1995. "Self-Complementary Oligopeptide Matrices Support Mammalian Cell Attachment." *Biomaterials.* vol. 16, No. 18, pp. 1385-1393.

Falini, Guiseppe, Shira Albeck, Steve Weiner, and Lia Addadi. Jan. 5, 1996. "Control of Aragonite or Calcite Polymorphism by Mollusk Shell Macromolecules." *Science.* vol. 271, No. 5245, pp. 67-69.

Alivisatos, A. P. Feb. 16, 1996. "Semiconductor Clusters, Nanocrystals, and Quantum Dots." *Science.* vol. 271, No. 5251, pp. 933-937.

Keyt, Bruce A., Lea T. Berleau, Hung V. Nguyen, Helen Chen, Henry Heinsohn, Richard Vandlen, and Napoleone Ferrara. Mar. 29, 1996. "The Carboxyl-terminal Domain (111-165) of Vascular Endothelial Growth Factor Is Critical for Its Mitogenic Potency." *The Journal of Biological Chemistry.* vol. 271, No. 13, pp. 7788-7795.

Belcher, A. M., X. H. Wu, R. J. Christensen, P. K. Hansma, G. D. Stucky, and D. E. Morse. May 2, 1996. "Control of Crystal Phase Switching and Orientation by Soluble Mullusc-Shell Proteins." *Nature.* vol. 381, pp. 56-58.

Hortelano, Gonzalo, Ayman Al-Hendy, Frederick A. Ofosu, and Patricia L. Chang. Jun. 15, 1996. "Delivery of Human Factor IX in Mice by Encapsulated Recombinant Myoblasts: A Novel Approach Towards Allogenic Gene Therapy of Hemophilia B." *Blood.* vol. 87, No. 12, pp. 5095-5103.

Sultzbaugh, K. J. and T. J. Speaker. Jul.-Aug. 1996. "A Method to Attach Lectins to the Surface of Spermine Alginate Microcapsules Based on the Avidin Biotin Interaction." *J. Microencapsulation.* vol. 13, No. 4, pp. 363-375.

Alivisatos, A. Paul, Kai P. Johnsson, Xiaogang Peng, Troy E. Wilson, Colin J. Loweth, Marcel P. Burchez, Jr., and Peter G. Schultz. Aug. 15, 1996. "Organization of 'Nanocrystal Molecules' Using DNA." *Nature.* vol. 382, pp. 609-611.

George, Anne, Leslie Bannon, Boris Sabsay, Jerry W. Dillon, James Malone, Arthur Veis, Nancy A. Jenkins, Debra J. Gilbert, and Neal G. Copeland. Dec. 20, 1996. "The Carboxyl-terminal Domain of Phosphophoryn Contains Unique Extended Triplet Amino Acid Repeat Sequences Forming Ordered Carboxyl-Phosphate Interaction Ridges That May Be Essential in the Biomineralization Process." *The Journal of Biological Chemistry.* vol. 271, No. 51, pp. 32869-32873.

Basso, D. Michele, Michael S. Beattie, and Jacqueline C. Bresnahan. 1996. "Graded Histological and Locomotor Outcomes after Spinal Cord Contusion Using the NYU Weight-Drop Device Versus Transection." *Experimental Neurology.* vol. 139, pp. 244-256.

Burkett, Sandra L. and Stephen Mann. 1996. "Spatial Organization and Patterning of Gold Nanoparticles on Self-Assembled Biolipid Tubular Templates." *Chem. Commun.* pp. 321-322.

Hunter, Graeme K., Peter V. Hauschka, A. Robin Poole, Lawrence C. Rosenberg, and Harvey A. Goldberg. 1996. "Nucleation and Inhibition of Hydroxyapatite Formation by Mineralized Tissue Proteins." *Biochem. J.* vol. 317, pp. 59-64.

Karymov, Mikhail A., Karel Procházka, John M. Mendenhall, Thomas J. Martin, Petr Munk, and Stephen E. Webber. 1996. "Chemical Attachment of Polystyrene-*block*-poly(methacrylic acid) Micelles on a Silicon Nitride Surface." *Langmuir.* vol. 12, No. 20, 4748-4753.

Landis, William J., Karen J. Hodgens, James Arena, Min Ja Song, and Bruce F. McEwen. 1996. "Structural Relations Between Collagen and Mineral in Bone as Determined by High Voltage Electron Microscopic Tomography." *Microscopy Research and Technique.* vol. 33, pp. 192-202.

Matsuzawa, Mieko, Forrest F. Weight, Richard S. Potember, and Päivi Liesi. 1996. "Directional Neurite Outgrowth and Axonal Differentiation of Embryonic Hippocampal Neurons Are Promoted by a Neurite Outgrowth Domain of the B2-Chain of Laminin." *Int. J. Devl. Neuroscience.* vol. 14, No. 3, pp. 283-295.

Mooney, David J., Daniel F. Baldwin, Nam P. Suh, Joseph P. Vacanti, and Robert Langer. 1996. "Novel Approach to Fabricate Porous Sponges of Poly(D,L-Lactic-co-glycolic Acid) Without the Use of Organic Solvents." *Biomaterials.* vol. 17, No. 14, pp. 1417-1422.

Ratner, Buddy D., Allan S. Hoffman, Frederick J. Schoen, and Jack E. Lemons, Editors. 1996. *Biomaterials Science: An Introduction to Materials in Medicine.* San Diego, CA: Academic Press.

Ulman, Abraham. 1996. "Formation and Structure of Self-Assembled Monolayers." *Chemical Reviews.* vol. 96, No. 4, pp. 1533-1554.

Yu, Ying-Ching, Peter Berndt, Matthew Tirrell, and Gregg B. Fields. 1996. "Self-Assembling Amphiphiles for Construction of Protein Molecular Architecture." *Journal of the American Chemical Society.* vol. 118, No. 50, pp. 12515-12520.

Zarif, Leila, Ange Polidori, Bernard Pucci, Tadek Gulik-Krzywicki, AndréA. Pavia, and Jean G. Riess. 1996. "Effect of Chirality of the Formation of Tubules from Glycolipidic Amphiphiles." *Chemistry and Physics of Lipids.* vol. 79, pp. 165-170.

Aggeli, A., M. Bell, N. Boden, J. N. Keen, P. F. Knowles, T. C. B. McLeish, M. Pitkeathly, and S. E. Radford. Mar. 20, 1997. "Responsive Gels Formed by the Spontaneous Self-Assembly of Peptides into Polymeric β-Sheet Tapes." *Nature.* vol. 386, pp. 259-262.

Herr, Andrew B., David M. Ornitz, Ram Sasisekharan, Ganesh Venkataraman, and Gabriel Waksman. Jun. 27, 1997. "Heparin-Induced Self-Association of Fibroblast Growth Factor-2." *The Journal of Biological Chemistry.* vol. 272, No. 26, pp. 16382-16389.

Dimmeler, Stefanie and Andreas M. Zeiher. Aug. 1997. "Nitric Oxide and Apoptosis: Another Paradigm for the Double-Edged Role of Nitric Oxide." *Nitric Oxide: Biology and Chemistry.* vol. 1, No. 4, pp. 275-281.

Stupp, Samuel I. and Paul V. Braun. Aug. 29, 1997. "Molecular Manipulation of Microstructures: Biomaterials, Ceramics, and Semiconductors." *Science.* vol. 277, No. 5330, pp. 1242-1248.

Kaufmann, P. M., S. Heimrath, B. S. Kim, and D. J. Mooney. Sep./Oct. 1997. "Highly Porous Polymer Matrices as a Three-Dimenional Culture System for Hepatocytes." *Cell Transplantation.* vol. 6, No. 5, pp. 463-468.

Aggeli, Amalia, Mark Bell, Neville Boden, Jeff N. Keen, Tom C. B. McLeish, Irina Nyrkova, Sheena E. Radford, and Alexander Semenov. 1997. "Engineering of Peptide β-Sheet Nanotapes." *J. Mater. Chem.* vol. 7, No. 7, pp. 1135-1145.

Anderson, James M. Matthew S. Shive. 1997. "Biodegradation and Biocompatibility of PLA and PLGA Microspheres." *Advanced Drug Delivery Reviews.* vol. 28, pp. 5-24.

Draget, Kurt Ingar, Gudmund Skjåk-Bræk, Olav Smidsrød. 1997. "Alginate Based New Materials." *International Journal of Biological Macromolecules.* vol. 21, pp. 47-55.

El-Ghannam, Ahmed, Paul Ducheyne, and Irving M. Shapiro. 1997. "Porous Bioactive Glass and Hydroxyapatite Ceramic Affect Bone Cell Function In Vitro Along Different Time Lines." *Journal of Biomedical Materials Research.* vol. 36, pp. 167-180.

Jaiswal, Neelam, Stephen E. Haynesworth, Arnold I. Caplan, and Scott P. Bruder. 1997. "Osteogenic Differentiation of Purified, Culture-Expanded Human Mesenchylmal Stem Cells In Vitro." *Journal of Cellular Biochemistry.* vol. 64, pp. 295-312.

Nehrer, Stefan, Howard A. Breinan, Arun Ramappa, Sonya Shortkroff, Gretchen Young, Tom Minas, Clement B. Sledge, Ioannis V. Yannas, and Myron Spector. 1997. "Canine Chondrocytes Seeded in Type I and Type II Collagen Implants Investigated In Vitro." *Journal of Biomedical Materials Research (Appl. Biomater.).* vol. 38, pp. 95-104.

Mann, Stephen. 1997. "Biomineralization: The Form(id)able Part of Bioinorganic Chemistry!" *J. Chem. Soc., Daltron Trans.* pp. 3953-3961.

Norrby, Klas. 1997. "Angiogenesis: New Aspects Relating to Its Initiation and Control." *APMIS.* vol. 105, pp. 417-437.

Shimizu, Toshimi, Masaki Kogiso, and Mitsutoshi Masuda. 1997. "Noncovalent Formation of Polyglycine II-Type Structure by Hexagonal Self-Assembly of Linear Polymolecular Chains." *Journal of the Americal Chemical Society.* vol. 119, No. 26, pp. 6209-6210, S2-S17.

Smith, George P. and Valery A. Petrenko. 1997. "Phage Display." *Chemical Reviews.* vol. 97, No. 2, pp. 391-410.

Toyotama, Akiko, Shin-ichi Kugimiya, Masakatsu Yonese, Takatoshi Kinoshita, and Yoshiharu Tsujita. 1997. "Controllable Orientation of the Peptide-Based Surfactant at Air-Water Interface." *Chemistry Letters.* pp. 443-444.

Weiner, Stephen and Lia Addadi. 1997. "Design Strategies in Mineralized Biological Materials." *J. Mater. Chem.* vol. 7, No. 5, pp. 689-702.

Wellings, Donald A. and Eric Atherton. 1997. "Standard Fmoc Protocols." *Methods in Enzymology.* vol. 289, pp. 44-67.

Wen, H. B., J. G. C. Wolke, J. R. de Wijn, Q. Liu, F. Z. Cui, and K. de Groot. 1997. "Fast Precipitation of Calcium Phosphate Layers on Titanium Induced by Simple Chemical Treatments." *Biomaterials.* vol. 18, No. 22, pp. 1471-1478.

Yu, Ying-Ching, Teika Pakalns, Yoav Dori, James B. McCarthy, Matthew Tirrell, and Gregg B. Fields. 1997. "Construction of Biologically Active Protein Molecular Architecture Using Self-Assembling Peptide-Amphiphiles." *Methods in Enzymology.* vol. 289, pp. 571-587.

Zhitomirsky, I. and L. Gal-Or. 1997. "Electrophoretic Deposition of Hydroxyapatite." *Journal of Materials Science: Materials in Medicine.* pp. 213-219.

Veis, Arthur, Kuiru Wei, Charles Sfeir, Anne George, and James Malone. Jan. 1998. "Properties of the $(DSS)_n$ Triplet Repeat Domain of Rat Dentin Phosphophoryn." *European Journal of Oral Sciences.* vol. 106 (suppl. 1), pp. 234-238.

Pincus, David W., Robert R. Goodman, Richard A. R. Fraser, Maiken Nedergaard, and Steven A. Goldman. Apr. 1998. "Neural Stem and Progenitor Cells: A Strategy for Gene Therapy and Brain Repair." *Neurosurgery.* vol. 42, No. 4, pp. 858-867.

Ogiso, M., Y. Yamashita, and T. Matsumoto. Jun. 1998. "The Process of Physical Weakening and Dissolution of the HA-Coated Implant in Bone and Soft Tissue." *Journal of Dental Research.* vol. 77, No. 6, pp. 1426-1434.

Petka, Wendy A., James L. Harden, Kevin P. McGrath, Denis Wirtz, and David A. Tirrell. Jul. 17, 1998. "Reversible Hydrogels from Self-Assembling Artificial Proteins." *Science.* vol. 281, No. 5375, pp. 389-392.

Orgill, Dennis P., Charles Butler, John F. Regan, Mark S. Barlow, I. V. Yannas, and Carolyn C. Compton. Aug. 1998. "Vascularized Collagen-Glycosaminoglycan Matrix Provides a Dermal Substrate and Improves Take of Cultured Epithelial Autografts." *Plastic and Reconstructive Surgery.* vol. 102, No. 2, pp. 423-429.

Yu, Ying-Ching, Matthew Tirrell, and Gregg B. Fields. Oct. 7, 1998. "Minimal Lipidation Stabilizes Protein-Like Molecular Architecture." *Journal of the American Chemical Society.* vol. 120, No. 39, pp. 9979-9987.

Borkenhagen, M., J.-F. Clémence, H. Sigrist, and P. Aebischer. 1998. "Three-Dimensional Extracellular Matrix Engineering in the Nervous System." *Journal of Biomedical Materials Research.* vol. 40, pp. 392-400.

Brekke, John H. and Jeffrey M. Toth. 1998. "Principles of Tissue Engineering Applied to Programmable Osteogenesis." *Journal of Biomedical Materials Research (Appl. Biomater.).* vol. 43, pp. 380-398.

Fields, Gregg B., Janell L. Lauer, Yoav Dori, Pilar Forns, Ying-Ching Yu, and Matthew Tirrell. 1998. "Proteinlike Molecular Architecture: Biomaterial Applications for Inducing Cellular Receptor Binding and Signal Transduction." *Biopolymers (Peptide Science).* vol. 47, pp. 143-151.

Gu, Keni, Syweren R. Chang, Matt S. Slaven, Brian H. Clarkson, R. Bruce Rutherford, and Helena H. Ritchie. 1998. "Human Dentin Phosphophoryn Nucleotide and Amino Acid Sequence." *European Journal of Oral Sciences.* vol. 106, pp. 1043-1047.

Hartgerink, Jeffrey D., Thomas D. Clark, and M. Reza Ghadiri. 1998. "Peptide Nanotubes and Beyond." *Chem. Eur. J.* vol. 4, No. 8, pp. 1367-1372.

Johnstone, Brian, Thomas M. Hering, Arnold I. Caplan, Victor M. Goldberg, and Jung U. Yoo. 1998. "In Vitro Chondrogenesis of Bone Marrow-Derived Mesenchymal Progenitor Cells." *Experimental Cell Research.* vol. 238, pp. 265-272.

Kawasaki, M., A. Ohtomo, I. Ohkubo, H. Koinuma, Z. K. Tang, P. Yu, G. K. L. Wong, B. P. Zhang, and Y. Segawa. 1998. "Excitonic Ultraviolet Laser Emission at Room Temperature from Naturally Made Cavity in ZnO Nanocrytal Thin Films." *Materials Science and Engineering.* vol. B56, pp. 239-245.

Kogiso, Masaki, Satomi Ohnishi, Kiyoshi Yase, Mitsutoshi Masuda, and Toshimi Shimizu. 1998. "Dicarboxylic Oligopeptide Bolaamphiphiles: Proton-Triggererd Self-Assembly of Microtubes with Loose Solid Surfaces." *Langmuir.* vol. 14, No. 18, pp. 4978-4986, S1-S7.

Kogiso, Masaki, Takeshi Hanada, Kiyoshi Yase, and Toshimi Shimizu. 1998. "Intralayer Hydrogen-Bond-Directed Self-Assembly of Nano-Fibers from Dicarboxylic Valyvaline Bolaamphiphiles." *Chem. Comm.* pp. 1791-1792.

Li, Panjian and Paul Ducheyne. 1998. "Quasi-Biological Apatite Film Induced by Titanium in a Simulated Body Fluid." *Journal of Biomedical Materials Research.* vol. 41, pp. 341-348.

Nanci, A., J. D. Wuest, L. Peru, P. Brunet, V. Sharma, S. Zalzal, and M. D. McKee. 1998. "Chemical Modification of Titanium Surfaces for Covalent Attachment of Biological Molecules." *Journal of Biomedical Materials Research.* vol. 40, pp. 324-335.

Tsui, Y. C., C. Doyle, and T. W. Clyne. 1998. "Plasma Sprayed Hydroxyapatite Coatings on Titanium Substrates Part 2: Optimisation of Coating Properties." *Biomaterials.* vol. 19, pp. 2031-2043.

Weiner, S. and H. D. Wagner. 1998. "The Material Bone: Structure-Mechanical Function Relations." *Annu. Rev. Mater. Sci.* vol. 28, pp. 271-298.

Wen, H. B., J. R. de Wijn, F. Z. Cui, and K. de Groot. 1998. "Preparation of Calcium Phosphate Coatings on Titanium Implant Materials by Simple Chemistry." *Journal of Biomedical Materials Research.* vol. 41, pp. 227-236.

Wheeler, Donna L., David L. Chamberland, John M. Schmitt, David C. Buck, John H. Brekke, Jeffrey O. Hollinger, S.-P. Joh, and K.-W. Suh. 1998. "Radiomorphometry and Biomechanical Assessment of Recombinant Human Bone Morphogenetic Protein 2 and Polymer in Rabbit Radius Ostectomy Model." *Journal of Biomedical Materials Research (Appl. Biomater.).* vol. 43, pp. 365-373.

Wolke, J. G. C., K. de Groot, and J. A. Jansen. 1998. "In Vivo Dissolution of Various RF Magnetron Sputtered Ca-P Coatings." *Journal of Biomedical Materials Research.* vol. 39, pp. 524-530.

Xiao, Shou-Jun, Marcus Textor, and Nicholas D. Spencer. 1998. "Covalent Attachment of Cell-Adhesive, (Arg-Gly-Asp)-Containing Peptides to Titanium Surfaces." *Langmuir.* vol. 14, No. 19, pp. 5507-5516.

Xu, Guofeng, Nan Yao, Ilhan A. Aksay, and John T. Groves. 1998. "Biomimetic Synthesis of Macroscopic-Scale Calcium Carbonate Thin Films. Evidence for a Multistep Assembly Process." *Journal of the American Chemical Society.* vol. 120, No. 46, pp. 11977-11985.

Yamada, Norihiro, Katsuhiko Ariga, Masanobu Naito, Kazuhiro Matsubara, and Emiko Koyama. 1998. "Regulation of β-Sheet Structures Within Amyloid-Like β-Sheet Assemblage from Tripeptide Derivatives." *Journal of the American Chemical Society.* vol. 120, No. 47, pp. 12192-12199.

Chusuei, Charles C., D. Wayne Goodman, Michael J. Van Stipdonk, Dina R. Justes, and Emile A. Schweikert. Jan. 1, 1999. "Calcium Phosphate Phase Identification Using XPS and Time-of-Flight Cluster SMS." *Analytical Chemistry.* vol. 71, No. 1, pp. 149-153.

Zubarev, Eugene R. Martin U. Pralle, Leiming Li, and Samuel I. Stupp. Jan. 22, 1999. "Conversion of Supramolecular Clusters to Macromolecular Objects." *Science.* vol. 283, pp. 523-526.

Won, You-Yeon, H. Ted Davis, and Frank S. Bates. Feb. 12, 1999. "Giant Wormlike Rubber Micelles." *Science.* vol. 283, No. 5404, pp. 960-963.

Corral, Claudio, J. Aamir Siddiqui, Liancun Wu, Catherine L. Farrell, David Lyons, and Thomas A. Mustoe. Feb. 1999. "Vascular Endothelial Growth Factor Is More Important Than Basic Fibroblastic Growth During Ischemic Wound Healing." *Arch. Surg.* vol. 134, pp. 200-205.

Wheeler, B. C., J. M. Corey, G. J. Brewer, and D. W. Branch. Feb. 1999. "Microcontact Printing for Precise Control of Nerve Cell Growth in Culture." *Journal of Biomechanical Engineering.* vol. 121, pp. 73-78.

Cao, H., Y. G. Zhao, S. T. Ho, E. W. Seelig, Q. H. Wang, and R. P. H. Chang. Mar. 15, 1999. "Random Laser Action in Semiconductor Powder." *Physical Review Letters.* vol. 82, No. 11, pp. 2278-2281.

Aizenberg, Joanna, Andrew J. Black, and George M. Whitesides. Apr. 8, 1999. "Control of Crystal Nucleation by Patterned Self-Assembled Monolayers." *Nature.* vol. 398, pp. 495-498.

Niklason, L. E., J. Gao, W. M. Abbott, K. K. Hirschi, S. Houser, R. Marini, and R. Langer. Apr. 16, 1999. "Functional Arteries Grown in Vitro." *Science.* vol. 284, pp. 489-493.

Hahn, Jungseok and Stephen E. Webber. Apr. 1999. "Modification of Surfaces by Covalent Attachment of Polymer Micelles." *Macromolecular Symposia.* vol. 139, pp. 39-47.

Liu, Yi, Duckhyun Kim, B. Timothy Himes, Stella Y. Chow, Timothy Schallert, Marion Murray, Alan Tessler, and Itzhak Fischer. Jun. 1, 1999. "Transplants of Fibroblasts Genetically Modified to Express BDNF Promote Regeneration of Adult Rat Rubrospinal Axons and Recovery of Forelimb Function." *The Journal of Neuroscience.* vol. 19, No. 11, pp. 4370-4387.

Mehler, Mark F. and John A. Kessler. Jul. 1999. "Progenitor Cell Biology: Implications for Neural Regeneration." *Arch. Neurol.* vol. 56, pp. 780-784.

Tirrell, M. Oct. 27, 1999. "Biofunctionalization of Surfaces with Peptide Amphiphiles." *AVS: Science & Technology.* Invited Paper BI-WeM7.

McDonald, John W., Xiao-Zhong Liu, Yun Qu, Su Liu, Shannon K. Mickey, Dorothy Turetsky, David I. Gottlieb, and Dennis W. Choi. Dec. 1999. "Transplanted Embryonic Stem Cells Survive, Differentiate and Promote Recovery in Injured Rat Spinal Cord." *Nature Medicine.* vol. 5, No. 12, pp. 1410-1412.

Bradt, Jens-Hilmar, Michael Mertig, Angelika Teresiak, and Wolfgang Pompe. 1999. "Biomimetic Mineralization of Collagen by Combined Fibril Assembly and Calcium Phosphate Formation." *Chem. Mater.* vol. 11, No. 10, pp. 2694-2701.

Braun, Paul V. and Samuel I. Stupp. 1999. "CdS Mineralization of Hexagonal, Lamellar, and Cubic Lyotropic Liquid Crystals." *Materials Research Bulletin.* vol. 34, No. 3, pp. 463-469.

Butler, C. E., I. V. Yannas, C. C. Compton, C. A. Correia, and D. P. Orgill. 1999. "Comparison of Cultured and Uncultured Keratinocytes Seeded into a Collagen-GAG Matrix for Skin Replacements." *British Journal of Plastic Surgery.* vol. 52, pp. 127-132.

Chai, C. S. and B. Ben-Nissan. 1999. "Bioactive Nanocrystalline Sol-Gel Hydroxyapatite Coatings." *Journal of Materials Science: Materials in Medicine.* vol. 10, pp. 465-469.

Clark, Thomas D., Kenji Kobayashi, and M. Reza Ghadiri. 1999. "Covalent Capture and Stabilization of Cylindrical β-Sheet Peptide Assemblies." *Chem. Eur. J.* vol. 5, No. 2, pp. 782-792.

Cornish, J., K. E. Callon, C. Q.-X. Lin, C. L. Xiao, T. B. Mulvey, G. J. S. Cooper, and I. R. Reid. 1999. "Trifluoroacetate, a Contaminant in Purified Proteins, Inhibits Proliferation of Ostoeblasts and Chondrocytes." *Am. J. Physiol. Endocrinol. Metab.* vol. 277, pp. 779-783.

Emoto, Kazunori, Yukio Nagasaki, and Kazunori Kataoka. 1999. "Coating of Surfaces with Stabilized Reactive Micelles from Poly-(ethylene glycol)—Poly(DL-Lactic Acid) Block Copolymer." *Langmuir.* vol. 15, No. 16, pp. 5212-5218.

Fields, Gregg B. 1999. "Induction of Protein-like Molecular Architecture by Self-Assembly Processes." *Bioorganic & Medicinal Chemistry.* vol. 7, pp. 75-81.

Haynes, Andrew J., Wei-Qun Huang, Jamie Mallah, Dajun Yang, Marc E. Lippman, and Lu-Yuan Li. 1999. "Angiopoietin-1 and Its Receptor Tie-2 Participate in the Regulation of Capillary-like Tubule Formation and Survival of Endothelial Cells." *Microvascular Research.* vol. 58, pp. 224-237.

Hwang, Julia J., Kevin Jaeger, James Hancock, and Samuel I. Stupp. 1999. "Organoapatite Growth on an Orthopedic Alloy Surface." *Journal of Biomedical Materials Research.* vol. 47, pp. 504-515.

Ignjatović, Nenad, Simonida Tomić, Momčilo Dakić, Miroslav Miljković, Milenko Plavšić, and Dragan Uskoković. 1999. "Synthesis and Properties of Hydroxyapatite/Poly-L-Lactide Composite Biomaterials." *Biomaterials.* vol. 20, pp. 809-816.

Lee, Kevin J. and Thomas M. Jessell. 1999. "The Specification of Dorsal Cell Fates in the Vertebrate Central Nervous System." *Annual Review of Neuroscience.* vol. 22, pp. 261-294.

Lee, Kyujin C., Paul A. Carlson, Alex S. Goldstein, Paul Yager, and Michael H. Gelb. 1999. "Protection of a Decapeptide from Proteolytic Cleavage by Lipidation and Self-Assembly into High-Axial-Ratio Microstructures: A Kinetic and Structural Study." *Langmuir.* vol. 15, No. 17, pp. 5500-5508.

Mao, Chuanbin, Hengde Li, Fuzhai Cui, Chunlai Ma, and Qinglin Feng. 1999. "Oriented Growth of Phosphates on Polycrystalline Titanium in a Process Mimicking Biomineralization." *Journal of Crystal Growth.* vol. 206, pp. 308-321.

Miyaji, Fumiaki, Hyun-Min Kim, Shinichi Handa, Tadashi Kokubo, and Takashi Nakamura. 1999. "Bonelike Apatite Coating on Organic Polymers: Novel Nucleation Process Using Sodium Silicate Solution." *Biomaterials.* vol. 20, pp. 913-919.

Pakalns, Teika, Kraig L. Haverstick, Gregg B. Fields, James B. McCarthy, Daniel L. Mooradian, and Matthew Tirrell. 1999. "Cellular Recognition of Synthetic Peptide Amphiphiles in Self-Assembled Monolayer Films." *Biomaterials.* vol. 20, pp. 2265-2279.

Pittenger, Mark F., Alastair M. Mackay, Stephen C. Beck, Rama K. Jaiswal, Robin Douglas, Joseph D. Mosca, Mark A. Moorman, Donald W. Simonetti, Stewart Craig, and Daniel R. Marshak. Apr. 2, 1999. "Multilineage Potential of Adult Human Mesenchymal Stem Cells." *Science.* vol. 284, pp. 143-147.

Rezania, Alireza, Robert Johnson, Anthony R. Lefkow, and Kevin E. Healy. 1999. "Bioactivation of Metal Oxide Surfaces. 1. Surface Characterization and Cell Response." *Langmuir.* vol. 15, No. 20, pp. 6931-6939.

Rowley, Jon A., Gerard Madlambayan, and David J. Mooney. 1999. "Alginate Hydrogels as Synthetic Extracellular Matrix Materials." *Biomaterials.* vol. 20, pp. 45-53.

Schense, Jason C. and Jeffrey A. Hubbell. 1999. "Cross-Linking Exogenous Bifunctional Peptides into Fibrin Gels with Factor XIIIa." *Bioconjugate Chem.* vol. 10, No. 1, pp. 75-81.

Varma, H. K., Y. Yokogawa, F. F. Espinosa, Y. Kawamoto, K. Nishizawa, F. Nagata, and T. Kameyama. 1999. "In-Vitro Calcium Phosphate Growth over Functionalized Cotton Fibers." *Journal of Materials Science: Materials in Medicine.* vol. 10, pp. 395-400.

Vernon, Robert B. and E. Helene Sage. 1999. "A Novel, Quantitative Model for Study of Endothelial Cell Migration and Sprout Formation Within Three-Dimensional Collagen Matrices." *Microvascular Research.* vol. 57, pp. 188-133.

Wei, M., A. J. Ruys, M. V. Swain, S. H. Kim, B. K. Milthorpe, and C. C. Sorrell. 1999. "Interfacial Bond Strength of Electrophoretically Deposited Hydroxyapatite Coatings on Metals." *Journal of Materials Science: Materials in Medicine.* vol. 10, pp. 401-409.

Yu, Ying-Ching, Vikram Roontga, Vladimir A. Daragan, Kevin H. Mayo, Matthew Tirrell, and Gregg B. Fields. 1999. "Structure and Dynamics of Peptide—Amphiphiles Incorporating Triple-Helical Proteinlike Molecular Architecture." *Biochemistry.* vol. 38, No. 5, pp. 1659-1668.

Huq, N. Laila, Keith J. Cross, and Eric C. Reynolds. Feb. 4, 2000. "Molecular Modelling of a Multiphosphorylated Sequence Motif Bound to Hydroxyapatite Surfaces." *Journal of Molecular Modeling.* vol. 6, pp. 35-47.

Martinez, J. S., G. P. Zhang, P. D. Holt, H. -T. Jung. C. J. Carrano, M. G. Haygood, and Alison Butler. Feb. 18, 2000. "Self-Assembling Amphiphilic Siderophores from Marine Bacteria." *Science.* vol. 287, No. 5456, pp. 1245-1247.

Verrecchio, Angela, Markus W. Germann, Barbara P. Schick, Brian Kung, Thomas Twardowski, and James D. San Antonio. Mar. 17, 2000. "Design of Peptides with High Affinities for Heparin and Endothelial Cell Proteoglycans." *The Journal of Biological Chemistry.* vol. 275, No. 11, pp. 7701-7707.

Cao, H., J. Y. Xu, E. W. Seelig, and R. P. H. Chang. May 22, 2000. "Microlaser Made of Disordered Media." *Applied Physics Letters.* vol. 76, No. 21, pp. 2997-2999.

Marler, Jennifer J., Amrita Guha, Jonathan Rowley, Rahul Koka, David Mooney, Joseph Upton, and Joseph Vacanti. May 2000. "Soft-Tissue Augmentation with Injectable Alginate and Syngeneic Fibroblasts." *Plastic and Reconstructive Surgery.* vol. 105, No. 6, pp. 2049-2058.

Holmes, Todd C., Sonsoles de Lacalle, Xing Su, Guosong Liu, Alexander Rich, and Shuguang Zhang. Jun. 6, 2000. "Extensive Neurite Outgrowth and Active Synapse Formation on Self-Assembling Peptide Scaffolds." *Proceedings of the National Academy of Sciences of the United States of America.* vol. 97, No. 12, pp. 6728-6733.

Whaley, Sandra R., D. S. English, Evelyn L. Hu, Paul F. Barbara, and Angela M. Belcher. Jun. 8, 2000. "Selection of Peptides with Semiconductor Binding Specificity for Directed Nanocrystal Assembly." *Nature.* vol. 405, pp. 665-668.

Sun, Xiu-xia and Chi-chen Wang. Jul. 28, 2000. "The N-Terminal Sequence (Residues 1-65) Is Essential for Dimerization, Activities, and Peptide Binding of *Escherichia coli* DsbC." *The Journal of Biological Chemistry.* vol. 275, No. 30, pp. 22743-22749.

Hsu, Wei-Cherng, Mark H. Spilker, Ioannis V. Yannas, and Peter A. D. Rubin. Aug. 2000. "Inhibition of Coonjunctival Scarring and Contraction by a Porous Collagen-Glycosaminoglycan Implant." *Investigative Ophthalmology & Visual Science.* vol. 41, pp. 2404-2411.

Schlessinger, Joseph, Alexander N. Plotnikov, Omar A. Ibrahimi, Anna V. Eliseenkova, Brian K. Yeh, Avner Yayon, Robert J. Linhardt, and Moosa Mohammadi. Sep. 2000. "Crystal Structure of a Ternary FGF-FGFR-Heparin Complex Reveals a Dual Role for Heparin in FGFR Binding and Dimerization." *Molecular Cell.* vol. 6, pp. 743-750.

Sun, Y., J. B. Ketterson, and G. K. L. Wong. Oct. 9, 2000. "Excitonic Gain and Stimulated Ultraviolet Emission in Nanocrystalline Zinc-Oxide Powder." *Applied Physics Letters.* vol. 77, No. 15, pp. 2322-2324.

Schuldiner, Maya, Ofra Yanuka, Joseph Itskovitz-Eldor, Douglas A. Melton, and Nissim Benvenisty. Oct. 10, 2000. "Effects of Eight Growth Factors on the Differentiation of Cells Derived from Human Embryonic Stem Cells." *Proceedings of the National Academy of Sciences of the United States of America.* vol. 97, No. 21, pp. 11307-11312.

Altman, Michael, Peter Lee, Alexander Rich, and Shuguang Zhang. 2000. "Conformational Behavior of Ionic Self-Complementary Peptides." *Protein Science.* vol. 9, pp. 1095-1105.

Archer, Eric A., Noah T. Goldberg, Vincent Lynch, and Michael J. Krische. 2000. "Nanostructured Polymer Duplexes via the Covalent Casting of 1-Dimensional H-Bonding Motifs: A New Strategy for the Self-Assembly of Macromolecular Precursors." *Journal of the American Chemical Society.* vol. 122, No. 20, pp. 5006-5007.

Ariga, Katsuhiko, Jun-ichi, Masanobu Naito, Emiko Koyama, and Norihiro Yamada. 2000. "Modulated Supramolecular Assemblies Composed of Tripeptide Derivatives: Formation of Micrometer-Scale Rods, Nanometer-Size Needles, and Regular Patterns with Molecular-Level Flatness from the Same Compound." *Langmiur.* vol. 16, No. 11, pp. 4929-4939.

Beniash, E., W. Traub, A. Veis, and S. Weiner. 2000. "A Transmission Electron Microscope Study Using Vitrified Ice Sections of Predentin: Structural Changes in the Dentin Collagenous Matrix Prior to Mineralization." *Journal of Structural Biology.* vol. 122, pp. 212-225.

Bigi, Adriana, Elisa Boanini, Silvia Panzavolta, and Norberto Roveri. 2000. "Biomimetic Growth of Hydroxyapatite on Gelatin Films Doped with Sodium Polyacrylate." *Biomacromolecules.* vol. 1, No. 4, pp. 752-756.

Bourel, Line, Oliver Carion, Hélène Gras-Masse, and Oleg Melnyk. 2000. "The Deprotection of Lys(Mtt) Revisited." *Journal of Peptide Science.* vol. 6, pp. 264-270.

Caplan, Michael R., Peter N. Moore, Shuguang Zhang, Roger D. Kamm, and Douglas A. Lauffenburger. 2000. "Self-Assembly of a β-Sheet Protein Governed by Relief of Electrostatic Repulsion Relative to van der Waals Attraction." *Biomacromolecules.* vol. 1, No. 4, pp. 627-631.

Cardullo, F., M. Crego Calama, B. H. M. Snellink-Ruël, J.-L. Weidmann, A. Bielejewska, R. Fokkens, N. M. M. Nibbering, P. Timmerman, and D. N. Reinhoudt. 2000. "Covalent Capture of Dynamic Hydrogen-Bonded Assemblies." *Chem. Commun.* pp. 367-368.

Chamberlain, L. J., I. V. Yannas, H-P. Hsu, G. R. Strichartz, and M. Spector. 2000. "Near-Terminus Axonal Structure and Function Following Rat Sciatic Nerve Regeneration Through a Collagen-GAG Matrix in a Ten-Millimeter Gap." *Journal of Neuroscience Research.* vol. 60, pp. 666-677.

David, Sunil A., Satish K. Awasthi, and P. Balaram. 2000. "The Role of Polar and Facial Amphipathic Character in Determining Lipopolysaccharide-Binding Properties in Synthetic Cationic Peptides." *Journal of Endotoxin Research.* vol. 6, No. 3, pp. 249-256.

Dori, Yoav, Havazelet Bianco-Peled, Sushil K. Satija, Gregg B. Fields, James B. McCarthy, and Matthew Tirrell. 2000. "Ligand Accessibility as Means to Control Cell Response to Bioactive Bilayer Membranes." *Journal of Biomedical Materials Research.* vol. 50, pp. 75-81.

Forns, Pilar, Janelle L. Lauer-Fields, Su Gao, and Gregg B. Fields. 2000. "Induction of Protein-Like Molecular Architecture by Monoalkyl Hydrocarbon Chains." *Biopolymers.* vol. 54, pp. 531-546.

Hisaeda, Yoshio, Eiji Ohshima, and Makiko Arimura. 2000. "Aggregation Behavior of Synthetic Peptide Lipids with Arginine in Aqueous Solution and Construction of a Vitamin $B_{12}$ Artificial Enzyme." *Colloids and Surfaces A: Physicochemical and Engineering Aspects.* vol. 169, pp. 143-153.

Kogiso, Masaki, Yuji Okada, Takeshi Hanada, Kiyoshi Yase, and Toshimi Shimizu. 2000. "Self-Assembled Peptide Fibers from Valylvaline Bola-Amphiphiles by a Parallel β-Sheet Network." *Biochimica et Biophysica Acta.* vol. 1475, pp. 346-352.

Langer, Robert. 2000. "Biomaterials in Drug Delivery and Tissue Engineering: One Laboratory's Experience." *Accounts of Chemical Research.* vol. 33, No. 2, pp. 94-101.

Liu, X. D., M. Skold, T. Umino, Y. K. Zhu, D. J. Romberger, J. R. Spurzem, and S. I. Rennard. 2000. "Endothelial Cell-Mediated Type I Collagen Gel Contraction Is Regulated by Hemin." *J. Lab. Clin. Med.* vol. 136, No. 2, pp. 100-109.

Lu, Lichun, Susan J. Peter, Michelle D. Lyman, Hui-Lin Lai, Susan M. Leite, Janet A. Tamada, Shiro Uyama, Joseph P. Vacanti, Robert Langer, and Antonios G. Mikos. 2000. "In Vitro and in Vivo Degradation of Porous Poly(DL-Lactic-*co*-Glycolic Acid) Foams." *Biomaterials.* vol. 21, pp. 1837-1845.

Matsuura, T., R. Hosokawa, K. Okamoto, T. Kimoto, and Y. Akagawa. 2000. "Diverse Mechanisms of Osteoblast Spreading on Hydroxyapatite and Titanium." *Biomaterials.* vol. 21, pp. 1121-1127.

Ponticiello, Michael S., Robert M. Schinagl, Sudha Kadiyala, and Frank P. Barry. 2000. "Gelatin-Based Resorbable Sponge as a Carrier Matrix for Human Mesenchymal Stem Cells in Cartilage Regeneration Therapy." *Journal of Biomedical Materials Research.* vol. 52, pp. 246-255.

Powell, Sharon K., Jayashree Rao, Eva Roque, Motoyoshi Nomizu, Yuichiro Kuratomi, Yoshihiko Yamada, and Hynda K. Kleinman. 2000. "Neural Cell Response to Multiple Novel Sites on Laminin-1." *Journal of Neuroscience Research.* vol. 61, pp. 302-312.

Sakiyama-Elbert, Shelly E. and Jeffrey A. Hubbell. 2000. "Controlled Release of Nerve Growth Factor from a Heparin-Containing Fibrin-Based Cell Ingrowth Matrix." *Journal of Controlled Release.* vol. 69, pp. 149-158.

Sakiyama-Elbert, Shelly E. and Jeffrey A. Hubbell. 2000. "Development of Fibrin Derivatives for Controlled Release of Heparin-Binding Growth Factors." *Journal of Controlled Release.* vol. 65, pp. 389-402.

Thareja, R. K. and A. Mitra. 2000. "Random Laser Action in ZnO." *Appl. Phys.* vol. B 71, pp. 181-184.

Tunggal, Patrick, Neil Smyth, Mats Paulsson, and Mark-Christoph Ott. 2000. "Laminins: Structure and Genetic Regulation." *Microscopy Research and Technique.* vol. 51, pp. 214-227.

do Serro, Ana Paula Valagão Amadeu, Anabela Catarino Fernandes, and Benilde de Jesus Vieira Saramago. 2000. "Calcium Phosphate Deposition on Titanium Surfaces in the Presence of Fibronectin." *Journal of Biomedical Materials Research.* vol. 49, pp. 345-352.

Yamada, Norihiro and Katsuhiko Ariga. 2000. "Formation of β-Sheet Assemblage with a View to Developing an Amyloid Model." *Synlett.* vol. 5, pp. 575-586.

Yang, Lin and Paschalis Alexandridis. 2000. "Physicochemical Aspects of Drug Delivery and Release from Polymer-Based Colloids." *Current Opinion in Colloid & Interface Science.* vol. 5, pp. 132-143.

Yu, Huanran, Hiroshi Narusawa, Kisae Itoh, Akihiro Oshi, Narutoshi Yoshino, Kazuo Ohbu, Toshiaki Shirakawa, Kazuhiro Fukada, Masatoshi Fujii, Tadashi Kato, and Tsutomu Seimiya. 2000. "Hydrophilicity of Polar and Apolar Domains of Amphiphiles." *Journal of Colloid and Interface Science.* vol. 229, pp. 375-390.

Zhu, G., M. F. Mehler, P. C. Mabie, and J. A. Kessler. 2000. "Developmental Changes in Neural Progenitor Cell Lineage Commitment Do Not Depend on Epidermal Growth Factor Receptor Signaling." *Journal of Neuroscience Research.* vol. 59, pp. 312-320.

Orlic, Donald, Jan Kajstura, Stefano Chimenti, Igor Jakonuk, Stacie M. Anderson, Baosheng Li, James Pickel, Ronald McKay, Bernardo Nadal-Ginard, David M. Bodine, Annarosa Leri, and Piero Anversa. Apr. 5, 2001. "Bone Marrow Cells Regenerate Infarcted Myocardium." *Nature.* vol. 410, pp. 701-705.

Vailhé, Bruno, Daniel Vittet, and Jean-Jacques Feige. Apr. 2001. "In Vitro Models of Vasculogenesis and Angiogenesis." *Laboratory Investigation.* vol. 81, No. 4, pp. 439-452.

Davis, N. G., J. Teisen, C. Shuh, and D. C. Dunand. May 2001. "Solid-State Foaming of Titanium by Superplastic Expansion of Argon-Filled Pores." *J. Mater. Res.* vol. 16, No. 5, pp. 1508-1519.

Rabchevksy, Alexander G. and George M. Smith. May 2001. "Therapeutic Interventions Following Mammalian Spinal Cord Injury." *Arch. Neurol.* vol. 58, pp. 721-726.

Huang, Michael H., Samuel Mao, Henning Feick, Haoquan Yan, Yiying Wu, Hannes Kind, Eicke Weber, Richard Russo, and Peidong Yang. Jun. 8, 2001. "Room-Temperature Ultraviolet Nanowire Nanolasers." *Science.* vol. 292, pp. 1897-1899.

Lee, Kuen Yong and David J. Mooney. Jul. 2001. "Hydrogels for Tissue Engineering." *Chemical Reviews.* vol. 101, No. 7, pp. 1869-1879.

Aggeli, A., I. A. Nyrkova, M. Bell, R. Harding, L. Carrick, T. C. B. McLeish, A. N. Semenov, and N. Boden. Oct. 9, 2001. "Hierarchical Self-Assembly of Chiral Rod-Like Molecules as a Model for Peptide β-Sheet Tapes, Ribbons, Fibrils, and Fibers." *Proceedings of the National Academy of Sciences of the United States of America.* vol. 98, No. 21, pp. 11857-11862.

Hartgerink, Jeffrey D., Elisa Beniash, and Samuel I. Stupp. Nov. 23, 2001. "Self-Assembly and Mineralization of Peptide-Amphiphile Nanofibers." *Science.* vol. 294, pp. 1684-1688.

Richardson, Thomas P., Martin C. Peters, Alessandra B. Ennett, and David J. Mooney. Nov. 2001. "Polymeric System for Dual Growth Factor Delivery." *Nature Biotechnology.* vol. 19, pp. 1029-1034.

Mathew, Mathai and Shozo Takagi. Nov.-Dec. 2001. "Structures of Biological Minerals in Dental Research." *Journal of Research of the National Institute of Standards and Technology.* vol. 106, No. 6, pp. 1035-1044.

Woo, Byung Ho, Betsy F. Fink, Richard Page, Jay A. Schrier, Yeong Woo Jo, Ge Jiang, Michelle DeLuca, Henry C. Vasconez, and Patrick P. DeLuca. Dec. 2001. "Enhancement of Bone Growth by Sustained Delivery of Recombinant Human Bone Morphogenetic Protein-2 in a Polymeric Matrix." *Pharmaceutical Research.* vol. 18, No. 12, pp. 1747-1753.

Barrère, F., P. Layrolle, C. A. Van Blitterswijk, and K. de Groot. 2001. "Biomimetic Coatings on Titanium: A Crystal Growth Study of Octacalcium Phosphate." *Journal of Materials Science: Materials in Medicine.* vol. 12, pp. 529-534.

Bianco-Peled, Havazelet, Yoav Dori, James Schneider, Li-Piin Sung, Sushil Satija, and Matthew Tirrell. 2001. "Structural Study of Langmuir Monolayers Containing Lipidated Poly(ethylene glycol) and Peptides." *Langmuir.* vol. 17, No. 22, pp. 6931-6937.

Cavalli, M., G. Gnappi, A. Montenero, D. Bersani, P. P. Lottici, S. Kaciulis, G. Mattogno, and M. Fini. 2001. "Hydroxy- and Fluorapatite Films on Ti Alloy Substrates: Sol-gel Preparation and Characterization." *Journal of Materials Science.* vol. 36, pp. 3253-3260.

Chang, John C., Gregory J. Brewer, and Bruce C. Wheeler. 2001. "Modulation of Neural Network Activity by Patterning." *Biosensors & Bioelectronics.* vol. 16, pp. 527-533.

Chang, Sophia C. N., Jon A. Rowley, Geoffrey Tobias, Nicholas G. Genes, Amit K. Roy, David J. Mooney, Charles A. Vacanti, and Lawrence J. Bonassar. 2001. "Injection Molding of Chondrocyte/Alginate Constructs in the Shape of Facial Implants." *Journal of Biomedical Materials Research.* vol. 55, pp. 503-511.

Doi, Tomokiyo, Takatoshi Kinoshita, Hiroki Kamiya, Shintaro Washizu, Yoshiharu Tsujita, and Hiraoki Yoshimizu. 2001. "Aggregation of Polypeptide-Based Amphiphiles in Water." *Polymer Journal.* vol. 33, No. 2, pp. 160-164.

Gore, Tushar, Yoav Dori, Yeshayahu Talmon, Matthew Tirrell, and Havazelet Bianco-Peled. 2001. "Self-Assembly of Model Collagen Peptide Amphiphiles." *Langmuir.* vol. 17, No. 17, pp. 5352-5360.

Hoess, Ronald H. 2001. "Protein Design and Phage Display." *Chemical Reviews.* vol. 101, No. 10, pp. 3205-3218.

Huang, Eric J. and Louis F. Reichardt. 2001. "Neurotrophins: Roles in Neuronal Development and Function." *Annual Review of Neuroscience.* vol. 24, pp. 677-736.

Kam, L., W. Shain, J. N. Turner, and R. Bizios. 2001. "Axonal Outgrowth of Hippocampal Neurons on Micro-Scale Networks of Polylysine-Conjugated Laminin." *Biomaterials.* vol. 22, pp. 1049-1054.

Kikuchi, Masanori, Soichiro Itoh, Shizuko Ichinose, Kenichi Shinomiya, and Junzo Tanaka. 2001. "Self-Organization Mechanism in a Bone-Like Hydroxyapatite/Collagen Nancomposite Synthesized in Vitro and Its Biological Reaction in Vivo." *Biomaterials.* vol. 22, pp. 1705-1711.

Liu, Yuelian, Pierre Layrolle, Joost de Bruijn, Clemens van Blitterswijk, and Klaas de Groot. 2001. "Biomimetic Coprecipitation of Calcium Phosphate and Bovine Serum Albumin on Titanium Alloy." *Journal of Biomedical Materials Research.* vol. 57, pp. 327-335.

Look, D. C. 2001. "Recent Advances in ZnO Materials and Devices." *Materials Science and Engineering.* vol. B80, pp. 383-387.

Matsui, Hiroshi, and Gary E. Douberly, Jr. 2001. "Organization of Peptide Nanotubes into Macroscopic Bundles." *Langmuir.* vol. 17, No. 25, pp. 7918-7922.

Neet, K. E. and R. B. Campenot. 2001. "Receptor Binding, Internalization, and Retrograde Transport of Neurotrophic Factors." *CMLS, Cell Mol. Life Sci.* vol. 58, pp. 1021-1035.

Otsuka, Hidenori, Yukio Nagasaki, and Kazunori Kataoka. 2001. "Self-Assembly of Poly(ethylene glycol) -based Block Copolymers for Biomedical Applications." *Current Opinion in Colloid & Interface Science.* vol. 6, pp. 3-10.

Shimizu, Toshimi, Rika Iwaura, Mitsutoshi Masuda, Takeshi Hanada, and Kiyoshi Yase. 2001. "Internucleobase-Interaction-Directed Self-Assembly of Nanofibers from Homo- and Heteroditopic $1,\omega$-Nucleobase Bolaamphiphiles." *Journal of the American Chemical Society.* vol. 123, No. 25, pp. 5947-5955, S1-S16.

Socrates, George. 2001. *Infrared and Raman Characteristic Group Frequencies: Tables and Charts.* Third Edition. Chichester, England: John Wiley & Sons Ltd.

Spanos, Nikos and Petros G. Koutsoukos. 2001. "Model Studies of the Effect of Orthophospho-L-Serine on Biological Mineralization." *Langmuir.* vol. 17, No. 3, pp. 866-872.

Takadama, Hiroaki, Hyun-Min Kim, Tadashi Kokubo, and Takashi Nakamura. 2001. "TEM-EDX Study of Mechanism of Bonelike Apatite Formation on Bioactive Titanium Metal in Simulated Body Fluid." *Journal of Biomedical Materials Research.* vol. 57, pp. 441-448.

Tanihara, Masao, Yasuo Suzuki, Eriko Yamamoto, Atsushi Noguchi, and Yutaka Mizushima. 2001. "Sustained Release of Basic Fibroblast Growth Factor and Angiogenesis in a Novel Covalently Crosslinked Gel of Heparin and Alginate." *Journal of Biomedical Materials Research.* vol. 56, pp. 216-221.

Torchilin, Vladimir P. 2001. "Structure and Design of Polymeric Surfactant-Based Drug Delivery Systems." *Journal of Controlled Release.* vol. 73, pp. 137-172.

Yeung, C. K., L. Lauer, A. Offenhäusser, and W. Knoll. 2001. "Modulation of the Growth and Guidance of Rat Brain Stem Neurons Using Patterned Extracellular Matrix Proteins." *Neuroscience Letters.* vol. 301, pp. 147-150.

Zubarev, Eugene R., Martin U. Pralle, Eli D. Sone, and Samuel I. Stupp. 2001. "Self-Assembly of Dendron Rodcoil Molecules into Nanoribbons." *Journal of the American Chemical Society.* vol. 123, No. 17, pp. 4105-4106.

Hirschi, Karen K., Lihua Lai, Narasimhaswamy S. Belaguli, David A. Dean, Robert J. Schwartz, and Warren E. Zimmer. Feb. 22, 2002. "Transforming Growth Factor-$\beta$ Induction of Smooth Muscle Cell Phenotype Requires Transcriptional and Post-transcriptional Control of Serum Response Factor." *The Journal of Biological Chemistry.* vol. 277, No. 8, pp. 6287-6295.

Xu, Weiming, Lizhi Liu, and Ian G. Charles. Feb. 2002. "Microencapsulated iNOS-expressing Calls Cause Tumor Suppression in Mice." *The FASEB Journal.* vol. 16, pp. 213-215.

Zubarev, Eugene R., Martin U. Pralle, Eli D. Sone, and Samuel I. Stupp. Feb. 2002. "Scaffolding of Polymers by Supramolecular Nanoribbons." *Advanced Materials.* vol. 14, No. 3, pp. 198-203.

Teng, Yang D., Erin B. Lavik, Xianlu Qu, Kook I. Park, •Jitka Ourednik, David Zurakowski, Robert Langer, and Evan Y. Snyder. Mar. 5, 2002. "Functional Recovery Following Traumatic Spinal Cord Injury Mediated by a Unique Polymer Scaffold Seeded with Neural Stem Cells." *Proceedings of the National Academy of Sciences of the United States of America.* vol. 99, No. 5, pp. 3024-3029.

Bradbury, Elizabeth J., Lawrence D. F. Moon, Reena J. Popat, Von R. King, Gavin S. Bennett, Preena N. Patel, James W. Fawcett, and Stephen B. McMahon. Apr. 11, 2002. "Chondroitinase ABC Promotes Functional Recovery After Spinal Cord Injury." *Nature.* vol. 416, pp. 636-640.

Hartgerink, Jeffrey D., Elia Beniash, and Samuel I. Stupp. Apr. 16, 2002. "Supramolecular Chemistry and Self-Assembly Special Feature: Peptide-Amphiphile Nanofibers: A Versatile Scaffold for the Preparation of Self-Assembling Materials." *Proceedings of the National Academy of Sciences of the United States of America.* vol. 99, No. 8, pp. 5133-5138.

Vauthey, Sylvain, Steve Santoso, Haiyan Gong, Nicki Watson, and Shuguang Zhang. Apr. 16, 2002. "Molecular Self-Assembly of Surfactant-like Peptides to Form Nanotubes and Nanovesicles." *Proceedings of the National Academy of Sciences of the United States of America.* vol. 99, No. 8, pp. 5355-5360.

Nowak, Andrew P., Victor Breedveld, Lisa Pakstis, Bulent Ozbas, David J. Pine, Darrin Pochan, and Timothy J. Deming. May 23, 2002. "Rapidly Recovering Hydrogel Scaffolds from Self-Assembling Diblock Copolypeptide Amphiphiles." *Nature.* vol. 417, pp. 424-428.

GrandPré, Tadzia, Shuxin Li, and Stephen M. Strittmatter. May 30, 2002. "Nogo-66 Receptor Antagonist Peptide Promotes Axonal Regeneration." *Nature.* vol. 417, pp. 547-551.

Storch, Alexander and Johannes Schwarz. May 2002. "Neural Stem Cells and Neurodegeneration." *Current Opinion in Investigational Drugs.* vol. 3, No. 5, pp. 774-781.

Lendlein, Andreas and Robert Langer. May 31, 2002. "Biodegradable, Elastic Shape-Memory Polymers for Potential Biomedical Applications." *Science*. vol. 296, pp. 1673-1676.

Qiu, Jin, Dongming Cai, Haining Dai, Marietta McAttee, Paul N. Hoffman, Barbara S. Bregman, and Marie T. Filbin. Jun. 13, 2002. "Spinal Axon Regeneration Induced by Elevation of Cyclic AMP." *Neuron*. vol. 34, pp. 895-903.

Catledge, Shane A., Marc D. Fries, Yogesh K. Vohra, William R. Lacefield, Jack E. Lemons, Shanna Woodard, and Ramakrishna Venugopalan. Jun.-Aug. 2002. "Nanostructured Ceramics for Biomedical Implants." *Journal of Nanoscience and Nanotechnology*. vol. 2, No. 3/4, pp. 293-312.

Alsberg, Eben, Kenneth W. Anderson, Amru Albeiruti, Jon A. Rowley, and David J. Mooney. Sep. 17, 2002. "Engineering Growing Tissues." *Proceedings of the National Academy of Sciences of the United States of America*. vol. 99, No. 19, pp. 12025-12030.

Kay, Sarina, Anil Thapa, Karen M. Haberstroh, and Thomas J. Webster. Oct. 2002. "Nanostructured Polymer/Nanophase Ceramic Composites Enhance Osteoblast and Chondrocyte Adhesion." *Tissue Engineering*. vol. 8, No. 5, pp. 753-761.

Chang, Hua, Chester W. Brown, and Martin M. Matzuk. Dec. 2002. "Genetic Analysis of the Mammalian Transforming Growth Factor-β Superfamily." *Endocrine Reviews*. vol. 23, No. 6, pp. 787-823.

Busqué, Félix, Stephanie A. Hopkins, and Joseph P. Konopelski. 2002. "Progress Toward a Peptidomimetic of Laminin-Derived Pentapeptide YIGSR: Synthesis of the Unique Tricyclic Core Structure." *J. Org. Chem*. vol. 67, No. 17, pp. 6097-6103.

Canaple, Laurence, Annemie Rehor, and David Hunkeler. 2002. "Improving Cell Encapsulation Through Size Control." *J. Biomater. Sci. Polymer. Edn*. vol. 13, No. 7, pp. 783-796.

Caplan, Michael R., Elissa M. Schwartzfarb, Shuguang Zhang, Roger D. Kamm, and Douglas A. Lauffenburger. 2002. "Control of Self-Assembling Oligopeptide Matrix Formation Through Systematic Variation of Amino Acid Sequence." *Biomaterials*. vol. 23, pp. 219-227.

Chen, Zhi Jiang, Yvonne Ughrin, and Joel M. Levine. 2002. "Inhibition of Axon Growth by Oligodendrocyte Precursor Cells." *Molecular and Cellular Neuroscience*. vol. 20, pp. 125-139.

Cornish, Toby, Darren W. Branch, Bruce C. Wheeler, and James T. Campanelli. 2002. "Microcontact Printing: A Versatile Technique for the Study of Synaptogenic Molecules." *Molecular and Cellular Neuroscience*. vol. 20, pp. 140-153.

Costa, Silvia, Thierry Planchenault, Cecile Charriere-Bertrand, Yann Mouchel, Christiane Fages, Sharon Juliano, Thierry Lefrançois, Georgia Barlovatz-Meimon, and Marcienne Tardy. 2002. "Astroglial Permissivity for Neuritic Outgrowth in Neuron-Astrocyte Cocultures Depends on Regulation of Laminin Bioavailability." *GLIA*. vol. 37, pp. 105-113.

Gariépy, Jean, Sandrine Rémy, Xiuguo Zhang, James R. Ballinger, Eleonora Bolewska-Pedyczak, Michael Rauth, and Stuart K. Bisland. 2002. "A Simple Two-Step Approach for Introducing a Protected Diaminedithiol Chelator During Solid-Phase Assembly of Peptides." *Bioconjugate Chem*. vol. 13, No. 3, pp. 679-684.

Glättli, Alice, Xavier Daura, Dieter Seebach, and Wilfred F. van Gunsteren. 2002. "Can One Derive the Confrontational Preference of a β-Peptide from Its CD Spectrum?" *Journal of the American Chemical Society*. vol. 124, No. 44, pp. 12972-12978.

Gutwein, Luke G. and Thomas J. Webster. 2002. "Osteoblast and Chrondrocyte Proliferation in the Presence of Alumina and Titania Nanoparticles." *Journal of Nanoparticle Research*. vol. 4, pp. 231-238.

Huang, Ning-Ping, Gabor Csucs, Kazunori Emoto, Yukio Nagasaki, Kazunori Kataoka, Marcus Textor, and Nicholas D. Spencer. 2002. "Covalent Attachment of Novel Poly(ethylene glycol)—Poly(DL-lactic acid) Copolymeric Micelles to $TiO_2$ Surfaces." *Langmuir*. vol. 18, No. 1, pp. 252-258.

Issac, Roy and Jean Chmielewski. 2002. "Approaching Exponential Growth with a Self-Replicating Peptide." *Journal of the American Chemical Society*. vol. 124, No. 24, pp. 6808-6809.

Joshi, Mital and Michael G. Fehlings. 2002. "Development and Characterization of a Novel, Graded Model of Clip Compressive Spinal Cord Injury in the Mouse: Part 1. Clip Design, Behavioral Outcomes, and Histopathology." *Journal of Neurotrauma*. vol. 19, No. 2, pp. 175-190.

Joshi, Mital and Michael G. Fehlings. 2002. "Development and Characterization of a Novel, Graded Model of Clip Compressive Spinal Cord Injury in the Mouse: Part 2. Quantitative Neuroanatomical Assessment and Analysis of the Relationships Between Axonal Tracts, Residual Tissue, and Locomotor Recovery." *Journal of Neurotrauma*. vol. 19, No. 2, pp. 191-203.

Kruger, Ryan G., Patrick Dostal, and Dewey G. McCafferty. 2002. "An Economical and Preparative Orthogonal Solid Phase Synthesis of Fluorescein and Rhodamine Derivatized Peptides: FRET Substrates for the *Staphylococcus aureus* Sortase SrtA Transpeptidase Reaction." *Chem. Commun*. pp. 2092-2093.

Lauer, L., A. Vogt, C. K. Yeung, W. Knoll, and A. Offenhäusser. 2002. "Electrophysiological Recordings of Patterned Rat Brain Stem Slice Neurons." *Biomaterials*. vol. 23, pp. 3123-3130.

Lavik, Erin, Yang D. Teng, Evan Snyder, and Robert Langer. 2002. "Speeding Neural Stem Cells on Scaffolds of PGA, PLA, and Their Copolymers." *Methods in Molecular Biology: Neural Stem Cells: Methods and Protocols*. vol. 198, pp. 89-97.

Marini, Davide M., Wonmuk Hwang, Douglas A. Lauffenburger, Shuguang Zhang, and Roger D. Kamm. 2002. "Left-Handed Helical Ribbon Intermediates in the Self-Assembly of a β-Sheet Peptide." *Nano Letters*. vol. 2, No. 4, pp. 295-299.

Ohsaki, Mio, Tatsuya Okuda, Akihiro Wada, Toshiya Hirayama, Takuro Niidome, and Haruhiko Aoyagi. 2002. "In Vitro Gene Transfection Using Dendritic Poly(L-lysine)." *Bioconjugate Chem*. vol. 13, No. 3, pp. 510-517.

Okano, Hideyuki. 2002. "Stem Cell Biology of the Central Nervous System." *Journal of Neuroscience Research*. vol. 69, pp. 698-707.

Parmar, Malin, Charlotta Skogh, Anders Björklund, and Kenneth Campbell. 2002. "Regional Specification of Neurosphere Cultures Derived from Subregions of the Embryonic Telecephalon." *Molecular and Cellular Neuroscience*. vol. 21, pp. 645-656.

Porter, A. E., L. W. Hobbs, V. Benezra Rosen, and M. Spector. 2002. "The Ultrastructure of the Plasma-Sprayed Hydroxyapatite-bone Interface Predisposing to Bone Bonding." *Biomaterials*. vol. 23, pp. 725-733.

Rowley, Jon A. and David J. Mooney. 2002. "Alginate Type and RGD Density Control Myoblast Phenotype." *Journal of Biomedical Materials Research*. vol. 60, pp. 217-223.

Santoso, Steve S., Sylvain Vauthey, and Shuguang Zhang. 2002. "Structures, Function and Applications of Amphiphilic Peptides." *Current Opinion in Colloid & Interface Science*. vol. 7, pp. 262-266.

Thiébaud, Pierre, Lars Lauer, Wolfgang Knoll, and Andreas Offenhäuser. 2002. "PDMS Device for Patterned Application of Microfluids to Neuronal Cells Arranged by Microcontact Printing." *Biosensors & Bioelectronics*. vol. 17, pp. 87-93.

Tryoen-Tóth, Petra, Dominique Vautier, Youssef Haikel, Jean-Claude Voegel, Pierre Schaaf, Johanna Chluba, and Joëlle Ogier. 2002. "Viability, Adhesion, and Bone Phenotype of Osteoblast-like Cells on Polyelectrolyte Multilayer Films." *Journal of Biomedical Materials Research*. vol. 60, pp. 657-667.

Young, Wise. 2002. "Spinal Cord Contusion Models." *Progress in Brain Research*. vol. 137, pp. 231-255.

Lutolf, Matthias P., Franz E. Weber, Hugo G. Schmoekel, Jason C. Schense, Thomas Kohler, Ralph Müller, and Jeffrey A. Hubbell. May 2003. "Repair of Bone Defects Using Synthetic Mimetics of Collagenous Extracellular Matrices." *Nature Biotechnology*. vol. 21, pp. 513-518.

Shaw, Derek and Molly S. Shoichet. May 2003. "Toward Spinal Cord Injury Repair Strategies: Peptide Surface Modification of Expanded Poly(Tetrafluoroethylene) Fibers for Guided Neurite Outgrowth in Vitro." *The Journal of Craniofacial Surgery*. vol. 14, No. 3, pp. 308-316.

Cheng, Hongwei, Wei Jiang, Frank M. Phillips, Rex C. Haydon, Ying Peng, Lan Zhou, Hue H. Luu, Naili An, Benjamin Breyer, Pantila Vanichakarn, Jan Paul Szatkowski, Jae Yoon Park, and Tong-Chuan He. Aug. 2003. "Osteogenic Activity of the Fourteen Types of Human Bone Morphogenetic Proteins (BMPs)." *The Journal of Bone & Joint Surgery*. vol. 85-A, No. 8, pp. 1544-1552, 141.

Pavlov, Georges, Stéphanie Finet, Karine Tatarenko, Evgueniya Korneeva, and Christine Ebel. 2003. "Conformation of Heparin Studied with Macromolecular Hydrodynamic Methods and X-ray Scattering." *Eur. Biophys. J.* vol. 32, pp. 437-449.

Arinzeh, Treena Livingston, Susan J. Peter, Michael P. Archambault, Christian van den Bos, Steve Gordon, Karl Kraus, Alan Smith, and Sudha Kadiyala. Oct. 2003. "Allogeneic Mesenchymal Stem Cells Regenerate Bone in a Critical-Sized Canine Segmental Defect." *The Journal of Bone & Joint Surgery.* vol. 85-A, No. 10, pp. 1927-1935.

Zhang, Shuguang. Oct. 2003. "Fabrication of Novel Biomaterials Through Molecular Self-Assembly." *Nature Biotechnology.* vol. 21, No. 10, pp. 1171-1178.

Aggeli, Amalia, Mark Bell, Lisa M. Carrick, Colin W. G. Fishwick, Richard Harding, Peter J. Mawer, Sheena E. Radford, Andrew E. Strong, and Neville Boden. 2003. "pH as a Trigger of Peptide β-Sheet Self-Assembly and Reversible Switching Between Nematic and Isotropic Phases." *Journal of the American Chemical Society.* vol. 125, No. 23, pp. 9619-9628.

Alsina, Jordi and Fernando Albercio. 2003. "Solid-Phase Synthesis of C-Terminal Modified Peptides." *Biopolymers (Peptide Science).* vol. 71, pp. 454-477.

Anthony, Shawn G. 2003. "Injectable Biomaterials for Bone Tissue Engineering."

Boontheekul, Tanyarut and David J. Mooney. 2003. "Protein-Based Signaling Systems in Tissue Engineering." *Current Opinion in Biotechnology.* vol. 14, pp. 559-565.

Fauza, Dario O. 2003. "Tissue Engineering: Current State of Clinical Application." *Current Opinion in Pediatrics.* vol. 15, pp. 267-271.

Ganesh, S. and R. Jayakumar. 2003. "Structural Transitions Involved in a Novel Amyloid-Like β-Sheet Assemblage of Tripeptide Derivatives." *Biopolymers.* vol. 70, pp. 336-345.

Ganesh, S., S. Prakash, and R. Yamakumar. 2003. "Spectroscopic Investigation of Gel-Forming β-Sheet Assemblage of Peptide Derivatives." *Biopolymers.* vol. 70, pp. 346-354.

Goeden-Wood, Nichole L., Jay D. Keasling, and Susan J. Muller. 2003. "Self-Assembly of a Designed Protein Polymer into β-Sheet Fibrils and Responsive Gels." *Macromolecules.* vol. 36, No. 8, pp. 2932-2938.

Ishihara, Masayuki, Kiyohaya Obara, Toshiaki Ishizuka, Masanori Fujita, Masato Sato, Kazunori Masuoka, Yoshio Saito, Hirofumi Yura, Takemi Matsui, Hidemi Hattori, Makoto Kikuchi, and Akira Kurita. 2003. "Controlled Release of Fibroblast Growth Factors and Heparin from Photocrosslinked Chitosan Hydrogels and Subsequent Effect on in Vivo Vascularization." *Journal of Biomedical Materials Research.* vol. 64A, pp. 551-559.

Malkar, Navdeep B., Janelle L. Lauer-Fields, Darius Juska, and Gregg B. Fields. 2003. "Characterization of Peptide-Amphiphiles Possessing Cellular Activation Sequences." *Biomacromolecules.* vol. 4, No. 3, pp. 518-528.

Niece, Krista L., Jeffrey D. Hartgerink, Jack J. J. M. Donners, and Samuel I. Stupp. 2003. "Self-Assembly Combining Two Bioactive Peptide-Amphiphile Molecules into Nanofibers by Electrostatic Attraction." *Journal of the American Chemical Society.* vol. 125, No. 24, pp. 7146-7147.

Steward, Oswald, Binhai Zheng, and Marc Tessier-Lavigne. 2003. "False Resurrections: Distinguishing Regenerated from Spared Axons in the Injured Central Nervous System." *The Journal of Comparative Neurology.* vol. 459, pp. 1-8.

Wu, Sufan, Yoshihisa Suzuki, Yoko Ejiri, Toru Noda, Hongliang Bai, Masaaki Kitada, Kazuya Kataoka, Masayoshi Ohta, Hirotomi Chou, and Chizuka Ide. 2003. "Bone Marrow Stromal Cells Enhance Differentiation of Cocultured Neurosphere Cells and Promote Regeneration of Injured Spinal Cord." *Journal of Neuroscience Research.* vol. 72, pp. 343-351.

Yamada, Norihiro, Tsukasa Komatsu, Hirotsugu Yoshinaga, Kayo Yoshizawa, Susumu Edo, and Masashi Kunitake. 2003. "Self-Supporting Elastic Film without Covalent Linkages as a Hierarchically Integrated β-Sheet Assembly." *Angew. Chem. Int. Ed.* vol. 42, pp. 5496-5499.

Zhang, Yan, Hongwei Gu, Zhimou Yang, and Bing Xu. 2003. "Supramolecular Hydrogels Respond to Ligand-Receptor Interaction." *Journal of the American Chemical Society.* vol. 125, No. 45, pp. 13680-13681.

Hirano, Yoshiaki and David J. Mooney. Jan. 5, 2004. "Peptide and Protein Presenting Materials for Tissue Engineering." *Advanced Materials.* vol. 16, No. 1, pp. 17-25.

Silva, Gabriel A., Catherine Czeisler, Krista L. Niece, Elia Beniash, Daniel A. Harrington, John A. Kessler, and Samuel I. Stupp. Feb. 27, 2004. "Selective Differentiation of Neural Progenitor Cells by High-Epitope Density Nanofibers." *Science.* vol. 303, pp. 1352-1355.

Faulkner, Jill R., Julia E. Herrmann, Michael J. Woo, Keith E. Tansey, Ngan B. Doan, and Michael V. Sofroniew. Mar. 3, 2004. "Reactive Astrocytes Protect Tissue and Preserve Function after Spinal Cord Injury." *The Journal of Neuroscience.* vol. 24, No. 9, pp. 2143-2155.

Cao, Renhai, Anna Eriksson, Hajime Kubo, Kari Alitalo, Yihai Cao, Johan Thyberg. Mar. 19, 2004. "Comparative Evaluation of FGF-2-, VEGF-A-, and VEGF-C-Induced Angiogenesis, Lymphangiogenesis, Vascular Fenestrations, and Permeability." *Circulation Research.* vol. 94, pp. 664-670.

Anthony, Shawn G. Mar. 28-Apr. 1, 2004. "Self-Assembling Nanofiber Matrix for Bone Regeneration." *The 227th ACS National Meeting.* Anaheim, CA.

Donners, Jack J. J. M. Mar. 28-Apr. 1, 2004. "Growth Factor Binding Self-Assembling Nanofiber Networks for Tissue Regeneration." *The 227th ACS National Meeting.* Anaheim, CA.

Nikulina Elena, J. Lille Tidwell, Hai Ning Dai, Barbara S. Bregman, and Marie T. Filbin. Jun. 8, 2004. "The Phosphodiesterase Inhibitor Rolipram Delivered after a Spinal Cord Lesion Promotes Axonal Regeneration and Functional Recovery." *Proceedings of the National Academy of Sciences of the United States of America.* vol. 101, No. 23, pp. 8786-8790.

Pearse, Damien D., Francisco C. Pereira, Alexander E. Marcillo, Margaret L. Bates, Yerko A. Berrocal, Marie T. Filbin, and Mary Bartlett Bunge. Jun. 2004. "cAMP and Schwann Cells Promote Axonal Growth and Functional Recovery After Spinal Cord Injury." *Nature Medicine.* vol. 10, No. 6, pp. 610-616.

Lu, Paul, Hong Yang, Leonard L. Jones, Marie T. Filbin, and Mark H. Tuszynski. Jul. 14, 2004. "Combinatorial Therapy with Neurotrophins and cAMP Promotes Axonal Regeneration beyond Sites of Spinal Cord Injury." *The Journal of Neuroscience.* vol. 24, No. 28, pp. 6402-6409.

Lee, K. W., J. J. Yoon, J. H. Lee, S. Y. Kim, H. J. Jung, S. J. Kim, J. W. Joh, H. H. Lee, D. S. Lee, and S. K. Lee. 2004. "Sustained Release of Vascular Endothelial Growth Factor From Calcium-Induced Alginate Hydrogels Reinforced by Heparin and Chitosan." *Transplantation Proceedings.* vol. 36, pp. 2464-2465.

Matsumura, Sachiko, Shinobu Uemura, and Hisakazu Mihara. 2004. "Fabrication of Nanofibers with Uniform Morphology by Self-Assembly of Designed Peptides." *Chem. Eur. J.* vol. 10, pp. 2789-2794.

Sieminski, A. L., R. P. Hebbel, and K. J. Gooch. 2004. "The Relative Magnitudes of Endothelial Force Generation and Matrix Stiffness Modulate Capillary Morphogenesis in Vitro." *Experimental Cell Research.* vol. 297, pp. 574-584.

Vandermeulen, Guido W. M. and Harm-Anton Klok. 2004. "Peptide/Protein Hybrid Materials: Enhanced Control of Structure and Improved Performance through Conjugation of Biological and Synthetic Polymers." *Macromolecular Bioscience.* vol. 4, pp. 383-398.

Wang, Lin-Fa and Meng Yu. 2004. "Epitope Identification and Discovery Using Phage Display Libraries: Applications in Vaccine Development and Diagnostics." *Current Drug Targets.* vol. 5, No. 1, pp. 1-15.

Sayle, Roger. Printed Nov. 9, 2005. "Physiological Ionization and pKa Prediction." http://www.daylight.com/meetings/emug00/Sayle/pkapredict.html. pp. 1-13.

Bull, Steve R., Mustafa O. Guler, Rafael E. Bras, Thomas J. Meade, and Samuel I. Stupp. 2005. "Self-Assembled Peptide Amphiphile Nanofibers Conjugated to MRI Contrast Agents." *Nano Letters.* vol. 5, No. 1, pp. 1-4.

Guler, Mustafa O., Stephen Soukasene, James F. Hulvat, and Samuel I. Stupp. 2005. "Presentation and Recognition of Biotin on Nanofibers Formed by Branched Peptide Amphiphiles." *Nano Letters.* vol. 5, No. 2, pp. 249-252.

Loudon, M. "Amino Acid Structures at Physiological pH." Printed Jun. 5, 2006. www.brynmawr.edu/Acads/Chem/mnerzsto/amino_acids.htm, amino_acids_2.gif, and amino_acids3.htm.

Nomizu, Motoyoshi, Keizo Yamamura, Hynda K. Kleinman, and Yoshihiko Yamada. Aug. 1, 1993. "Multimeric Forms of Tyr-Ile-Gly-Ser-Arg (YIGSR) Peptide Enhance the Inhibition of Tumor Growth and Metastasis." Cancer Research. vol. 53, pp. 3459-3461.

Jin, Young-Gu and K. J. Chang. Feb. 26, 2001. "Mechanism for the Enhanced Diffusion of Charged Oxygen Ions in SiO2." Physical Review Letters. vol. 86, No. 9, pp. 1793-1796.

Matsui, Hiroshi and Robert MacCuspie. Dec. 2001. "Metalloporphyrin Nanotube Fabrication Using Peptide Nanotubes as Templates." Nano Letters. vol. 1, No. 12, pp. 671-675.

Irvine, Darrel J. and Anne M. Mayes. 2001. "Nanoscale Clustering of RGD Peptides at Surfaces Using Comb Polymers. 1. Synthesis and Characterization of Comb Thin Films." Biomacromolecules. vol. 2, No. 1, pp. 85-94.

Matsui, Hiroshi, Precila Porrata, and Gary E. Douberly, Jr. 2001. "Protein Tubule Immobilization on Self-Assembled Monolayers on Au Substrates." Nano Letters. vol. 1, No. 9, pp. 461-464.

Slocik, Joseph M., Joshua T. Moore, and David W. Wright. Mar. 2002. Monoclonal Antibody Recognition of Histidine-Rich Peptide Encapsulated Nanoclusters. Nano Letters. vol. 2, No. 3, pp. 169-173.

Shih, Sheng-Ming, Wei-Fang Su, Yuh-Jiuan Lin, Cen-Shawn Wu, and Chii-Dong Chen. 2002. "Two-Dimensional Arrays of Self-Assembled Gold and Sulfur-Containing Fullerene Nanoparticles." Langmuir. vol. 18, No. 8, pp. 3332-3335.

Wong, Michael S., Jennifer N. Cha, Kyoung-Shin Choi, Timothy J. Deming, and Galen D. Stucky. 2002. "Assembly of Nanoparticles into Hollow Spheres Using Block Copolypeptides." Nano Letters. vol. 2, No. 6, pp. 583-587.

"AccessScience Search Results. Amphiphile." Accessed online May 7, 2007. http://www.accessscience.com/search/asearch?location=titlestext&newSearch=1&pubpriv=private&categories=dictionary&categval=dictionary&text=amphiphile. McGraw-Hill Encyclopedia of Science & Technology Online.

Jackowski, Andre. 1995. "Neural Injury Repair: Hope for the Future as Barriers to Effective CNS Regeneration Become Clearer." J. Neurosurg. vol. 9, pp. 303-317.

Knake, Rene, Amir W. Fahmi, Syed A. M. Tofail, Jason Clohessy, Miroslav Mihov, and Vincent J. Cunnane. 2005. "Electrochemical Nucleation of Gold Nanoparticles in a Polymer Film at a Liquid-Liquid Interface." Langmuir. vol. 21, No. 3, pp. 1001-1008.

* cited by examiner

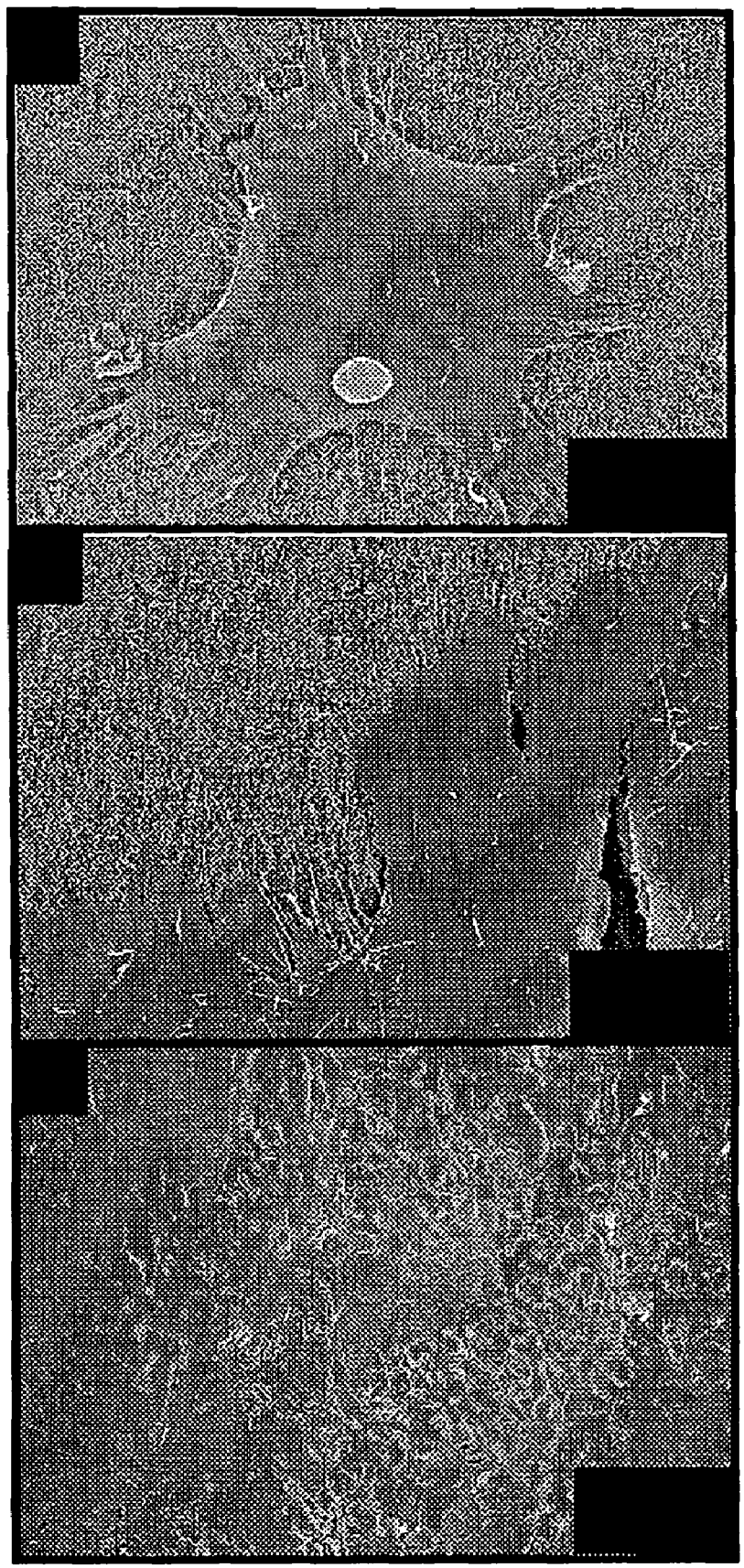

SEQUENCE LISTING

<160> NUMBER OF SEQ ID NOS: 16

<210> SEQ ID NO 1
<211> LENGTH: 5

```
<212> TYPE: PRT
<213> ORGANISM: Homo sapiens

<400> SEQUENCE: 1

Tyr Ile Gly Ser Arg
1               5

<210> SEQ ID NO 2
<211> LENGTH: 5
<212> TYPE: PRT
<213> ORGANISM: Homo sapiens

<400> SEQUENCE: 2

Ile Lys Val Ala Val
1               5

<210> SEQ ID NO 3
<211> LENGTH: 12
<212> TYPE: PRT
<213> ORGANISM: Homo sapiens
<220> FEATURE:
<221> NAME/KEY: S
<222> LOCATION: (9)..(9)
<223> OTHER INFORMATION: phosphorylated serine
<220> FEATURE:
<221> NAME/KEY: S
<222> LOCATION: (11)..(11)
<223> OTHER INFORMATION: phosphorylated serine

<400> SEQUENCE: 3

Cys Cys Cys Cys Gly Gly Gly Ser Ser Asp Ser Asp
1               5                   10

<210> SEQ ID NO 4
<211> LENGTH: 11
<212> TYPE: PRT
<213> ORGANISM: Homo sapiens
<220> FEATURE:
<221> NAME/KEY: S
<222> LOCATION: (8)..(8)
<223> OTHER INFORMATION: phosphorylated serine

<400> SEQUENCE: 4

Cys Cys Cys Cys Gly Gly Gly Ser Arg Gly Asp
1               5                   10

<210> SEQ ID NO 5
<211> LENGTH: 8
<212> TYPE: PRT
<213> ORGANISM: Homo sapiens
<220> FEATURE:
<221> NAME/KEY: S
<222> LOCATION: (8)..(8)
<223> OTHER INFORMATION: phosphorylated serine

<400> SEQUENCE: 5

Cys Cys Cys Cys Gly Gly Gly Ser
1               5

<210> SEQ ID NO 6
<211> LENGTH: 7
<212> TYPE: PRT
<213> ORGANISM: Homo sapiens
<220> FEATURE:
<221> NAME/KEY: S
<222> LOCATION: (4)..(4)
<223> OTHER INFORMATION: phosphorylated serine

<400> SEQUENCE: 6
```

```
Gly Gly Gly Ser Arg Gly Asp
1               5
```

```
<210> SEQ ID NO 7
<211> LENGTH: 11
<212> TYPE: PRT
<213> ORGANISM: Homo sapiens
<220> FEATURE:
<221> NAME/KEY: S
<222> LOCATION: (8)..(8)
<223> OTHER INFORMATION: phosphorylated serine

<400> SEQUENCE: 7

Ala Ala Ala Ala Gly Gly Gly Ser Arg Gly Glu
1               5                   10
```

```
<210> SEQ ID NO 8
<211> LENGTH: 11
<212> TYPE: PRT
<213> ORGANISM: Homo sapiens
<220> FEATURE:
<221> NAME/KEY: S
<222> LOCATION: (8)..(8)
<223> OTHER INFORMATION: phosphorylated serine

<400> SEQUENCE: 8

Cys Cys Cys Cys Gly Gly Gly Ser Lys Gly Glu
1               5                   10
```

```
<210> SEQ ID NO 9
<211> LENGTH: 11
<212> TYPE: PRT
<213> ORGANISM: Homo sapiens
<220> FEATURE:
<221> NAME/KEY: S
<222> LOCATION: (8)..(8)
<223> OTHER INFORMATION: phosphorylated serine

<400> SEQUENCE: 9

Ala Ala Ala Ala Gly Gly Gly Ser Lys Gly Glu
1               5                   10
```

```
<210> SEQ ID NO 10
<211> LENGTH: 11
<212> TYPE: PRT
<213> ORGANISM: Homo sapiens

<400> SEQUENCE: 10

Cys Cys Cys Cys Gly Gly Gly Ser Arg Gly Asp
1               5                   10
```

```
<210> SEQ ID NO 11
<211> LENGTH: 13
<212> TYPE: PRT
<213> ORGANISM: Homo sapiens

<400> SEQUENCE: 11

Cys Cys Cys Cys Gly Gly Gly Glu Ile Lys Val Ala Val
1               5                   10
```

```
<210> SEQ ID NO 12
<211> LENGTH: 12
<212> TYPE: PRT
<213> ORGANISM: Homo sapiens
<220> FEATURE:
<221> NAME/KEY: S
<222> LOCATION: (8)..(8)
```

```
<223> OTHER INFORMATION: phosphorylated serine

<400> SEQUENCE: 12

Cys Cys Cys Cys Gly Gly Gly Ser Arg Gly Asp Ser
1               5                   10

<210> SEQ ID NO 13
<211> LENGTH: 13
<212> TYPE: PRT
<213> ORGANISM: Homo sapiens

<400> SEQUENCE: 13

Cys Cys Cys Cys Gly Gly Gly Lys Ile Lys Val Ala Val
1               5                   10

<210> SEQ ID NO 14
<211> LENGTH: 4
<212> TYPE: PRT
<213> ORGANISM: Homo sapiens

<400> SEQUENCE: 14

Arg Gly Asp Ser
1

<210> SEQ ID NO 15
<211> LENGTH: 11
<212> TYPE: PRT
<213> ORGANISM: Homo sapiens
<220> FEATURE:
<221> NAME/KEY: S
<222> LOCATION: (8)..(8)
<223> OTHER INFORMATION: phosphorylated serine

<400> SEQUENCE: 15

Cys Cys Cys Cys Gly Gly Gly Ser Lys Gly Glu
1               5                   10

<210> SEQ ID NO 16
<211> LENGTH: 11
<212> TYPE: PRT
<213> ORGANISM: Homo sapiens
<220> FEATURE:
<221> NAME/KEY: S
<222> LOCATION: (8)..(8)
<223> OTHER INFORMATION: phosphorylated serine
<220> FEATURE:
<221> NAME/KEY: S
<222> LOCATION: (10)..(10)
<223> OTHER INFORMATION: phosphorylated serine

<400> SEQUENCE: 16

Cys Cys Cys Cys Gly Gly Gly Ser Asp Ser Asp
1               5                   10
```

METHODS AND MATERIALS FOR NANOCRYSTALLINE SURFACE COATINGS AND ATTACHMENT OF PEPTIDE AMPHIPHILE NANOFIBERS THEREON

This application claims priority benefit from U.S. provisional applications Ser. Nos. 60/446,421 and 60/495,965 filed Feb. 11, 2003 and Aug. 18, 2003, respectively, each of which is incorporated herein by reference in its entirety.

The United States Government has certain rights to this invention pursuant to grant No. DEFG02-00ER45810 and DMR0108342 from the Department of Energy and the National Science Foundation, respectively, to Northwestern University.

BACKGROUND

Techniques of tissue engineering employing biocompatible scaffolds provide viable alternatives to prosthetic materials currently used in prosthetic and reconstructive surgery (e.g., craniomaxillofacial and spinal surgery). These materials also hold promise in the formation of tissue or organ equivalents to replace diseased, defective, or injured tissues. Compatible, biodegradable materials may be used for scaffolds which initiate and sustain tissue or bone growth, but which are naturally degraded over time within the body. Such materials may also be used for controlled release of therapeutic materials (e.g., genetic material, cells, hormones, drugs, or pro-drugs) into a predetermined area. Polymers, such as polylactic acid, polyorthoesters, and polyanhydrides, used to create these scaffolds are difficult to mold and, result in, among other things, poor cell attachment and poor integration into the site where the tissue engineered material is utilized. With some exceptions, they also lack biologically relevant signals.

Self-assembled peptide-amphiphile nanofibers have been used to direct the growth of biominerals such as hydroxyapatite. These nanofibers are comprised peptide-amphiphiles, that are comprised of a hydrophobic aliphatic tail coupled to a relatively hydrophilic peptide head group. The peptide head group may include at least two segments: a structural segment and a functional segment. Structural segments may include between 2 and 4 cysteine residues may be used to covalently stabilize the self-assembled peptide amphiphile structures via disulfide bond formation between individual peptide amphiphile molecules within a fiber. Alternatively, the structural segment may contain other residues, such as serine, leucine, alanine, or glycine for example. Though these residues may not promote covalent stabilization of the nanofibers, they may participate in structural organization, such as beta-sheet formation, in the assembled nanofibers. The functional head group may be composed of different amino acid combinations and include moieties such as carboxyl, thiol, amine, phosphate, and hydroxyl functional groups located near the end of the molecule most distant from the molecule's aliphatic tail. Examples of carboxyl group-containing residues include aspartic acid or glutamic acid. Examples of amine or guanidinium-containing residues include lysine or arginine respectively. When the peptide amphiphiles are self-assembled under aqueous conditions, it is expected that these functional residues will be displayed near the self-assembled micelle (generally a nanofiber) surface where they may be available for reaction with other moieties to bind the peptide amphiphile.

The versatility and functionality of these self-assembling nanofibrous materials may prove to be useful in tissue repair, cell growth, or organ reconstruction. The term tissue includes muscle, nerve, vascular, and bone tissue and other common understandings of tissue. The present invention may also find application in regulation, inhibition or promotion of axon outgrowth in neurons as well as the regulation, inhibition or promotion of cell-substrate adhesion among nerve cells. Coating these peptide amphiphile compositions on surfaces of scaffolds and implants, for example stainless steel stents, electrodes for electrical stimulation of nerves, or metal-based orthopedic implants, may furthermore enhance existing tissue engineering strategies. Importantly, multiple peptide signals may be used in the same supramolecular self assembled peptide amphiphile to accomplish different and potentially synergistic effects.

The peptide amphiphile composition(s) of such a system may include a peptide component having residues capable of intermolecular cross-linking. The thiol moieties of cysteine residues can be used for intermolecular disulfide bond formation through introduction of a suitable oxidizing agent or under physiological conditions. Conversely such bonds can be cleaved by a reducing agent introduced into the system or under reducing conditions. The concentration of cysteine residues, when utilized, can also be varied to control the chemical and/or biological stability of the nanofibrous system and therefore control the rate of therapeutic delivery or release of cells or other beneficial agent, using the nanofibers as the carriers. For example, enzymes could be incorporated into such nanofibers to control their biodegradation rate through hydrolysis of the disulfide bonds. Such degradation and/or the concentration of the cysteine residues can be utilized in a variety of tissue engineering applications. The thiol functionality of such peptide amphiphiles may also be useful for binding the supramolecular structures to surfaces.

The complimentary nature of the biological portions of the peptide amphiphiles may mimic amino acid sequences found in naturally occurring peptides. Self-assembled gels composed of peptide-amphiphile nanofibers with the RGD peptide sequence mimic the function of collagen fibrils to organize and direct the growth of the hydroxyapatite crystals. Other potentially useful amino acid sequences in such peptides may include the SEQ ID NO:1 YIGSR and SEQ ID NO:2 IKVAV amino acid sequences. Such amino acid sequences in self assembled peptide amphiphiles may have a synergistic effect on cell growth and nerve regeneration. The growth of cells on substrates implanted or delivered to the body would be beneficial to implantation of artificial hearts, restoring nerve function, healing of grafting blood vessels; forming skin grafts and preparing "artificial skin" by culturing epidermal cells on a fibrous lattice.

Damage to the endothelial and medial layers of a blood vessel, such as often occurs in the course of balloon angioplasty and stent procedures, has been found to stimulate neointimal proliferation, leading to restenosis of atherosclerotic vessels. The normal endothelium, which lines blood vessels, is uniquely and completely compatible with blood. Endothelial cells initiate metabolic processes which actively discourage platelet deposition and thrombus formation in vessel walls. Damaged arterial surfaces within the vascular system are highly susceptible to thrombus formation. While systemic drugs have been used to prevent coagulation and to inhibit platelet aggregation, a need exists to treat the damaged arterial surface directly to prevent thrombus formation and subsequent intimal smooth muscle cell proliferation.

Stents made up of metals such as titanium and its alloys have been designed to promote organized endothelial cell growth. Such stents comprise a plurality of depressions in the surface of at least a portion of the stent body, preferably arranged in a regular pattern on at least the interior surface of the stent body, such as a waffle weave. Other stents have surface features which comprise a plurality of pleats, ridges, channels or pores in the stent body wherein at least some of the pores run between the interior and exterior sides of the stent body (i.e., penetrate the stent body) and are sized to promote the organized cell growth.

The directed growth of cells, for example nerve cells and endothelial cells, on implantable surfaces and scaffolds would be desirable for the regeneration and growth of cells, organs, and tissue within the body. It would be desirable to provide surgical implants that may facilitate the growth of tissue, vascular tissues, nerve, and cells on or in tissue surrounding the surgical implant. It would be desirable for new and better scaffolds, implants, stents and electrode for placement into a body that are adapted to promote growth of infiltrating cells into organized cellular structures, such as take place during angiogenesis and/or neovascularization, to aid in repair of damaged body organs and vessels.

As part of a related consideration, titanium and its alloys have been used extensively as skeletal implant materials where the metals' high strength to weight ratio, toughness and the bioinert character of the naturally forming oxide layer have lead to widespread clinical success. As tissue engineering has developed, however, researchers have explored the use of calcium phosphate coatings on titanium-based implant surfaces to introduce an element of bioactivity to the otherwise inert oxidized metal surfaces. In vitro studies have shown that calcium phosphates may form osteoconductive coatings which enhance cellular attachment and proliferation. In vivo models have shown an improvement in implant interfacial strength when titanium surfaces are coated with various calcium phosphate coatings, often hydroxyapatite ($Ca_{10}(PO_4)_2(OH)_2$). Studies have also shown that degradation of these calcium phosphate coatings at implant-tissue interfaces facilitates the accelerated formation of de novo bone.

Commonly used methods for coating Ti with these calcium phosphate coatings include plasma spraying, electrophoresis, sol-gel, and solution-phase precipitation. Methods such as plasma spraying or sol gel tend to produce dense, often highly crystalline apatitic phases with little or no phase selectivity, and some of these methods are also unable to coat interior surfaces of porous titanium structures. Many of these methods for growth involve extremely long growth times, weeks to months, offer little control over crystal size or shape, and lack any added chemical functionality, such as that afforded by organic macromolecules. Organic macromolecules have been known to play roles in biomineral crystal modification. Additionally, where clusters form on porous surfaces, surface coating is frequently less than 100%. Solution-phase growth, however, enables nucleation of calcium phosphate coatings directly on implant surfaces, even porous surfaces. In addition, this wet chemical approach allows for the formation of not only hydroxyapatite, but also other biologically relevant calcium phosphate phases, such as octacalcium phosphate, ($Ca_8H_2(PO_4)_6 \cdot 5H_2O$), a precursor to hydroxyapatite. Solution-phase growth of these coatings also allows for the introduction of organic macromolecules into the coating, a feature not possible with some of the high temperature coating processes, such as plasma spraying.

Work has been done investigating the interactions of various biological macromolecules with calcium phosphate coatings. The growth of calcium phosphate coatings in the presence of biomolecules such as albumin, fibronectin, and poly (aminoacids), is substantially inhibited. Poly(L-lysine), for example, is a well-established cell adhesion promoter with excellent chemical functionality, but has been shown to inhibit apatite growth on a titanium alloy surface. Poly(amino acids) have been used as nucleating agents and macromolecular tethers to address this problem by growing poly(L-lysine)-containing organoapatite onto poly(amino-acid)-coated titanium-based surfaces. This method uses poly(amino acids) in several of the coating steps and layers; it also produces relatively bulky clusters of organoapatite, which may be disadvantageous in coating structures with fine porous textures. An alternative approach investigated is growing a calcium phosphate coating containing albumin onto a preexisting calcium phosphate layer.

It would be desirable to form polyamine-modified nanotextured calcium phosphate coating on implantable metal surfaces. Grown onto calcium phosphate seeds the new material combines the versatility and simplicity of solution-phase calcium phosphate growth on an implantable surface with the chemical and biological functionality of a poly(amine).

It would be desirable to coat the surfaces of materials with biominerals so that substantially all of the surface is coated, and that the coating provides a favorable surface for chemical modification, attachment of peptide amphiphile nanofibers, cell and tissue growth and adhesion. It would further be desirable if the coating could be applied to a material suitable for implant into a patient and that the coating be degradable under physiological conditions.

SUMMARY

In part, embodiments of the present invention are directed to binding self assembled peptide amphiphiles to other materials such as metals. The newly formed linkages would bond the original self assembled peptide amphiphile nanofiber or spherical micelle assembly to another material. Bonding between the suitable self assembled nanofibers or micelles and the secondary surface may be used to further orient cell or tissue growth on the secondary surface. Alternatively, peptide amphiphiles may be bonded to surfaces and used to orient grown of peptide amphiphile nanofibers, or may be used to initiate self assembly of nanofiber structures on the material surface. Such surfaces would be useful for tissue repair, adherence of cells to implants, and minimization of conditions such as restenosis when the material of interest is a stent.

The binding of the peptide amphiphile with the secondary surface may be by the physisorption, chemisorption, or covalent attachment of peptide amphiphiles, or self assembled nanofiber or micelles comprising them with the surfaces. Examples of such binding include but are not limited to ionic, coordination, chelation, amide or ester linkages between the self-assembled nanostructures and the surface. Such a binding scheme is expected to provide a stable mechanism for attachment of peptidic nanostructures to other materials, including metal surfaces, polymers, peptide-modified biomaterial coatings, or other peptide containing structures. This attachment would allow a peptide containing micelle to be robustly stabilized on a material surface. Such a delivery scheme may lend itself to applications ranging from modifying cell-specific behaviors to drug delivery. In one embodiment the peptide amphiphile nanofibers contain a carboxyl-rich peptide sequence. Such peptide amphiphile are bound to surfaces displaying free amines. Alternatively, the peptide amphiphile nanofibers could contain residues displaying the free amines, while the secondary surface or structure could display carboxyl functional groups.

With regard to such functionally modified surfaces, consider the embodiments of this paragraph through paragraph 0025, inclusive. An embodiment of the present invention is an organically modified biomineral coating on an implantable substrate whose surface has been pre-seeded with a mineral.

In a preferred embodiment the organically-modified coating comprises calcium phosphate coated onto an metal substrate that has been pre-seeded with calcium phosphate. One embodiment of the present invention is a method for coating a substrate with a biomineral coating.

Embodiments of the present invention include poly(L-lysine)-modified nanotextured calcium phosphate coating on titanium surfaces which is grown onto calcium phosphate seeds on the metal surface.

In an embodiment of the present invention, the coating on the pre-seeded substrate is comprised of (calcium-) metal deficient (octacalcium phosphate) mineral, the crystal growth of which has been frustrated and modified by a polyamine, and preferably a polyamine that includes amino acids such as poly(L-lysine) that are present during mineralization. It is furthermore believed that the (poly(L-lysine)) poly(amino acid) is intimately incorporated into the mineral phase.

One embodiment of the present invention is a composition for coating a substrate with a modified crystalline material surface for promoting cell attachment, tissue growth, or use in delivering therapeutic compositions. The coating solution comprises a solution of a dissolve crystalline material and a polyamine and preferably a polypeptide or acid salt thereof. The composition includes the dissolved crystalline material of interest and a polyamine that may include amino acids monomers. Preferably the polymer includes amino acids which when incorporated into the mineral have free functional groups for forming bonds with peptides, peptide amphiphiles, proteins, and cells. Preferably the polymer includes lysine monomers, and more preferably is poly-lysine or acid salts thereof. In one embodiment the coating is useful for cell growth and cell adhesion and the coating is susceptible to degradation under physiological conditions.

Another embodiment of the present invention is a substrate for growing cells, tissues, or for releasing therapeutic compositions. Such a substrate may be used in vitro to culture cells or tissue or it may be used in vivo to grow or culture cells or tissues such as bone. The substrate will be made of a biocompatible material whose surface has been preseeded with a mineral and that is subsequently coated with a mineral or material whose normal crystalline structure is modified by incorporation of a polyamine, preferably a polypeptide, within the material. The coating on the substrate may be further bonded to peptides by another bond, such as a disulfide or amide bond to the polyamine in the coating material or by other bonds to the crystalline material itself Alternatively the coating on the substrate may be bonded to self-assembled peptide amphiphiles or cross linked self assembled peptide amphiphiles, preferably through an amide bond. The material coating the substrate may also include oxide, hydroxide, phosphate, carbonate, oxalate, and combinations of these ions which may themselves be bonded with peptides or self assembled peptide amphiphiles.

Another embodiment of the present invention is a method for modifying the morphology of a material coating on a substrate. The method comprises pre-seeding a biologically compatible substrate and then treating the pre-seeded substrate with a composition that is a solution of a dissolved crystalline material or biomineral with a polyamine or poly (amino acid), or acid addition salt thereof, that will be incorporated into the crystalline material or biomineral to form a nanocrystalline mineral. The morphology of the resulting coating may be controlled by the composition and the method of coating the substrate. The method may further include acts of bonding molecules to the polyamine incorporated into the nanocrystalline material of the coating.

The morphology of the embodied coatings resulting of the present invention consists of irregular features 1-2 orders of magnitude smaller than purely inorganic mineral coatings. This increased texture and reduced feature size will be advantageous for promoting cell attachment, proliferation, and spreading on monolithic substrates or surface coated with such organically modified materials. In addition, the disrupted, poorly crystalline character of the coating, combined with the enzyme-vulnerable organic component of the mineral composite will advantageously make the coating particularly accessible for natural re-absorption and remodeling processes. Finally, the incorporation of polyamino acids into the coating provides additional chemical functionality via the free amines or sulfide groups on the side chains of the lysine polymer. Such chemical functionality may be used for incorporation or covalent attachment of biological molecules, such as growth factors, biologically relevant peptide sequences, or therapeutic drugs.

The new material combines the versatility and simplicity of solution-phase calcium phosphate growth on titanium with the chemical and biological functionality of poly(L-lysine).

Accordingly, embodiments of the present invention can also comprise self assembled peptide amphiphile coated onto implantable scaffolds, surgical devices, electrodes, stents and other substrate surfaces. Peptide amphiphile-comprising coatings on these surfaces may enhance the growth of cells and thus tissues within the body.

One embodiment of the present invention provides a system of self-assembled peptide-amphiphiles micelles, spherical or cylindrical, comprising one or more biological signals that are deposited onto a substrate. Variations of structural peptide sequences in the peptide amphiphile may enable the assembled nanofibers to be reversibly cross-linked on the substrate for more or less structural stability, or may allow for control of the rate delivery of molecules encapsulated in the hydrophobic core of the nanofibers or adsorbed on their hydrophilic surfaces.

In another embodiment, the peptide element of the peptide amphiphiles are preferably carboxyl terminated, so that once assembled into fibers, these fibers may participate in further or carbamide bonding to functionalize a metal surface or some other type of surface.

Another embodiment of the present invention is a method for making and utilizing self assembled peptide amphiphile nanofiber coated surfaces as temporary scaffolding for cellular growth and implantation.

Another embodiment of the invention is biodegradable, non-toxic self assembled peptide amphiphile nanofiber coated surfaces and scaffolds which can be utilized for cell growth, both in vitro and in vivo as support structures for endothelial cells, organ tissue, and nerve cells immediately following implantation.

Another embodiment the present invention is a method for configuring and constructing biodegradable self assembled peptide amphiphile nanofiber coated surfaces and scaffolds that provide a support for cell growth but allow and enhance vascularization of the growing cell mass following implantation of the surface or scaffold.

Another embodiment of the invention is self assembled peptide amphiphile nanofiber coated surfaces with domains of chemically different self assembled peptide amphiphile coatings so that more than one type of cell can be grown or the growth rate of cells on the substrate can be controlled.

Another embodiment of the present invention is an implantable self assembled peptide amphiphile nanofiber coated stent that is adapted to promote angiogenesis within a blood vessel or other tubular lumen into which the stent is implanted.

Another embodiment of the present invention is an implantable self assembled peptide amphiphile nanofiber coated stent that is adapted to enhance or stimulate neointimal infiltration, but with organization of the infiltrating cells so as to result in neovascularization.

Another embodiment of the present invention is an implantable self assembled peptide amphiphile nanofiber coated stent that is adapted to promote ingrowth of living cells, when cultured in a cell-rich in vitro environment or when implanted within a tubular body lumen, such as a blood vessel.

Another embodiment of the present invention is a self assembled peptide amphiphile nanofiber coated stent populated with living cells growing throughout pores and/or other surface features designed to promote growth of the cells into an organized cellular structure when the cell is implanted into a tubular body lumen or organ.

Another embodiment of the present invention 1 is a self assembled peptide amphiphile nanofiber coated stent wherein the living cells are genetically engineered to produce a therapeutic bioactive agent to be released from the coating nanofibers, such as one selected to inhibit or promote angiogenesis or proliferation of intima within the implanted stent.

Another embodiment of the present invention provides a technique whereby functional cells from a needed organ are grown on a scaffolding coated with nanofibers comprised of self assembled peptide amphiphiles. The coated scaffold may be used in vivo or in vitro-using cell culture techniques followed by transfer of the scaffold-cell composite into a patient at a site appropriate for attachment, growth and function, after attachment and equilibration. Nutrients and growth factors are supplied during cell culture allowing for attachment, survival or growth as needed. Alternatively nutrients and growth factors are encapsulated by the self assembled peptide amphiphile micelles.

The use of self assembled peptide amphiphile nanofiber coated scaffold or surgical device to grow cells and tissue is advantageous because its high surface area permits a large number of sites for cell adhesion and growth. The fibrous nature of the coating allows nutrients to penetrate the growing cell culture by diffusion until new blood vessels form. For an organ to be constructed in tissue culture and subsequently successfully implanted, the matrices must have sufficient surface area and exposure to nutrients such that cellular growth and differentiation can occur prior to the growth of blood vessels following implantation. After implantation, the configuration must allow for diffusion of nutrients and waste products and for continued blood vessel ingrowth as cell proliferation occurs. Nanofiber gels and micelles prepared from self assembled peptide amphiphiles have a high surface area and are ideally suited for providing a good growth environment.

DESCRIPTION OF THE DRAWINGS

In part, other aspects, features, benefits and advantages of the embodiments of the present invention will be apparent with regard to the following description, appended claims and accompanying drawings where:

FIGS. 11A-C Scanning electron micrograph digital images of preosteoblastic mouse calvaria cells spreading on pLys-CP coating on titanium foil after (A) 1 day, (B) 4 days and (C) 7 days of culture.

DETAILED DESCRIPTION

Figure 1B:
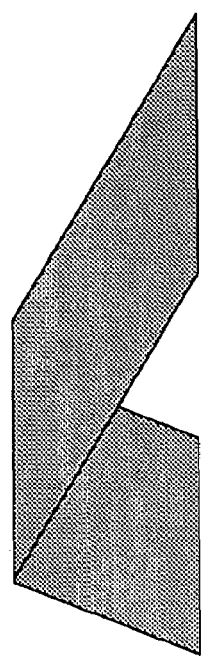
FIG. 1B the foil sample schematic used, protecting foil underside from precipitate settling out of solution.

Embodiments of the present invention relates generally to bonding self assembled peptide amphiphile nanofiber or micelle coatings on secondary substrates to be placed within the body of a mammal. Such substrates may include porous scaffolds, electrodes, and surgical implants like stents. The self assembled peptide amphiphile nanofiber coating is comprised of peptide amphiphiles having amino acids promoting the growth and adhesion of cells and tissues to the substrate. Preferably, the peptide-amphiphiles' design and function is patterned after naturally occurring structures like proteins, cells, and collagen. The substrates may be used outside the body to grow cells on the substrate and then placed within the body; alternatively the coated substrates may be placed directly within the body and promote the growth of cells or tissue. The nanofibers or micelles may also encapsulate active compounds to promote the growth of such cells and tissues. Before the present compositions and methods are described, it is to be understood that this invention is not limited to the particular molecules, compositions, methodologies or protocols described, as these may vary. It is also to be understood that the terminology used in the description is for the purpose of describing the particular versions or embodiments only, and is not intended to limit the scope of the present invention which will be limited only by the appended claims.

It must also be noted that as used herein and in the appended claims, the singular forms "a", "an", and "the" include plural reference unless the context clearly dictates otherwise. Thus, for example, reference to a "cell" is a reference to one or more cells and equivalents thereof known to those skilled in the art, and so forth. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference. Nothing herein is to be construed as an admission that the invention is not entitled to antedate such disclosure by virtue of prior invention.

Before the present compositions and methods are described, it is to be understood that this invention is not limited to the particular molecules, compositions, methodologies or protocols described, as these may vary. It is also to be understood that the terminology used in the description is for the purpose of describing the particular versions or embodiments only, and is not intended to limit the scope of the present invention which will be limited only by the appended claims.

Coupling agents, used for the binding of the peptide amphiphile with the secondary surface, may be by the physisorption, chemisorption or covalent grafting of the peptide amphiphile, and or their self assembled spherical micelles or nanofibers with the secondary surfaces. Examples of coupling agent binding include but are not limited to ionic bonds, coordination bonds, chelation bonds, metal sulfide bonds, amide or ester bonds between the self-assembled nanofibers or micelles and the surface. Such a binding scheme is expected to provide a stable mechanism for attachment of peptidic nanostructures to secondary surface materials including but are not limited to, other self assembled peptide amphiphiles, the surfaces of cells, proteins, cartilage, metals, alloys, ceramics, glasses, minerals, polymers, and biocompatible implants such as stents, scaffolds, electrodes, and orthodontics. This attachment would allow a peptide containing micelle to be robustly stabilized on a material surface. In one embodiment the peptide amphiphile nanofibers contain a carboxyl-rich peptide sequence are used. Such peptide amphiphiles are bound to surfaces displaying free amines.

In one embodiment of a coupling, peptide amphiphile nanofibers are bonded to an amino-silanized metal surface like titanium or a metal alloy. The chemicals and methods used to form the amide linkages between peptide amphiphiles and a surface having such an amino-silane surface group are similar to those used in peptide synthesis (Knorr, et al; Fields et al; Wellings, et al.; the methods of which are incorporated herein by reference in their entirety) The reaction is conducted in a polar organic solvent, for example but not limited to N,N-dimethylformamide (DMF) or N-methylpyrrolidinone (NMP), both of which are capable of solublizing amino acids. The method also involves utilizing a compound such as O-Benzotriazole-N,N,N',N'-tetramethyluronium-hexafluoro-phosphate (HBTU) as a catalyst to increase the reactivity of carboxylic acid functional groups on the peptide amphiphile. Other peptide coupling agents or activators include but are not limited to: dicyclohexylcarbodiimide (DCC); O-(7-azabenzotriazol-1-yl)-1,1,3-,3-tetramethyluronium hexafluorophosphate (HATU); and benzotriazol-1-yl-ox ytripynolidinophosphonium hexafluorophosphate (Py-BOP). These reactive acid groups then undergo a reaction with free amines, in the presence of the basic proton sink, diisopropylethylamine (DIEA), eventually leading to the final elimination reaction to remove the HBTU and water, leaving behind a stable amide linkage.

Metal and metal alloy oxide surfaces may be modified with various amino-silanes for biological applications. These modifications may be used for attachment of different peptide amphiphiles or self assembled micelles to the oxide surfaces. For example, incubation of $TiO_2$-passivated titanium surfaces with the desired amino-silanes produces Ti—O—Si bonds at the oxide-solvent interface, covalently linking the aminosilane to the oxidized metal surface. This arrangement leaves a free amine exposed for standard amide-couple reactions with a suitable peptide amphiphile; the free amines tethered to the metal surface and the exposed carboxylic acids on the nanofibers to form an amide bond, covalently linking the fibers to the silainzed Ti surface.

In an embodiment of the present invention, a standard amide coupling reaction is applied to a pre-assembled, cross-linked peptide nanofiber. For example, a dilute solution of peptide amphiphile molecules, meeting the compositional requirements described above and maintained in a solution of a mild reducing agent (such as dithiolthreitol (DTT)), is self-assembled in acidic conditions to form peptide nanofibers. These nanofibers are crosslinked by the addition of a non-destructive oxidizer, such as iodine, forming stable intermolecular, intrafiber disulfide bonds. The resulting suspension of these fibers is dialyzed against water to remove all reducing or oxidizing agents (such as DTT and iodine). This dialyzed suspension of cross-linked fibers is then lyophilized and the dried fibers are re-suspended by vigorous agitation and ultra-sonication in a peptide-solublizing polar organic solvent, such as DMIF or NMP. The covalent cross-linking of the fibers stabilizes them in the non-aqueous environment.

Substrates are preferably biocompatible materials and may include but are not limited to commercially pure titanium, titanium alloys, or other metals such as chromium and its alloys, stainless steels like Hastalloy, 316 L, and 304 and presenting an oxide surface may be cleaned ultrasonically in an organic non-polar solvent, an organic polar solvent, and finally distilled water. The cleaned metal or alloy is may then etched in a such as mild hydrofluoric acid, nitric acid solution before re-passivation in nitric acid. Passivated substrate samples are rinsed thoroughly in distilled water and dried. Cleaned, passivated samples are then dehydrated by vacuum desiccation and stored at temperatures above room temperature before amino-silanization. Dry, passivated surfaces introduced to a dilute solution of an amino silane, such as aminopropyltriethoxysilane (APTES) in an anhydrous hydrophobic organic solvent, such as toluene, under nitrogen. Amino-silanized metal substrates are then rinsed thoroughly in an organic non-polar solvent, an organic polar solvent, and finally water before annealing at elevated temperature (e.g.

100° C.) under an inert gas. Substrates may also include but are not limited to biocompatible polymers, or various carbides, borides, and nitrides.

In another embodiment of a coupling agent metals having an oxidized surface are immersed in a solution of $CaCl_2$ and $Na_2HPO_4$, or other similar salts, to pre-seed the surface with calcium phosphate. This pre-seeded substrate is then immersed in a solution containing poly(L-lysine), $CaCl_2$, and $Na_2HPO_4$. The samples are rinsed with water and dried at room temperature. The poly(L-lysine) is incorporated into the resulting mineral phase of the newly formed calcium phosphate coating, and the free amines from the side-chains of the poly(L-lysine) are displayed on the textured coating surfaces. Other minerals may be used in place of calcium phosphate, for example but not limited to calcium carbonate. A number of different amines or polyamines, organic acids or polyorganic acids may be incorporated into the mineral. Any such amine or polyamine (including poly(L-lysine) may be physisorbed, chemisorbed, or covalently grafted onto passivated metal surfaces. Reference is made to later discussion, FIGS. 1-11 and examples 2-5, below. Amino acids and polyamino acid may also be used to treat the surfaces, as disclosed in U.S. Pat. No. 6,051,272 and incorporated herein in its entirety. It may also be possible to do a binding reaction in the absence of air, whereby a sulfur containing compound, like a cysteine, could be used oxidize a metal surface (whose oxide has been removed), forming a direct bond there. This would be a way to directly couple an amino acid, peptide, protein, or poly (amino acid) to a metal.

Secondary surfaces may be terminated with carboxylic acid groups as coupling agents. For example, 3-mercaptopropionic acid may be used to derivatize some metal surfaces with carboxylic acid groups. Alternatively, polymeric materials like polyethylene may be oxidized to provide a carboxylic acid terminated surface. These carboxylic acid terminated surfaces may be reacted with amine or hydroxyl bearing peptide amphiphiles and bind them to the secondary surface.

In another embodiment, for example, two sets of peptide amphiphile fibers could be independently self-assembled, crosslinked, dialyzed, lyophilized, and suspended in solvent. One set of nanofibers would be rich in carboxyl functional groups, while the other could be rich with free amines. If combined in the presence of HBTU and DIEA, these separate nanofibers may be bound together. Such an application might be useful in combining different amino acid sequences which might work well in concert with one-another. This sort of application might furthermore be combined with metal surface modifications, where one peptide amphiphile fiber type could be attached to the surface as described above, and the complementary fiber type could be linked to those attached fibers, forming a sort of double-layer of different covalently-linked nanofibers. Another embodiment of the methods described above involves using a metal surface other than titanium. It is reasonable to expect that the amino-silanization could be performed on any surface presenting a suitable oxide, including but not limited to titanium alloys, silicon, tantalum, chromium, and chromium-containing alloys (including stainless steel). Various ceramic secondary substrates would also be useful in this regard including alumina and various forms of silicon dioxide.

The peptide-amphiphiles and their self assembled nanofibers may promote adhesion and growth of cells on their surfaces. For example, the cell adhesion ligand RGD has been found in other contexts to play an important role in integrin-mediated cell adhesion. Peptide-amphiphile species with acidic amino acids and an amino acid with the RGD ligand could be used to mediate cell adhesion to the peptide-amphiphiles, their self assembled nanofibers or micelles, or nanofiber gels. The amino acid sequence SEQ ID NO:2 IKVAV has been identified in other contexts as important for neuron growth and development. Accordingly, peptide-amphiphile species with acidic amino acids and the SEQ ID NO:2 IKVAV sequence could be used in the practice of embodiments of this invention to mediate neuron growth to the peptide-amphiphiles, their self assembled nanofibers, micelles, or nanofiber gels. The amino acid sequence SEQ ID NO:1 YIGSR has been identified in other contexts as important in for promoting cell-substrate adhesion among nerve cells and may also play a role in axon guidance. Accordingly, peptide-amphiphile species with acidic amino acids and the SEQ ID NO:1 YIGSR sequence could be used in embodiments of the practice of this invention to promote cell-substrate adhesion among nerve cells to the peptide-amphiphiles, their self assembled nanofibers, micelles, or their nanofiber gels. For example in dentin, the phosphophoryn protein family contains numerous repeats of the amino acid sequences Asp-Ser(P)-Ser(P) and Ser(P)-Asp-Ser(P). These massively phosphorylated proteins are suspected to play an important role in hydroxyapatite mineralization. Accordingly, phosphoserine residues can be incorporated into the peptide sequence which, after self assembly, allows the fiber to display a highly phosphorylated surface similar to that presented by a long peptide segment. Such a peptide, in part, captures the repetitive organization of phosphate groups found in phosphophoryn proteins.

Various C or N terminated peptide-amphiphiles useful in the practice of embodiments of this invention may be prepared using standard fluorenylmethoxycarbonyl chemistry on automated peptide synthesizers. Peptide amphiphiles solutions may be formed into nanofibers by changing the pH, addition of salts, or by addition of charged or chelated peptide amphiphiles. Representative peptide amphiphiles which may be used in embodiments of this invention are shown, Tables 1-3, below. The formation of peptide amphiphiles, like those listed in Tables 1-3, into nanofibers are described by Hartgerink, et al., Science, 294, 1683-1688, (2001), and Hartgerink et al., PNAS, 99, 5133-5138, (2002); the contents of which are included by reference in their entirety. Other peptide amphiphile may be prepared as would be known to those skilled in the art, using known procedures and synthetic techniques or straight-forward modifications thereof depending upon a desired amphiphile composition or peptide sequence. For example, the peptide amphiphiles provided herein can be prepared, characterized and/or assembled as described in co-pending application Ser. No. 10/294,114 filed Nov. 14, 2002 and Ser. No. 10/368,517 filed Feb. 18, 2003, each of which is incorporated herein by reference in its entirety. Without limitation, the peptide amphiphiles of such incorporated applications, as described in the corresponding tables, figures and examples thereof, can also be used in conjunction with the composites and methods of this invention.

TABLE 1

| PA | N-terminus | Peptide (N to C) | C-terminus |
|---|---|---|---|
| 1 | C16 | SEQ ID NO:4 CCCCGGGS(P)RGD | H |
| 2 | C16 | SEQ ID NO:5 CCCCGGGS(P) | H |
| 3 | C12 | SEQ ID NO:4 CCCCGGGS(P)RGD | H |

TABLE 1-continued

| PA | N-terminus | Peptide (N to C) | C-terminus |
|----|------------|------------------|------------|
| 4  | C10        | SEQ ID NO:4 CCCCGGGS(P)RGD | H |
| 5  | C14        | SEQ ID NO:4 CCCCGGGS(P)RGD | H |
| 6  | C10        | SEQ ID NO:6 GGGS(P)RGD | H |
| 7  | C16        | SEQ ID NO:6 GGGS(P)RGD | H |
| 8  | C16        | SEQ ID NO:7 AAAAGGGS(P)RGD | H |
| 9  | C10        | SEQ ID NO:7 AAAAGGGS(P)RGD | H |
| 10 | C16        | SEQ ID NO:8 CCCCGGGS(P)KGE | H |
| 11 | C10        | SEQ ID NO:9 AAAAGGGS(P)KGE | H |
| 12 | C16        | SEQ ID NO:9 AAAAGGGS(P)KGE | H |
| 13 | C22        | SEQ ID NO:4 CCCCGGGS(P)RGD | H |
| 14 | C16        | SEQ ID NO:10 CCCCGGGSRGD | H |
| 15 | C16        | SEQ ID NO:11 CCCCGGGEIKVAV | H |
| 16 | C16        | SEQ ID NO:12 CCCCGGGS(P)RGDS | H |

Depending upon desired cell or tissue growth, a phosphorylated moiety may not be required. As discussed above, cellular adhesion or interaction is promoted by a particular sequence of the peptide components. With reference to PA's 10-12 and 15, a non-RGD sequence can be utilized depending upon cellular target. In particular, the SEQ ID NO:2 IKVAV sequence has been identified in other contexts as important for neuron growth and development. Accordingly, the amphiphile compositions of this invention can include a peptide component having such a sequence for corresponding use. Lastly, with respect to Table 1, it is noted that several PA compositions do not include cysteine residues. While cysteine amino acids can be used to enhance intermolecular nanofiber stability, it is not required for self assembly of micelles or nanofibers, nor is it necessary for binding of peptide amphiphile or their micelles to secondary surfaces. In a preferred embodiment, cysteine amino acids are present to stabilize the self assembled micelles or nanofibers during the peptide coupling reactions.

Triblock bola amphiphiles which self assemble into fibers and micelles may also be useful in the practice of this invention.

In one embodiment, an aqueous solution of one or more of the amphiphile compositions described herein, and a factor or reagent sufficient to induce gelation under physiological conditions is added. Such gelation and/or self-assembly of various PA compositions into nanofibers can be achieved under substantially neutral pH conditions through drying, introduction of a multivalent, divalent or higher valency metal ion, chelation, and/or the combination of differently charged amphiphiles.

TABLE 2

| PA | N-terminus | Peptide (N to C) | C-terminus | Net Charge at pH7 |
|----|------------|------------------|------------|-------------------|
| 17 | C16 | SEQ ID NO:4 CCCCGGGS(P)RGD | COOH | -3 |
| 18 | C16 | SEQ ID NO:7 AAAAGGGS(P)RGD | COOH | -3 |
| 19 | C10 | SEQ ID NO:7 AAAAGGGS(P)RGD | COOH | -3 |
| 20 | C16 | SEQ ID NO:10 CCCCGGGSRGD | COOH | -1 |
| 21 | C16 | SEQ ID NO:11 CCCCGGGEIKVAV | COOH | -1 |
| 22 | C16 | SEQ ID NO:13 CCCCGGGKIKVAV | $COOH_2$ | +1 |

The electrode, stent, scaffold, or surgical device or other secondary surface may be coated with peptide amphiphile containing nanofibers or micelles in various ways. The secondary surface, comprising amine or carboxylic acid groups on its surface, may be placed in a suspension of previously self assembled peptide amphiphiles nanofibers or micelles that have been dialyzed. Alternatively, a small sample of a nanofiber gel may be smeared onto the electrode, stent, scaffold, or surgical device for a period of time and then washed with solvent to remove excess gel. A solution of the peptide amphiphile may also be sprayed or aerosolized onto the substrate to coat it and then exposed to an acidic vapor to form the nanofibers or micelles. Alternatively, the electrode, stent, scaffold, surgical device is placed in a volume of the peptide amphiphile, removed, and exposed to acid vapors, dipped in a salt solution, or peptide amphiphile containing solution to form the nanofibers. Coatings onto the secondary substrates may be made with a combination of these methods and may be repeated as necessary to ensure sufficient coating for the intended use. The coated substrates are then treated with, for example, HBTU and DIEA in NMP to couple the peptide amphiphiles to the secondary surface.

Exposure of such coated substrates having cysteine amino acids in the nanofiber to oxidants like oxygen, iodine, hydrogen peroxide, or ozone may be useful for covalent capture and formation of disulfide bonds. Such coating may provide thermal stability to nanofibers coated onto scaffolds and devices which may be subsequently heated to enhance cell growth rates.

Other compounds' may be incorporated into or encapsulated by the self assembled peptide amphiphile cores which make up the coating. These compounds may enhance in-growth of blood vessels following implantation or delivery of the nanofiber coated secondary substrate to the body. Nutrients, growth factors, inducers of differentiation or de-differentiation, immunomodulators, inhibitors of inflammation, biologically active compounds which enhance or allow in-growth of the lymphatic network or nerve fibers, and drugs can also be incorporated into the self assembled peptide amphiphile nanofiber coating. A number of agents that affect cell proliferation have been tested as pharmacological treatments for stenosis and restenosis in an attempt to slow or inhibit proliferation of smooth muscle cells. These compositions may include heparin, coumarin, aspirin, fish oils, calcium antagonists, steroids, and prostacyclin. Such agents may be systemically encapsulated in fiber or may additionally be delivered on a more local basis using a drug delivery catheter. In particular, biodegradable peptide amphiphile nanofiber matrices containing one or more pharmaceuticals may be implanted at a treatment site. As the nanofiber degrades, the pharmaceutical is released directly at the treatment site.

A number of cells may be grown on the electrode, stent, scaffold, surgical device having a coating of the self assembled peptide amphiphile nanofibers. The scaffold or surgical implant coating is comprised of self assembled peptide amphiphiles with peptides chosen for optimal growth of that particular type of cell. For example peptide amphiphiles with the RGD, SEQ ID NO:2 IKVAV, KGE, SEQ ID NO:14 RGDS peptide sequences, and self assembled nanofibers comprised of them or combinations of them may be optimal for cell growth.

Examples of cells which are suitable for implantation include but are not limited to hepatocytes and bile duct cells, islet cells of the pancreas, parathyroid cells, thyroid cells, cells of the adrenal-hypothalmic-pituitary axis including hormone-producing gonadal cells, epithelial cells, nerve cells, heart muscle cells, blood vessel cells, lymphatic vessel cells, kidney cells, intestinal cells, cells forming bone, cells forming cartilage, cells forming smooth muscle and cells forming skeletal muscle.

The secondary surface should be shaped to maximize surface area to allow adequate diffusion of nutrients and growth factors to the cells attached to the self assembled peptide amphiphiles. Adequate diffusion through densely packed cells can occur in the range of approximately 200 to 300 microns under conditions similar to those which occur in the body, wherein nutrients and oxygen diffuse from blood vessels into the surrounding tissue.

In the present invention, the cells may initially be cultured using techniques known to those skilled in the art of tissue culture. However, once the cells have begun to grow and cover the self assembled peptide amphiphile coated electrode, stent, scaffold or surgical device, they are implanted in a patient at a site appropriate for attachment, growth and function. One of the advantages of a biodegradable self assembled peptide amphiphilic coating on a scaffold is that angiogenic compounds may be incorporated directly into the self assembled peptide amphiphile nanofibers so that they are slowly released as the nanofiber coating degrades in vivo. As the cell-self assembled peptide amphiphile nanofiber structure is vascularized and the structure degrades, the cells will differentiate according to their inherent characteristics.

A secondary structure, for example a porous scaffold, may be coated with self assembled peptide amphiphile nanofiber composition may be prepared in vitro for implanting to produce functional organ tissue in vivo. The scaffold is a three-dimensional structure coated with self assembled peptide amphiphile nanofibers which may be biocompatible, biodegradable, or non-biodegradable. Examples of such scaffolds include porous ceramic materials available from Porex Corporation, Fairburn, Ga.; Mykrolis Corporation Billerica, Mass.; and Robocasting, Albuquerque, N. Mex. The nanofibers or micelles have peptide amphiphiles with amino acid which are capable of inducing and supporting cell growth and attachment. Cells derived from various tissues are attached in vitro to the surface of the fibers uniformly throughout the nanofiber coated scaffold in an amount effective to produce functional tissue, preferably in vivo. Alternatively, the tissue or cells are grown on the self assembled peptide amphiphile nanofiber coated scaffold in a nutrient solution in vitro to form the cell-scaffold composition which is implanted in a patient at a location having adequate vascularization to allow growth of blood vessels into the cell-scaffold composition. Growth factors, compounds stimulating angiogenesis and immunomodulators may be bound to the nanofibers coating the cell-scaffold composition. Combinations of peptide amphiphile nanofibers cell-scaffold compositions containing different cell populations may be implanted.

If appropriate, immunosuppressant drugs may be injected at the site of the secondary surface or scaffold, implant or electrode. Alternatively, the immunosuppressant drugs may be incorporated into the self assembled nanofibers or micelles coating the scaffold or surgical implant.

Under certain conditions, the body naturally produces another drug that has an influence on cell apoptosis among its many effects. As is explained in U.S. Pat. No. 5,759,836 to Amin et al., which is incorporated herein by reference in its entirety, nitric oxide (NO) is produced by an inducible enzyme, nitric oxide synthase, which belongs to a family of proteins beneficial to arterial homeostasis. However, the effect of nitric oxide in the regulation of apoptosis is complex. A pro-apoptotic effect seems to be linked to pathophysiological conditions wherein high amounts of NO are produced by the inducible nitric oxide synthase. By contrast, an anti-apoptotic effect results from the continuous, low level release of endothelial NO, which inhibits apoptosis and is believed to contribute to the anti-atherosclerotic function of NO. Dimmeler in "Nitric Oxide and Apoptosis: Another Paradigm For The Double-Edged Role of Nitric Oxide" (Nitric Oxide 14: 275-281,1997) discusses the pro- and anti-apoptotic effects of nitric oxide. Self assembled peptide amphiphile nanofibers encapsulating nitric oxide synthase may be used to coat implanted surgical devices like stents.

In one embodiment, the scaffold or surgical implant is coated with a nanofiber comprised of peptide amphiphiles from Table 1 and Table 2. The stent, scaffold, electrode, or surgical device can be formed of any suitable substance, such as is known in the art, that can be adapted (e.g., molded, stamped, woven, etc.) to contain the surface features required. Preferred scaffold and stents are formed of a material comprising metallic, ceramic, or polymeric fibers uniformly laid to form a three-dimensional non-woven matrix and sintered to form a labyrinth structure exhibiting high porosity, typically in a range from about 50 percent to about 85 percent, preferably at least about 70 percent. The scaffold fibers typically have a diameter in the range from about 1 micron to 25 microns. The average effective pore size in a secondary structure may be such that cellular in-growth into the pores and interstices is enhanced, for example having an average diameter in the range from about 1 microns to about 100 microns.

The substrate surfaces (i.e., electrode, surgical device or implant, stent, or scaffold) coated with the self assembled peptide amphiphile nanofiber may be formed from a biocompatible materials comprising metal and alloys, such as stainless steel, tantalum, nitinol, elgiloy; ceramics like sapphire or silicon nitride, polymers like polytetrafluoroethylene, PFA, or polyethylene; or combinations of these materials. The scaffold and or the nanofiber may be biodegradable or non-biodegradable. The scaffold or stent may be made entirely of a self supporting and molded nanofiber gel; for suitable applications the nanofiber gel may be degradable. The coated scaffold or implant may be coated with extracellular components such as collagen, fibronectin, laminin, and complex mixtures of these. A non-degradable material is particularly useful when the cells are grown in culture for purposes other than transplantation since the preferred matrix structure allows for a higher immobilized cell density than can normally be achieved where nutrients are supplied solely by diffusion. The stent, scaffold, or surgical implant may be formed of a biocompatible non porous polymer or a polymer made porous by incorporating dissolvable salt particles prior to curing thereof and then dissolving away the salt particles to leave voids and interstices therein. The polymer may be biostable or bioabsorbable, such as a number of medical grade plastics, including but not limited to, high-density polyethylene, polypropylene, polyurethane, polysulfone, nylon and polytetra-fluoroethylene. A porous polymer stent body can be made having pores with an average diameter in the range from about 30 microns to about 65 microns, by procedures known in the art.

The biological signals presented by the self assembled peptide amphiphile nanofiber must be appropriate for the kind of cell or tissue to be implanted, as well as to maximize the cell's exposure to the surrounding environment. It must also be designed to enhance the cell's ability to promote blood vessel formation and scaffold or tissue infiltration.

In one embodiment of the invention, a stent is coated with a self assembled peptide amphiphile nanofiber. The coated stent body may be formed from a biocompatible polymer or a biocompatible metal with the surface features stamped or molded into the surface. Appropriate flexibility should be provided to the stent for manipulation in the body as known to those skilled in the art. For example, the invention stent body can be formed of a porous biocompatible material, such as a porous matrix of sintered metal fibers or a polymer wherein the pores are sized to promote the organization of in-growing cells therein. The self assembled peptide amphiphile nanofibers are applied to the surfaces of the polymer or metals and or throughout the pores.

The self assembled peptide amphiphile nanofibers coated stent body is designed to promote infiltration and population of the stent by living cells, when the coated stent is cultured in a cell-rich medium or when the coated stent is implanted into a blood vessel or other tubular body lumen in a subject such as a mammal. Further the surface features in the coated stent body are selected to cause the living cells that infiltrate and populate the self assembled peptide amphiphile nanofibers coated stent to undergo cell growth in a specific pattern determined by the placing and dimensions of the surface features of the coated stent body. One example of such pre-determined cell growth pattern is angiogenesis and/or neovascularization.

A self assembled peptide amphiphile nanofiber coated surface (i.e. stent., electrode, or scaffold) penetrated with pores may be readily populated with living cells if the coated surface is cultured in a cell-rich medium (e.g., $6\text{-}10 \times 10^4$ endothelial cells in 0.8 ml culture medium) under cell-culturing conditions, as is known in the art. Such a cell culturing procedure is described, for example, in D. A. Dichek, et al., supra, which is incorporated herein by reference in its entirety. A self assembled peptide amphiphile nanofiber coated surface or substrate having such pores may readily be infiltrated by cells from the surrounding cellular environment so as to create an organized cellular structure similar to that of the surrounding bodily environment.

The surface of the substrate (ie electrode, scaffold, stent, or surgical device) may comprise a layer of a biocompatible substance that expands or thickens in an aqueous environment to assume a three-dimensional form, wherein the layer covers at least a portion of the surface of the substrate. For example, the biocompatible substance can be or comprise one or more hydrogels, such that the hydrogel layer expands as it absorbs water upon contact with an aqueous environment to create a porous three dimensional layer. Alternatively, the hydrogel can further comprise peptide amphiphiles or self assembled peptide amphiphiles. In the case of a stent, the expansion of the hydrogel and the peptide nanofibers supports the surrounding tissue and provide for sites of endothelial cell growth.

Autologous cells naturally invade the self assembled peptide amphiphile nanofiber coated substrates (scaffold, stent, electrode, or surgical device) following placement in at a site in need thereof in a body of a host subject and spontaneously generate an organized cellular structure that varies depending upon the cellular makeup of the bodily site into which the substrate is implanted. For example, endothelial or other suitable cells may be made to invade a self assembled peptide amphiphile coated stent in a cell culture lab to create a living nanofiber coated stent prior to implant, using methods known in the art. For example, a living peptide amphiphile nanofiber coated substrate can be obtained according to the invention wherein the peptide amphiphile nanofiber coated substrate is populated with live cells selected from endothelial cells, smooth muscle cells, leukocytes, monocytes, epithelial cells, polymorphonuclear leukocytes, lymphocytes, basophils, fibroblasts, stem cells, epithelial cells, eosinophils, and the like, and combinations of any two or more thereof.

A typical intravascular stent may have an outer diameter in a range of from about 2.0 mm to about 6.0 mm and a wall thickness in a range from about 0.1 mm to about 12 mm, for example about 0.1 mm to about 1.0 mm. The particular size, of course, depends on the anatomy where the stent is to be implanted. The stent may be expandable, for example, such designs are disclosed for example in U.S. Pat. No. 5,059,211, incorporated herein by reference, which discloses an expandable stent made of a porous polymeric material. The stent may be delivered by a catheter.

An advantage of the present method is that it provides a means for selective transplantation of parenchymal cells which possess the necessary biologic function, without transplantation of passenger leucocytes and antigen-presenting cells. The result is a greatly reduced risk of rejection of tissue without the use of drugs. The present invention has another advantage over other means for treating organ function loss since the cells may be manipulated while in culture to introduce new genes to make absent protein products or they may be modified to repress antigen expression on the cell surfaces so that immuno-suppression is not needed when cells of the same HLA tissue type are not available.

The self assembled peptide amphiphile nanofiber coated substrates (stent, electrode, scaffold) of the present invention can be implanted using any surgical technique known in the art as is dictated by the particular body organ to be treated.

The living cells in-growing in the self assembled peptide amphiphile nanofiber coated secondary substrates in embodiments of the present invention treatment method may encapsulate beneficial bioactive agents. For example the nanofibers of the coating may encapsulate autologous cells of the subject into which the substrate is implanted, cells seeded into the substrate prior to implant that naturally produce the desired bioactive agent, or cells that are genetically modified to produce a desired bioactive agent. Living cells that naturally produce one or more bioactive agents useful in practice of the invention methods include endothelial cells, smooth muscle cells, leukocytes, monocytes, polymorphonuclear leukocytes, lymphocytes, basophils, fibroblasts, stem cells, epithelial cells, eosinophils, and the like, and suitable combinations thereof. Such cells can be either donor or autologous cells.

Alternatively, the nanofiber encapsulated cells or compound in the coating used in embodiments of the invention treatment method can be engineered to express and release a bioactive agent in response to delivery of a suitable compound to the patient such that the recombinant gene products are delivered to a site implanted with a coated secondary substrate.

Nerve growth may also be promoted using, for example, an electrode or other surface coated with self assembled peptide amphiphile nanofibers containing an appropriate nerve cell growth peptide sequence. Following growth of the nerve along the length of the fiber, the structure is implanted at the appropriate location extending from a nerve source to the area in which nerve function is desired.

In a variation of the method using a scaffold or surgical implant with a single coating of nanofiber for attachment of one or more cell lines, the coated scaffolding is constructed with coatings of different self assembled nanofibers such that initial cell attachment and growth occur separately for each population. A unitary scaffolding may also be formed of different materials to optimize attachment of various types of cells. Attachment is a function of both the cell and structure composition. For example, coating a surgical implant with nanofibers comprised of collagen like peptide amphiphiles with phosphorylated amino acids and the RGD peptide sequence can increase adhesion of cells. In another example, self assembled peptide amphiphile nanofibers (with phosphorylated amino acids and the RGD peptide sequence) may be coated onto a biodegradable scaffold After implantation and degradation of the scaffold, the blood vessel cells form the appropriate connections for delivery of the blood to the desired locations. Ducts for excretion by the organ may be constructed in an analogous manner, always taking advantage of the inherent behavior of the cells. In-growth of the lymphatic network and nerve fibers may also be encouraged.

Optionally, the cells for growth on a nanofiber coated surface or scaffold can be obtained from a donor or from the host subject, treated, and cultured in vitro on the nanofiber coated scaffold, and then reintroduced into the subject. In a presently preferred embodiment, the transplanted cells are "autologous" with respect to the subject, meaning that the donor and recipient of the cells are one and the same.

Bioactive agents suitable for delivery by encapsulation in self assembled peptide amphiphile nanofibers coating a scaffold, electrode, stent, or surgical device according to embodiments of the present invention methods include those bioactive agents which the mammalian body utilizes to stimulate angiogenesis, including those which regulate capillary formation in wounds and attract smooth muscle to coat and support the capillaries. Examples of such bioactive agents which may be encapsulated in nanofibers of the coating include vascular endothelial growth factor (VEGF), fibroblast growth factors (FGFs), particularly FGF-1, angiopoietin 1, thrombin, and the like. Additional examples of bioactive agents suitable for delivery according to the invention methods include anti-proliferative, anti-restenotic or apoptotic agents, such as platelet-derived growth factor-A (PDGF-A), transforming growth factor beta (TGF-β), nuclear factor-K β (NF-Kp), an inducible redox-controlled transcription factor, and the like.

The method described in this disclosure may be used to deliver specific biofunctional peptide sequences to a biomaterial or other surface which may activate or modify various biological responses. Such responses may include selective binding to the peptides bonded to the substrate or biomaterial, improved or increased cellular proliferation, or even selective degradation of a bioscaffold. This scheme may even have applications for drug delivery. Drugs or other therapeutic molecules may either be incorporated within the stable micellar assembly, or they may be chemically bound to the nanofiber surface. It is expected that there will be a broad range of possibilities for application of this methodology in fields including bone repair, dental repair, and cardiovascular stent modification.

As mentioned above, the methods and compositions of the present invention can also provide for growth of nanocrystalline or poorly crystalline phases of normally crystalline materials in a monolithic form or more preferably as a coating on a substrate. The nanocrystalline phases are formed by contacting a substrate pre-seeded with a mineral on its surfaces with a solution including the dissolved crystalline material and an additive which is incorporated into the crystalline material of the coating and which reduces the size of the crystalline domains of the material. The additive provides for nanocrystalline morphology and also provide additional reactive functionalities for chemically reacting the coating with other molecules. The compositions provide increased surface coverage of substrates with the coating, especially those substrates with small features such as pores and channels. The coated substrates may be used for in vitro or in vivo cell growth on the nanocrystalline coated substrate material.

The composition of the present invention is preferably a solution which includes but is not limited to an organic additive such as a polyamine or an acid addition salt thereof and dissolved components of a material. The components of the crystalline material may be molecular or ionic. The solution should be able to dissolve the crystalline components as well as the additive. The solution may be an aqueous solution, an organic solution, or a combination thereof and may include organic liquids such as ethanol, amines and their acid addition salts, amino acids, surfactants, as well as soluble constituents of the crystalline material.

The organic additive in the composition which frustrates the crystal growth and results in the nanocrystalline phase of the normally crystalline material may include a polyamine, acid or their salts. The additive may be chosen to control its reactivity towards degradation in the coating. Other additives may be poly(amino acids) or other polymers with side groups such as carboxylic acid, sulfonic acid, phosphoric acid, amine groups, thiols, hydroxyls or a combination of these groups. These groups in the polymer may be used to bond to other biologically relevant molecules, such as peptides, via disulfide, amide, or peptide bonds. The concentration of the polymer or its salts in the solution may be less than about 100 millimolar, preferably 10-20 mM, and the concentration may be used to control the morphology of the coating. It is expected that lower concentrations of the additive will result in less disruption of the crystalline morphology than higher concentrations of the organic additive. Polymers useful in the present invention may be derived from natural sources, made by solid phase synthetic techniques as known to those skilled in the art, or they may be purchased from suppliers such as Aldrich Chemical, Milwaukee Wis.

Figure 3B:
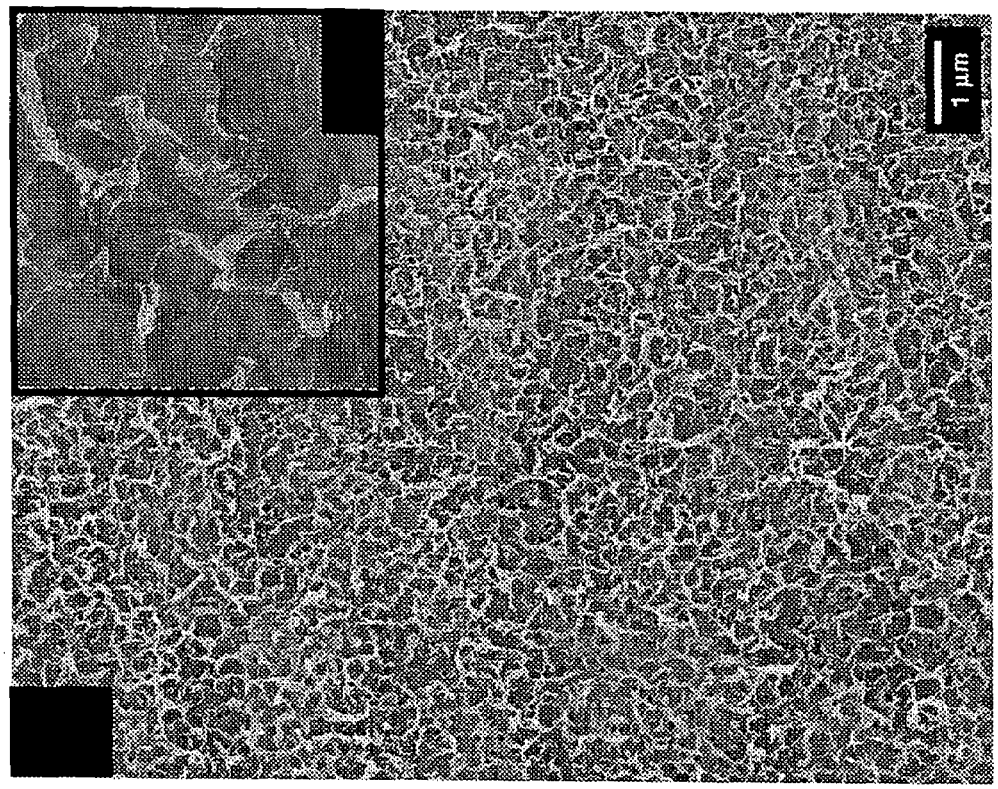
FIGS. 3A-B: Scanning electron micrograph digital images comparing purely inorganic OCP (A) and pLys-CP (B) coatings on titanium foil. Inset of (b) is a high magnification image revealing nanoscale character of the pLys-CP coating.
Figure 3A:
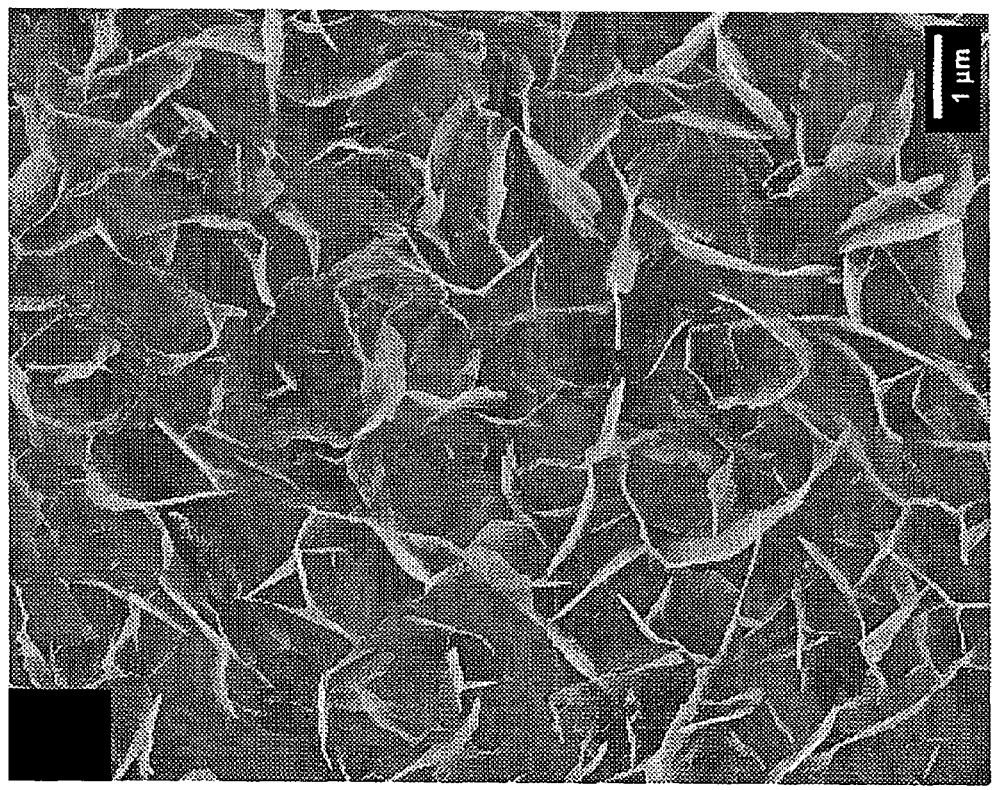

Preferably the coating on the substrate with the organic additive incorporated into it results in a material with morphological features smaller than those formed by a solution of the material deposited onto a substrate without the organic additive as shown in FIG. 3A and FIG. 3B. Preferably the features of the coating are less than about 2000 nanometers in size. The thickness of a coating on a substrate may be less than about 50 microns, is preferably less than about 10 microns and is more preferably less that 1 micron. Thinner coating provides for cell attachment and reduces the blockage of small pore features in porous substrates like biological foams of titanium or tantalum.

Preferably, the addition of the organic additive will influence crystal formation so as to create a nanocrystalline or poorly crystalline mineral phase. Such characteristics make the coating material particularly susceptible to acidic degradation during cellular remodeling. Alternatively, the coating material may be susceptible to enzymatic attack under physiological conditions, with a biological enzyme such as, but not limited to, pronase and trypsin. The coating may be disrupted by such enzymes when the organic component of the mineral composite is digested by the enzyme. It is desirable that the additive incorporate into the coating be susceptible to these two primary degradation means, acidic and enzymatic, in order that it be susceptible to natural bone remodeling processes in vivo. The susceptibility of different organic additives in the material coatings to acidic or enzymatic digestion may be monitored by changes in coating morphology (by scanning electron microscopy, for example) and chemistry (x-ray photoelectron spectroscopy, for example) with time during treatment of prepared coated substrates with biologically active enzymes or physiological solutions. Mineral biproducts from these degraded coatings are expected to be useful raw materials which may be used in the formation of newly mineralized tissues.

The material for the coating is dissolved in solution. Inorganic materials useful for such coatings may include but are not limited to hydroxyapatite, fluorapatite, carbonate fluoroapatite, carbonate hydroxyapatite and combinations of these. Also useful are calcium phosphate, calcium oxalate, calcium carbonate and combinations of these inorganic materials. Calcium phosphates may include but are not limited to dicalcium phosphate dihydrate, octacalcium phosphate, magnesium substituted the calcium phosphate. Inorganic ions such as but not limited to $Zn^{+2}$ or $Mg^{+2}$ may also be combined with $Ca^{+2}$ salts to pre-seed or be incorporated into the coating. These inorganic materials and salts of these materials may be obtained from natural sources or from chemical suppliers such as Aldrich Chemical, Milwaukee Wis. Preferably the concentration of each of the components of the coating material in the solution may be less than about 100 millimolar.

The temperature of the coating solutions may be used to control the rate and morphology of the coating process. The temperature of the solution should not degrade the organic polyamine. The temperature may be less than about 75° C. and preferably is ia the range of from about 5° C. to 40° C.

The substrate to be coated is preferably a biologically compatible material and may include polymers, metals, metal alloys, ceramics or a combination of these. The substrate preferably has the shape for its intended use prior to coating. Implant examples may include hip and knee implants, plates and pins for broken bones, dental implants, and other reconstructions. Substrates useful in the practice of this invention may have an oxide surface, a hydroxide surface, or combination of these groups coating at least a portion of the surface of the substrate. Preferably the coating has a surface containing functional groups that permit nucleation of a seed layer of a mineral or other material to be deposited onto it. Examples of functional groups in the surface include but are not limited to oxides, hydroxide, phosphates, and carbonates. Metals and alloys useful in the practice of this invention may include but are not limited to titanium and alloys thereof, surgical steels, amalgams, Co—Cr alloys, tantalum, or silicon and silica base materials. Preferably the substrate is an alloy of titanium alloy, an example of which is a titanium alloy called Ti-6A1-4V which is useful for orthopedic and dental implants. The metal or alloy may be a bulk material, a porous foam, or a coating or a deposited as an adherent film on another substrate like a ceramic. Suitable ceramic materials present oxide and hydroxide functionalities, for example alumina, sapphire, and calcium phosphate ceramics such as sintered apatite.

Pre-seeding of the substrate may be performed using a component of the coating composition or one similar in structure to it. The substrate may be pre-seeded with the coating material by contacting the substrate with a solution of the coating without the organic additive. For example, a seeding composition solution of $CaCl_2$ and $Na_2HPO_4$ may be used to contact the substrate prior to coating it with a solution including $CaCl_2$, $Na_2HPO_4$ and poly(L-lysine). Preferably the substrate is contacted with $CaCl_2$ and then the $Na_2HPO_4$. It is desirable that the pre-seeding establish a seed layer of the coating material on the substrate. The seed coating may also be formed by other methods including but not limited to chemical vapor deposition, atomic layer chemical vapor deposition, or spray coatings.

The substrate coated with the coating material including the organic additive may be used for growing or attachment of cells, tissues, or for releasing a therapeutic composition. Example of tissue may include but are not limited to bone and dentin. The coated substrate may be used in vitro to culture cells or tissue by placing it in a vessel with suitable cells, nutrients, and other reagents for cell tissue growth. A coated substrate or one with a culture of cells thereon may be used in vivo after implantation to grow or culture cells, tissues, dentin or bone in a patient. The substrate will be made of a biocompatible material that is coated with the material modified by incorporation of an organic additive such as a poly(amino acid) within the material.

The substrate coated with the material and the organic additive may be further modified to include other molecules such as but not limited to amino acids, peptides or self assembled peptide amphiphiles, bonded to the coating. For example, the incorporation of pLys into the Ca—P layer also introduced a valuable chemical tether for linking functional biomolecules to the coating. Poly(L-lysine)'s positively-charged free amine side chain may serve as a binding linker either through electrostatic interactions with negatively-charged molecules, or through the formation of amide bonds between lysine's free amine and carboxylic acids on the target molecule. The chemical functionality of the organic additive incorporated into the coating may be used for incorporation of biological molecules such as growth factors, peptide sequences, or therapeutic drugs. Peptides or self assembled peptide amphiphiles may also be bonded to the reactive groups of the organic additive incorporated into the coating material, such as a poly(amino acid), or by bonding the molecule or self assembled amphiphile to the crystalline material itself Such bonds may include but are not limited to amide, ester, and disulfide bonds. Preferably a peptide bonded to the organic additive in the coating includes an amino acid sequence useful for the attachment of different types of cells. Examples of asymmetric peptides having amino acid sequences useful for the attachment of different types of cells thereto include but are not limited to those in Table 3. Symmetric peptide amphiphiles, such as those disclosed in U.S. Pat. No. 5,670,483 and U.S. Pat. No. 5,955,343 the contents of which are incorporated herein in their entirety, may also be useful in the practice of this invention. Bola amphiphiles and self assembled bola amphiphiles may also be useful for bonding to the coatings of the present invention. Examples of self assembled peptide amphiphiles having amino acid sequences relevant for the attachment of different types cells thereto may be prepared from the peptides in Table 3.

TABLE 3

Peptide amphiphiles; S(P) represents a phosphorylated serine)

| PA | N-terminus | Peptide (N to C) | C-terminus |
|---|---|---|---|
| 1 | C16 | SEQ ID NO:4 CCCCGGGS(P)RGD | H |
| 2 | C16 | SEQ ID NO:5 CCCCGGGS(P) | H |
| 3 | C12 | SEQ ID NO:4 CCCCGGGS(P)RGD | H |
| 4 | C10 | SEQ ID NO:4 CCCCGGGS(P)RGD | H |
| 5 | C14 | SEQ ID NO:4 CCCCGGGS(P)RGD | H |
| 10 | C16 | SEQ ID NO:15 CCCCGGGS(P)KGE | H |
| 11 | C10 | SEQ ID NO:9 AAAAGGGS(P)KGE | H |
| 12 | C16 | SEQ ID NO:16 CCCCGGGS(P)DS(P)D | |
| 13 | C22 | SEQ ID NO:4 CCCCGGGS(P)RGD | H |
| 14 | C16 | SEQ ID NO:10 CCCCGGGSRGD | H |
| 15 | C16 | SEQ ID NO:11 CCCCGGGEIKVAV | H |
| 16 | C16 | SEQ ID NO:12 CCCCGGGS(P)RGDS | H |

Alternatively, the coating on the substrate may also be bonded to the peptides or to self assembled peptide amphiphiles, through a bond with the coating. Self assembled peptide amphiphiles bonded to the coating on the substrate may further include an encapsulated drug or therapeutic agent, drugs to promote cell adhesion, growth factors, or biologically relevant peptide sequences. The peptide amphiphile can have amino acids such as thiol moieties or others for cross-linking to enhance the stability of the self assembled peptide amphiphile bonded to the substrate coating.

The polymeric structure incorporated into the coating material on the substrate may be further bonded to molecules such as but not limited to growth factors, therapeutic drugs, peptides, and self assembled peptide amphiphiles. The bonding with the molecules may be through van der Waals interaction, ionic bonding, hydrogen bonding, or chelation. Alternately, the coating material on the substrate may be bonded to a peptide or a self assembled peptide amphiphile through a variety of bonds including but not limited to disulfide bonds and preferably ester or amide linkages between the polyamine and the peptide. The formation of amide bonds between the polymer in the coating and a peptide is conducted in a polar organic solvent, for example but not limited to N,N-dimethylformamide (DMF) or N-methylpyrrolidinone (NMP), both of which are capable of solublizing amino acids. The method also involves utilizing a compound such as O-Benzotriazole-N,N,N',N'-tetramethyl-uronium-hexafluoro-phosphate (HBTU) as a catalyst to increase the reactivity of carboxylic acid functional groups on the peptide amphiphile. Other peptide coupling agents or activators include but are not limited to: dicyclohexylcarbodiimide (DCC); O-(7-azabenzotriazol-1-yl)-1,1,3-,3-tetramethyluronium hexafluorophosphate (HATU); and benzotriazol-1-yl-oxytripyrrolidinophosphonium hexafluorophosphate (PyBOP). These reactive acid groups then undergo a reaction with free amines, after which the presence of the proton sink diisopropylethylamine (DIEA) assists in the final elimination reaction to remove the HBTU and water, leaving behind a stable amide linkage. Self assembled peptide amphiphiles may be crosslinked via disulfide bonds before bonding or attachment to the coating on the substrate.

The material coating the substrate may be comprised of a metal deficient mineral incorporating the additive. The additive incorporated into the coating may be present up to about 25% weight or less and reduces the size of the crystallites present in the coating compared to crystallites in a coating without the additive. The additive may include but is not limited to poly(amino acids). For example, the substrate may be comprised of calcium deficient octacalcium phosphate mineral, the crystal growth of which has been frustrated and modified by the polyamine, poly(L-lysine), present during mineralization. Without wishing to be bound by theory, it may be that the (poly(L-lysine)) is intimately incorporated into the calcium deficient octacalcium phosphate material during crystallization process. The morphology of the coating resulting from this organic modification consists of irregular features 1-2 orders of magnitude smaller than purely inorganic (octacalcium phosphate) mineral coatings as shown by comparison of FIG. 3a and FIG. 3b. This increased texture and reduced feature size is expected to have a favorable influence on cell attachment, proliferation, and spreading. In addition, the disrupted, poorly crystalline character of the coating, combined with the enzyme-vulnerable organic component of the mineral composite should to make it particularly accessible for natural re-absorption and remodeling processes. Finally, the incorporation of the polyamino acid into the material coating provides additional chemical functionality via the free amines or acids on the side chains. Such chemical functionality may be used for incorporation of biological molecules, such as growth factors, biologically relevant peptide sequences, or therapeutic drugs.

One embodiment of the present invention is a method for coating a material onto an implantable substrate. The method comprises coating a biologically compatible substrate having a seed layer compatible with the coating with a composition that is a solution of a dissolved coating material and an organic additive. The method may further include steps or acts of preparing the seed layer on the substrate and bonding molecules or self assembled supramolecular structures to the coating material on the substrate. The coating composition may be applied to the pre-seeded substrate by methods know to those skilled in the art for contacting or coating substrates with the composition. The substrate may be coated by soaking it in the composition comprising the material and the polymer, for example $CaCl_2$, $Na_2HPO_4$, and poly(L-lysine). For example, a preseeded substrate is placed into a $CaCl_2$ solution supplemented with a poly(amino acid) acid. A salt such as $Na_2HPO_4$ is then added to this combination and the samples are incubated. The coating step may be repeated one or more times. For substrates with pores or channels, it may be preferable to coat the substrates by flowing the composition through the substrate (preferable for small pores) or across the substrate. Closed loop flow systems employing a pump and tank for the composition may be used and the flow rate controlled by the pump, valves, or flow controllers. Alternatively the substrates may be sprayed coated using an atomizer or other sprayer. Multiple coatings of the substrate with fresh coating composition may result in enhanced coating thickness and uniformity on the substrate. Preferably the coating material comprises 1-15% of the organic additive by weight.

FIG. 3A and FIG. 3B illustrate the dramatic influence a polyamine such as poly(L-lysine) has on the growth of the octacalcium phosphate on a pre-seeded biocompatible titanium sustrate. The scanning electron micrograph in FIG. 3A shows that a purely inorganic coatings is comprised of large (>1 micron), well-formed, plate-like crystals of octacalcium phosphate. In contrast, poly(L-lysine)-modified coatings shown in FIG. 3b are composed of distorted, irregularly-shaped, poorly crystalline features 1-2 orders of magnitude smaller than the purely inorganic version of the mineral. Many of the features constituting these materials are smaller than 100 nm in scale, giving the material a genuinely nanoscale texture. Such a nanoscale texture or morphology may promote cell attachment and spreading on coated substrates or monolithic samples of the coating. X-ray diffraction of this pLys-OCP coating further illustrated its poorly crystalline character, which should make the material particularly susceptible to acidic degradation pathways during cellular remodeling. Treatment of the pLys-OCP with a biological enzyme, such as pronase, shows by SEM and energy dispersive x-ray spectroscopy (EDS), that the coating texture and morphology of the material is disrupted when the organic component of the mineral composite is digested by the enzyme. Poorly crystalline organo-material composite coatings may not only be particularly suitable for acidic degradation, but also enzymatic digestion, two primary means for re-adsorption of natural bone in vivo.

Figure 9:
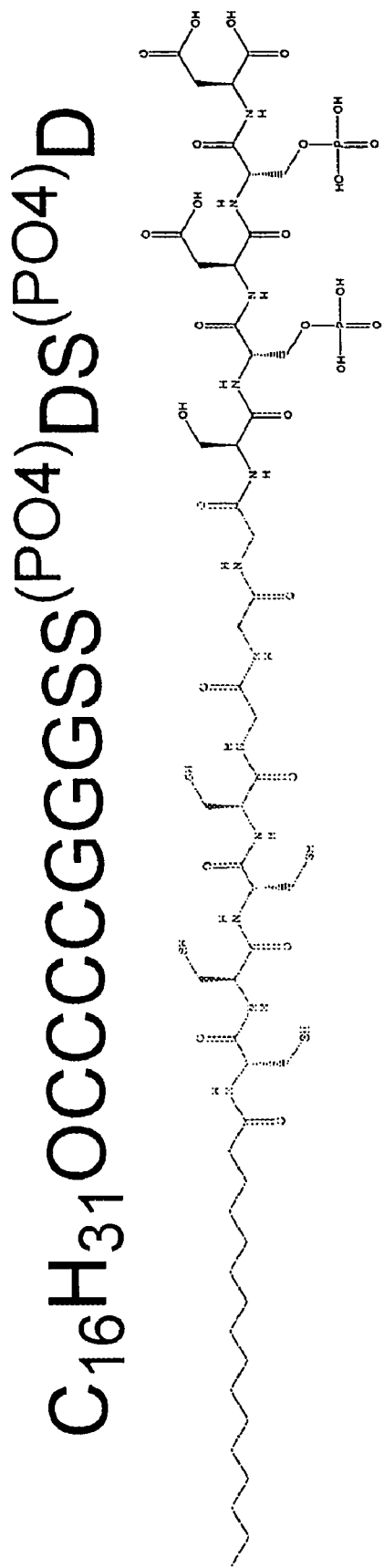
FIG. 9 is a schematic structural illustration of a peptide $C_{16}H_{31}O$(SEQ ID NO:3) useful for attachment to coatings of the present invention, where ($PO_4$) indicates phosphorylated seine.
Figure 10B:
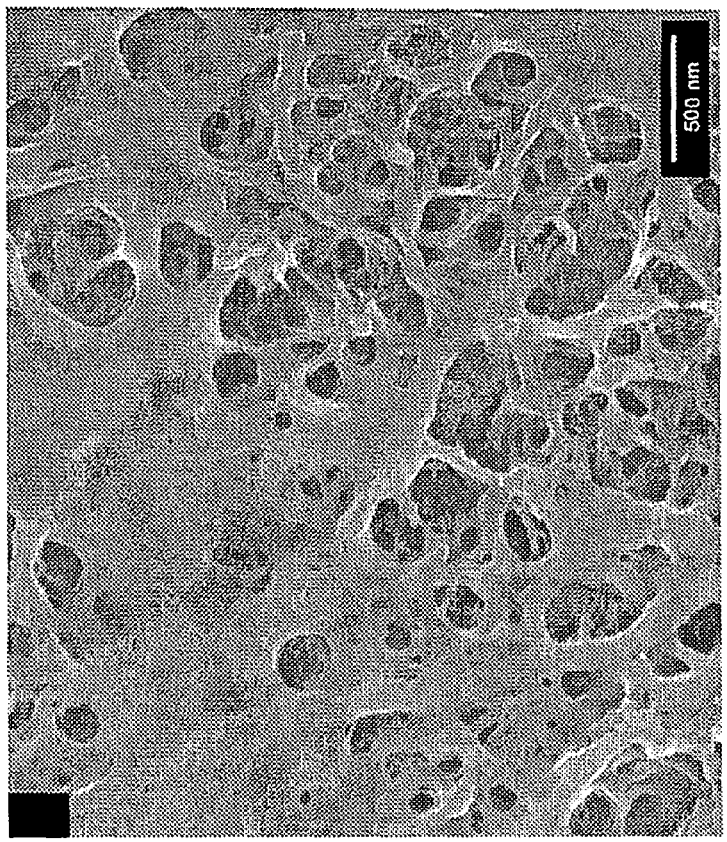
FIGS. 10A-B (A) A scanning electron micrograph digital image of self assembled peptide amphiphile nanofiber bundles attached to a poly(L-lysine) modified calcium phosphate textured coating of the present invention; (B) a higher magnification scanning electron micrograph of the self assembled nanofiber in (a), revealing layers of individual fibers.
Figure 10A:
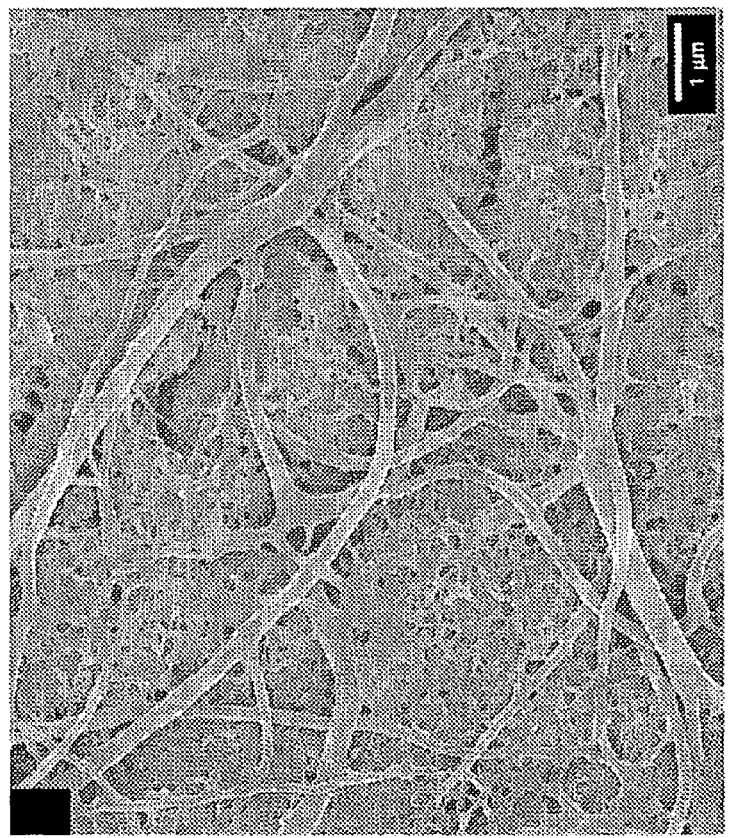

The presence of a polyamine like poly(L-lysine) not only influences the coating morphology, crystallite size, and remodeling potential, but it also provides an element of chemical functionality to the system. The side chains from the poly(L-lysine) incorporated into the mineral coating contain free amines which are available for chemical reaction. For example, these amines may form amide linkages with free acids on biologically relevant peptide sequences. FIG. 9 illustrates a peptide amphiphile which may be self assembled to form nanofibers, where the molecules' aliphatic tails are sequestered in the middle of the fiber and the functional peptide sequence is exposed on the outside of the assembled nanofiber. The cysteine residues in the molecule may be exposed to oxidative conditions, thereby covalently stabilizing the nanofiber through the formation of intermolecular disulfide bonds. The carboxylic acids exposed on the outside of the molecule may be reacted with the free amines from the poly (L-lysine) to form an amide linkage, covalently linking the peptide amphiphile nanofiber to the textured plys-OCP surfaces. FIG. 10A shows the attachment of nanofiber bundles to the poly (L-lysine) modified calcium phosphate coating on the titanium surface. In the higher magnification of FIG. 10B, it is possible to resolve individual nanofibers (see arrows) coating the textured features of the underlying (L-lysine) modified calcium phosphate coating. The peptide amphiphile used in this example has been modeled after phosphophoryn, a dentin-specific protein associated with control of mineralization in teeth. Of course nearly any peptide amphiphile nanofiber could be used for this application, so long as it exposed the necessary carboxylic acids for the amide linkage. Conversely, incorporation of an organic additive to the calcium phosphate coating which displayed free acids could be used similarly to bind PA nanofibers displaying free amines. Peptide amphiphiles are an example of a supramolecular aggregate which may be attached to an pLys-OCP surface, but this chemical functionality may be similarly utilized for attachment of individual molecules or peptide sequences as well. For example the peptide sequence arg-gly-asp (RGD), commonly associated with cell attachment could be coupled to the surfaces to enhance cell attachment to the plys-OCP surface.

A variety of physical and chemical analysis may be used to characterize coatings prepared by the methods and compositions of the present invention. Methods such as XRD, RFTIR, XPS, TGA, and elemental analyses can be used by one skilled in the art to determine that the additive modified coatings have reduced feature size compared with crystalline coatings without the additive. The effects on morphology using different amounts of additive may also be determined with these methods. For example the incorporation of an additive into the mineral phase is illustrated by the disruption of the coating crystallinity seen by XRD and FTIR as well as by the coating's chemical reactivity or ability to promote cell attachment.

EXAMPLE 1

Commercially pure titanium or any titanium alloy presenting a titanium dioxide surface is cleaned ultrasonically in an organic non-polar solvent, an organic polar solvent, and finally distilled water. The cleaned titanium is then etched in a mild hydrofluoric acid, nitric acid solution before repassivation in nitric acid. Passivated samples are rinsed thoroughly in distilled water and dried. Cleaned, passivated samples are then dehydrated by vacuum desiccation and stored at 120° C. before amino-silanization. Dry, passivated surfaces introduced to a dilute solution of an amino silane, such as aminopropyltriethoxysilane (APTES) in an anhydrous hydrophobic organic solvent, such as toluene, under nitrogen. Amino-silanized titanium substrates are then rinsed thoroughly in an organic non-polar solvent, an organic polar solvent, and finally water before annealing at 60° C. for 1 hour under nitrogen.

Figure 12B:
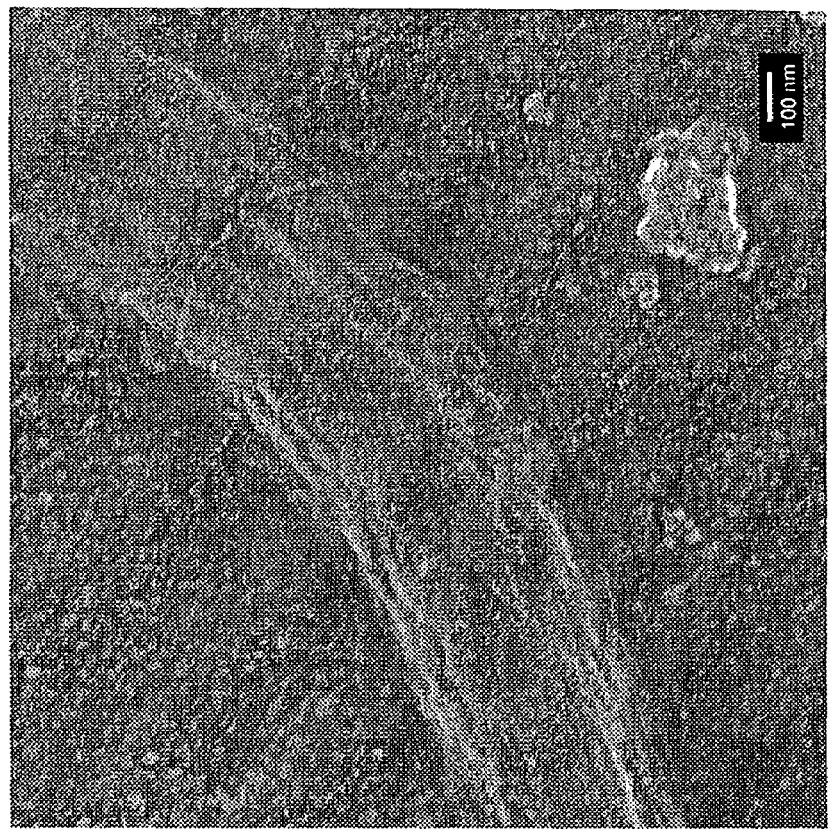
FIG. 12: Scanning electron micrograph digital images of peptide amphiphile nanofibers covalently linked to an aminosilanized titanium surface, showing low and high magnification images of these fibers covalently bound to the Ti surface.
Figure 12A:
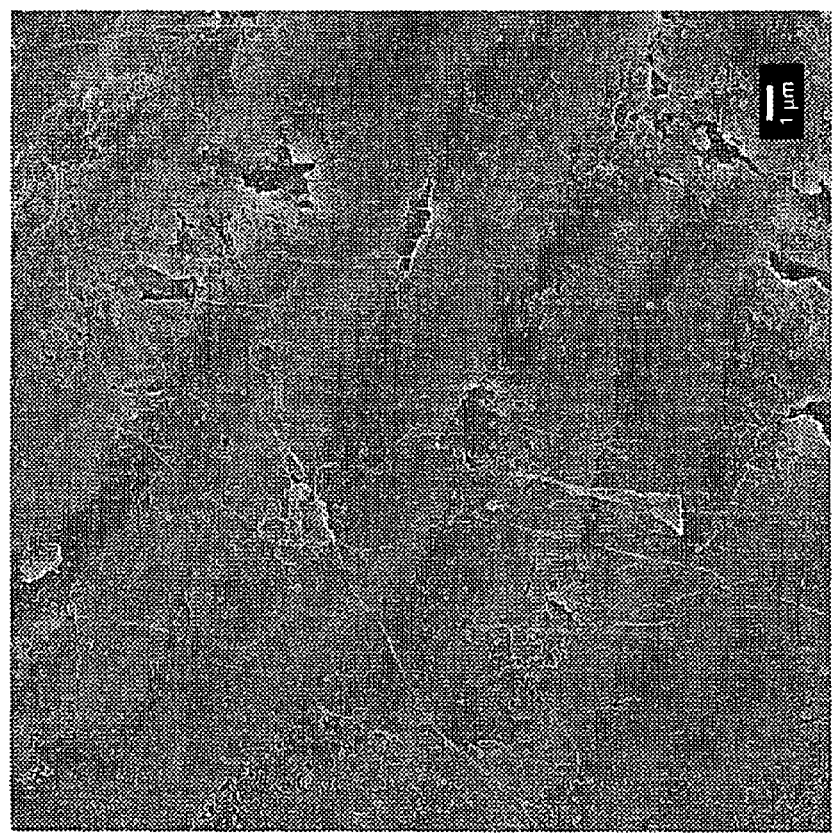

Covalent binding of PA nanofibers to amino-silanized $TiO_2$ surface. To the suspension of cross-linked nanofibers in N,N-dimethylformamide (DMF), solutions of O-Benzotriazole-N, N,N',N'-tetramethyl-uronium-hexafluoro-phosphate (HBTU) and diisopropylethylamine (DIEA) are added to provide slightly less than 1 equivalent (0.95) of HBTU for every free carboxylic acid on the nanofibers and approximately 6 equivalents for every estimated free amine on the amino-silanized titanium surface. This solution is allowed to incubate for several minutes before exposure to the amino-silanized titanium surface. Once introduced, the amino-silanized titanium is shaken for least 1 hour in the nanofiber reaction solution before thorough rinsing with water and drying at room temperature. FIGS. 12A and 12B show low and high magnification images of these fibers covalently bound to the Ti surface.

EXAMPLE 2

Covalent linking of preassembled peptide nanofibers to a poly(L-lysine) modified calcium phosphate coating on a titanium surface. PA nanofiber preparation: The peptide nanofibers are assembled, cross-linked, dialyzed, lyophilized and resuspended in DMF as above.

Calcium phosphate coating preparation: Titanium foils are cleaned, etched, passivated and rinsed as above. Rather than drying them and treating them with APTES, however, the foils are immersed in a solution of $CaCl_2$ and $Na_2HPO_4$ for at least 30 minutes to pre-seed the surface with calcium phosphate. This preseeding solution is then replaced with a solution containing poly(L-lysine, $CaCl_2$, and $Na_2HPO_4$) for at least 3 hours before the samples are rinsed with water and dried at room temperature. It is believed that the poly(L-lysine) is incorporated into the resulting mineral phase of the newly formed calcium phosphate coating, and that free amines from the side-chains of the poly(L-lysine) are displayed on the textured coating surfaces.

Covalent binding of PA nanofibers to an amino-silanized poly(L-lysine)-modified calcium-phosphate-coated $TiO_2$ surface. To the suspension of cross-linked nanofibers in N,N-dimethylformamide (DMF), solutions of O-Benzotriazole-N, N,N',N'-tetramethyl-uronium-hexafluoro-phosphate (HBTU) and diisopropylethylamine (DIEA) are added to provide slightly less than 1 equivalent (0.95) of HBTU for every free carboxylic acid on the nanofibers and approximately 6 equivalents of DIEA for every estimated free amine exposed on the lysine-modified calcium phosphate coating titanium surface. This solution is allowed to incubate for several minutes before exposure to the coated titanium surface. Once introduced, the calcium-phosphate coated titanium is shaken for least 1 hour in the nanofiber reaction solution before thorough rinsing with water and drying at room temperature. FIG. 10A is a scanning electron micrograph showing bundles of fibers attached to the textured coating surface. FIG. 10B is a higher magnification image revealing layers of individual fibers coating the textured structures of the calcium phosphate coating.

EXAMPLE 3

Procedure for the growth of pLys-OCP: titanium surfaces are cleaned sequentially in an organic non-polar solvent, an organic polar solvent, and water. Cleaned titanium foils may be briefly etched in a mild hydrofluoric acid, nitric acid solution to remove the existing surface oxide before repassivation in a more concentrated nitric acid solution for surface passivation. Acid-treated samples are then rinsed thoroughly with distilled water and placed in a preseeding solution consisting of 2 mM $CaCl_2$ and 1.2 mM $Na_2HPO_4$ for at least 30 minutes at room temperature. Longer exposure times (up to 24 hours) may result in better coverage. After pre-seeding, samples are then placed in a fresh mineralizing solution comprised of 2 mM CaCl, 1.2 mM $Na_2HPO_4$, supplemented with 1 mM poly(L-lysine), and incubated at least 3 hours at room temperature. This mineralization step may be repeated for enhanced coating thickness. Mineralized samples are rinsed thoroughly with distilled water and dried at room temperature.

EXAMPLE 4

Chemical reagents were purchased from Sigma-Aldrich (St. Louis, Mo.). Solvents were obtained from Fisher Scientific, (Hanover Park, Ill.). Titanium foil was obtained from Goodfellow, Inc. (Berwyn, Pa.).

Figure 1A:
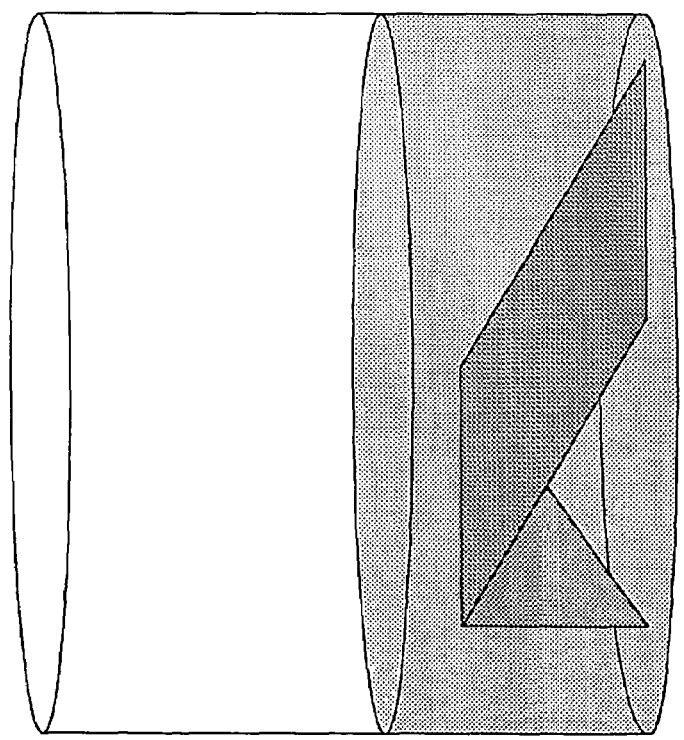
FIG. 1A: Experimental setup (schematic) for growth of calcium phosphate coatings on titanium foil.

Commercially pure titanium (Ti) foil (0.032 mm) was cut into rectangular sections with dimensions 5×8 mm. One corner of each sample was bent normal to the face of the foil. Foils were then cleaned ultrasonically for 15 minutes each in reagent grade dichloromethane, acetone, and deionized water. Cleaned foils were then etched for 1 minute in 0.25% hydrofluoric acid (HF), 2.5% ($HNO_3$) before placed in 40% nitric acid ($HNO_3$) for 40 minutes for surface passivation. Acid-treated samples were then rinsed thoroughly with deionized water. Cleaned, passivated samples were placed in wells of a 24-well tissue culture polystyrene (TCPS) well plate with the folded corner down, effectively suspending the underside of the foil above the TCPS surface as shown in FIG. 1. This configuration insured that any coating seen on the underside of the titanium substrate was grown directly on the foil surface and was not simply the result of adherent precipitates fallen out of solution.

Samples were then preseeded by placing them in a solution of 2 mM $CaCl_2$ and adding $Na_2HPO_4$ (final concentration 1.2 mM) for time periods ranging from 10 minutes to 24 hours at room temperature. Control preseeding solutions included 2 mM $CaCl_2$ alone, 1.2 mM $Na_2HPO_4$ alone, 1.2 mM NaCl alone. 2 mM $CaCl_2$ with 1.2 mM $Na_2HPO_4$ and 1 mM poly(L-lysine) (MW=37,000). After preseeding, samples were then placed in 2 mL of a fresh 2 mM $CaCl_2$ solution, supplemented with 1 mM poly(L-lysine). $Na_2HPO_4$ was then added (final concentration 1.2 mM), and samples were incubated in this mineralization solution for at least three 24 hours at room temperature. This mineralization process was repeated once more. The pH of these mineralizing solutions was tracked with a Fisherbrand electronic pH meter. Mineralized samples were rinsed thoroughly with deionized water and dried by vacuum desiccation. Dry samples were then examined by x-ray photoelectron microscopy (XPS), reflective Fourier Transform Infrared Spectroscopy (RFTIR), and scanning electron microscopy including energy dispersive x-ray analysis (EDS). XPS was conducted using an Omicron XPS at 15 kV and 20 mA, and spectra were processed using EIS software (v 2.1.0). RFTIR was performed on coated foil substrates using a Bio-Rad FTS-40 FTIR spectrophotometer (4000-700 $cm^{-1}$, 64 scans, 2 $cm^{-1}$ resolution) using a blank Ti foil as a background. SEM samples were coated with 3 nm of gold-palladium prior to examination in a Hitachi S4500 field emission scanning electron microscope at 20 kV with a Princeton Gamma Tech x-ray detector.

Non-adherent precipitate was then collected by a series of water rinses followed by centrifugation and lyophilized. Dry precipitate was tested by powder x-ray diffraction (XRD) using a Rigaku D-Max x-ray powder diffractometer at 40 kV and 20 mA. Water and organic content in the dried precipitate was determined by high resolution thermogravimetric analysis (TGA) using a TA instruments Hi Res TGA 2950. Samples were heated at 3° C./minute to 450° C. and held for 120 minutes.

Degradation experiments were performed on foil samples, coated with OCP and pLys-CP, grown as described above. Samples were placed in 1 mL of each respective degradation solution for 24 hours before being rinsed thoroughly in Millipore water and dried by vacuum desiccation. Enzyme-based solutions included 0.25% trypsin in hanks balanced salt solution (HBSS) and 0.2% pronase in HBSS. Coating degradation by pH variation was conducted using HBSS (pH 7.4) and citrate buffer solutions at pHs 7, 6, 5, 4, 3, and 2. Treated samples were then probed by EDS in the SEM at 20 kV for 100s, prior to sputter coating with 3 nm Au—Pd for imaging at 20 kV.

Chemical functionality was measured by coupling Boc-S-tert-butylmercapto-L-cysteine (Boc-Cys(StBu)-OH) to free amines exposed on the pLys-CP coating. Both OCP and pLys-CP coatings were prepared as described above. Surface concentration of free amines was measured using a quantified ninhydrin test. Briefly, dried samples were treated with a mix of phenol in ethanol and potassium cyanide in pyridine at 100° C. for 5 minutes before the addition of 60% ethanol and rinsing with tetraethylammonium chloride in dichloromethane. Absorbance of the resulting violet solution was measured at 570 nm and compared to a standard curve measured from graded pLys solutions. Samples not used in the ninhydrin reaction were shaken overnight in 0.4 mL of dimethylformamide (DMF) containing 0.1% Boc-Cys(StBu)-OH, with 0.95 molar equivalents of 1-H-Benzotriazolium, 1-[bis(dimethylamino)methylene]-hexafluorophosphate(1-), 3-oxide (HBTU) and 0.5 mM diisopropylethylamine (DIEA). Control samples were exposed to the cysteine compound in the absence of the HBTU or DIEA. Half of the samples from each set of reaction conditions was rinsed thoroughly in deionized water, while the other half was washed in a saturated NaCl solution for 10 minutes before thorough rinsing in deionized water. Rinsed samples were then dried before examination by XPS at 225 W (15 kV and 15 mW).

Figure 2:
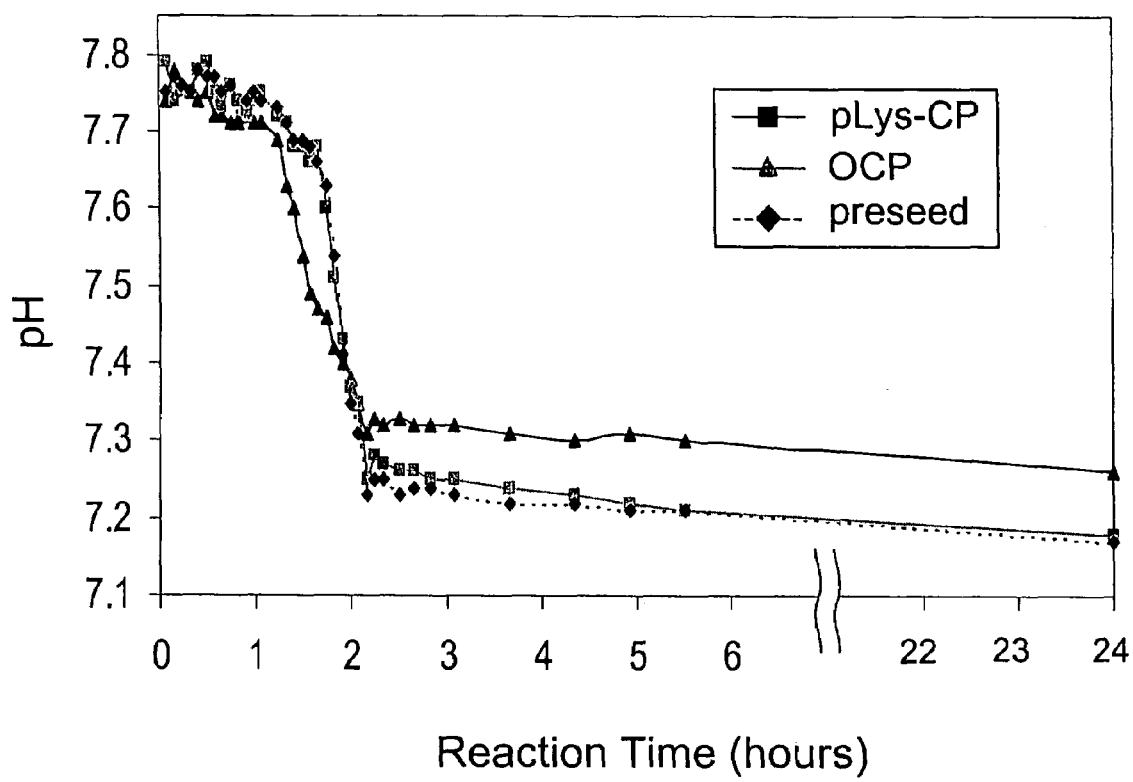
FIG. 2: Time dependent pH variation of reaction solution during sample preseeding and calcium phosphate coating growth.

The calcium phosphate growth reactions were tracked visually as well as by monitoring reaction pH. The calcium chloride solutions began clear and colorless at approximately pH 5.8-5.9. Within seconds of adding the phosphate solution, the pH rose quickly to approximately pH 7.8, producing a fine white precipitate. In purely inorganic reactions, this suspended precipitate grew coarser over the next 3-4 hours as it settled in the reaction well. The precipitate in pLys-containing solutions, however, remained extremely fine and had a lesser tendency to settle. FIG. 2 shows the variation of the reaction pH, tracked from the point of equilibration after phosphate addition (approximately 1 minute) through 24 hours. The pH traces are characterized by a relatively gradual pH decrease, interrupted by a single abrupt drop from approximately pH 7.6 to pH 7.2 in just over an hour. It is worth noting that in the reaction solution containing pLys the significant drop in pH began notably sooner and the final pH remained slightly higher than that of the inorganic controls.

SEM micro graphs of the coatings produced by these reactions are shown in FIG. 3. The coating in FIG. 3A is purely inorganic, whereas the coating in FIG. 3B has been modified by incorporation of pLys. The purely inorganic coating is composed of large, thin, plate-like calcium phosphate crystals commonly exceeding 1 micron in length and width, a morphology consistent with that octacalcium phosphate (OCP). The coating is approximately 4-7 microns thick (2-3 crystal dimensions), and throughout the thickness of the coating crystals are oriented both parallel and perpendicular to the sample surface. In contrast, the pLys-modified calcium phosphate (pLys-CP) consists of distorted, frustrated crystals an order of magnitude smaller than their inorganic counterparts. The high magnification inset in FIG. 3B illustrate that these textures are furthermore composed of substructures less than 100 nm in dimension, revealing a nanoscale character in the modified coating. This coating, also 2-3 features thick, is commonly 1 micron thick or less, but remains uniform over the entire foil surface.

TGA of the OCP precipitate produced a mass change of around 9.5±0.2%, a value reasonably consistent with expected water loss from hydrated OCP crystals (9.2%). Analysis of the pLys-modified precipitate showed a similar amount of water loss, but produces a total mass loss of 23±1%, illustrating that the mineral is composed of as much as 14% poly(L-lysine). Elemental analysis shows a total carbon, hydrogen, and nitrogen content (by mass) of 14.2±0.2%, confirming the lysine content derived from the TGA. Furthermore, the mass ratio of carbon to nitrogen in the elemental analysis is 2.6, which agrees with the expected ratio of carbon to nitrogen in poly(L-lysine) of 2.57. This consistency rules out the possibility that the pLys-CP contains significant amounts of any carbonated calcium phosphate species.

Figure 4:
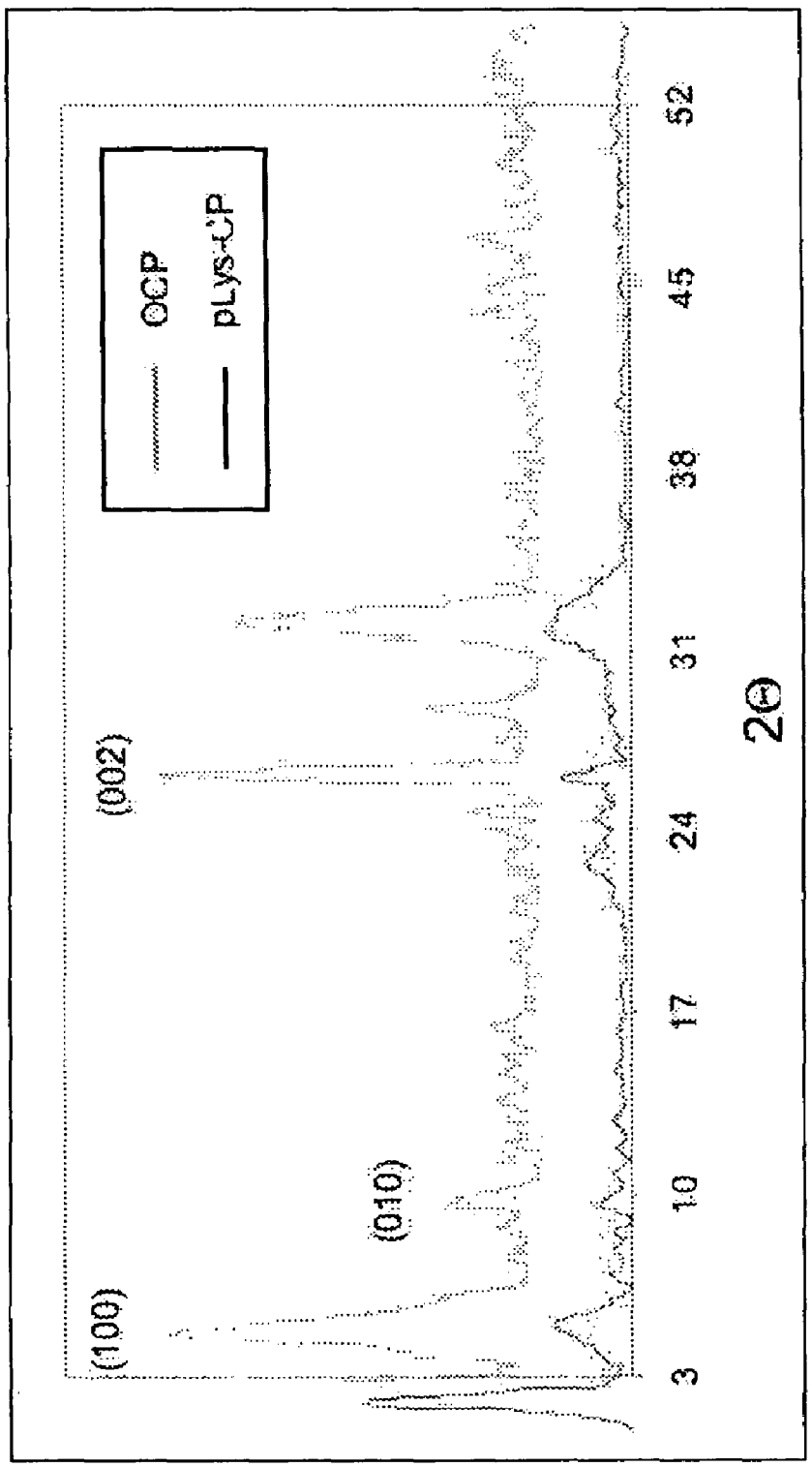
FIG. 4: Powder XRD patterns for OCP and pLys-CP. Major diffraction planes for OCP are labeled.

X-ray diffraction patterns of the pLys-CP precipitate, shown in FIG. 4, show relatively weak, broad diffraction peaks consistent with a poorly crystalline calcium phosphate. These broad peaks are reminiscent on the OCP crystal diffraction pattern, obtained from the inorganic controls. Distinguishing diffraction spacings for OCP (100), (010), and (002) are illustrated in FIG. 4.

Figure 5:
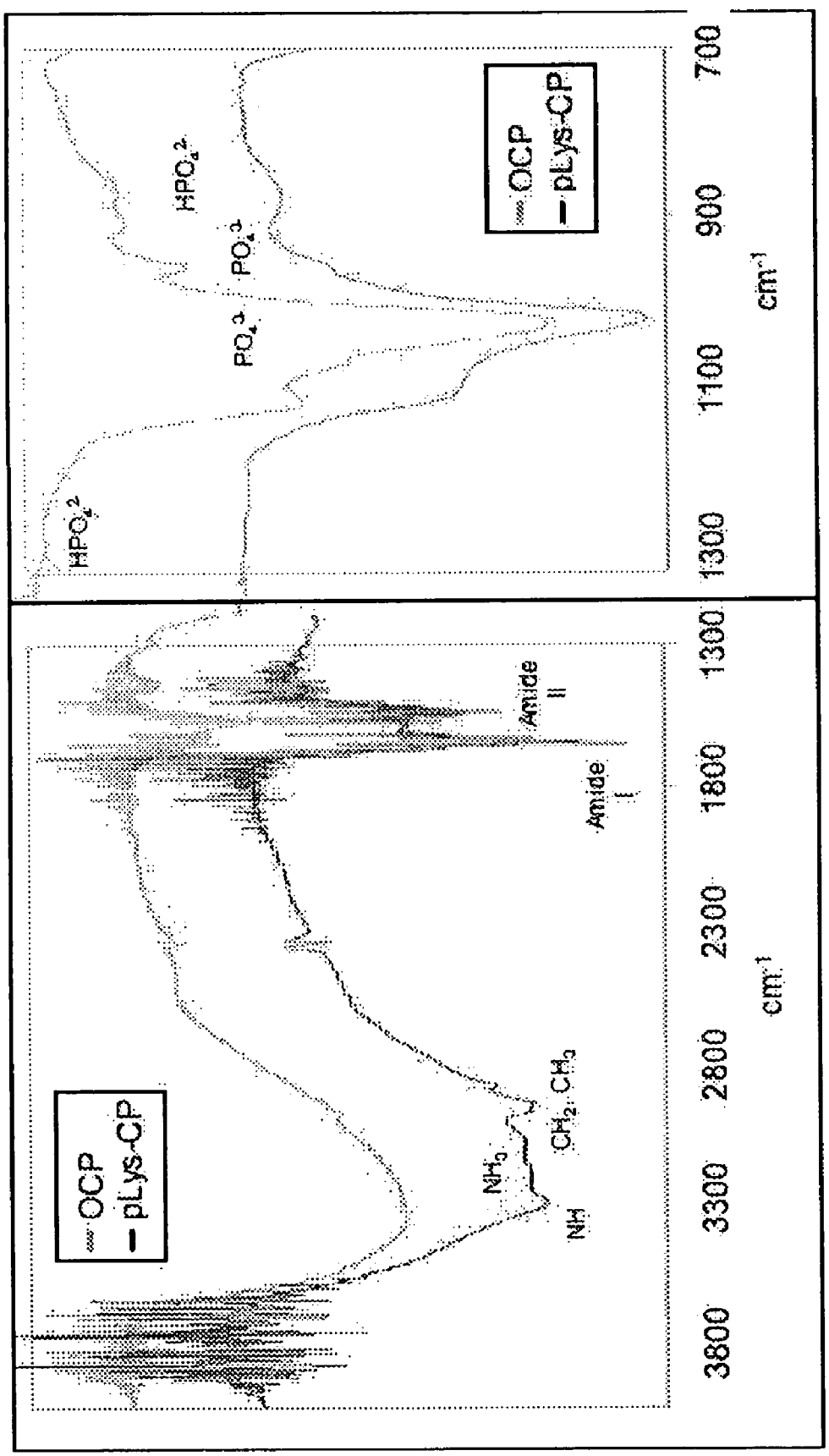
FIG. 5: Reflective FTIR spectra for OCP and pLys-CP coatings on Ti. Inorganic coating patterns reveal characteristic bands for OCP, while pLys-CP coating shows concomitant presence of poorly crystalline OCP and poly(L-lysine). High frequency bands between 1350 and 2000 and above 3400 are believed to be due to ambient water from the reflective experimental setup.
Figure 6B:
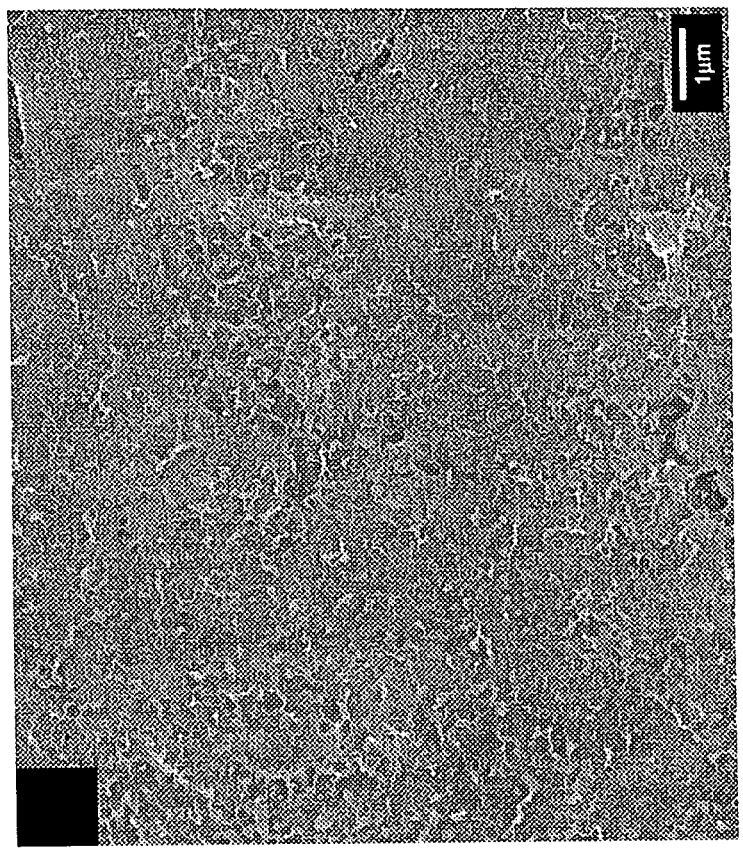
FIGS. 6A-B: A) Scanning electron micrograph digital image of a titanium surface, preseeded for 10 minutes with $CaCl_2$ and $Na_2HPO_4$. No calcium phosphate seeds are visible; B) Scanning electron micrograph digital image of a titanium surface preseeded for 2 hours with $CaCl_2$ and $Na_2HPO_4$. Seed crystals are clearly visible on a Ti surface after 2 hours of growth.
Figure 6A:
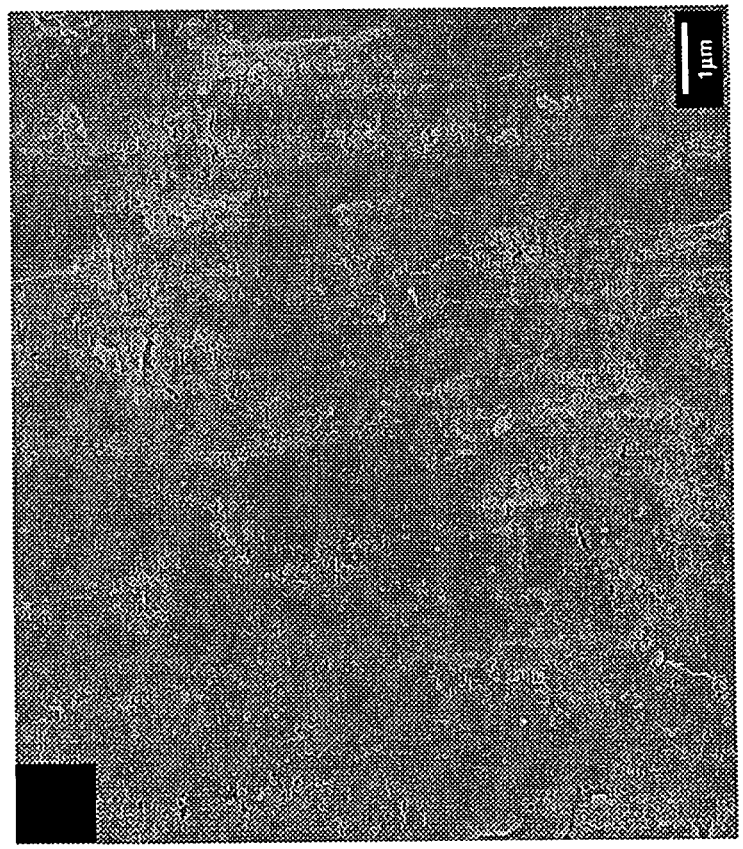

Examining the reflective FTIR spectra in FIG. 5, the inorganic coating produces bands corresponding to $PO_4^3$ stretches at 963, 1025, 1037, 1078, and 1115 $cm^{-1}$. In addition, there are clear bands characteristic of octacalcium phosphate, such as those from the P—OH stretches in $HPO_4^{2-}$ at 873 and 917 $cm^{-1}$. By comparison, the pLys-CP spectrum better describes a poorly crystalline or amorphous calcium phosphate, with broad $PO_4^3$ bands at 963, 1025, and 1115 $cm^{-1}$. The well-defined $HPO_4^{2-}$ bands seen in the inorganic sample, have been replaced by a single, broad $HPO_4^{2-}$ band around 880 $cm^{-1}$. In addition, the pLys-CP spectrum clearly reveals the presence of poly(L-lysine) in the mineral, indicated by $CH_2$ and $CH_3$ bands between 2990 and 2850 $cm^{-1}$ a strong $NH_2$ deformation bands at 1650 $cm^{-1}$, and an $NH_3^+$ band at 3073. These observations collectively illustrate that poly(L-lysine) has been incorporated into the calcium phosphate mineral system and has disrupted the crystallization of the naturally forming octacalcium phosphate phase.

Coating and pretreatment analysis by XPS is summarized below in table 4.

TABLE 4

XPS Analysis of Calcium Phosphate Pretreatments and Coatings

| Coating | Binding energy eV (±0.1) | | | | | | Ca:P ratio |
|---|---|---|---|---|---|---|---|
| | Ca $2p_{3/2}$ | Ca $2p_{1/2}$ | P 2p | O 1s | N 1s | C 1s | |
| OCP | 347.2 | 350.9 | 132.7 | 531.0 | — | 284.8 | 1.31 ± 0.02 |
| PLys-CP | 347.2 | 350.8 | 132.8 | 531.0 | 400.2 | 284.8 | 1.15 ± 0.02 |
| Preseed 2 hours | 347.2 | 350.8 | 133.2 | 531.1 | — | 284.9 | 0.30 ± 0.06 |
| Preseed 10 min | 347.0 | 350.6 | 133.2 | 531.5 | — | 284.8 | 1.55 ± 0.06 |
| $CaCl_2$ only | 347.0 | 350.8 | — | 531.3 | — | 284.8 | — |
| $Na_2HPO_4$ only | — | — | — | 530.9 | | | |

Calcium, phosphorous, and oxygen binding energies for both the OCP and pLys-CP coatings agree reasonably with previously published values for calcium phosphates such as OCP. The nitrogen peak at 400.2 eV in the pLys-CP scans confirms the presence of poly(L-lysine) in this modified coating. Calcium phosphate ratios were determined according to the expression in equation 1:

$$Ca:P = \frac{\frac{I_{Ca}}{S_{Ca}}}{\frac{I_P}{S_P}} \quad (1)$$

In equation 1, $I_x$ is the intensity of the corresponding XPS peak for element "x" and $S_x$ is the sensitivity factor for element "x." The ratio of 1.31 in the inorganic coating is in reasonable agreement with the expected values for OCP (1.33). The value of 1.14 in the pLys-CP coating is consistent with a calcium deficient OCP. The XPS data also provide some information about the preseeding process. First, the data shows that small amounts of calcium alone may be adsorbed to the Ti surface in the absence of phosphate, whereas phosphate alone does not significantly bind to a bare Ti surface after 24 hours. Alternatively, cotreatment of the surfaces with $CaCl_2$ and $Na_2HPO_4$ results in the formation of relatively Ca-rich calcium phosphate complexes in as little as 10 minutes. Up through approximately 1.5-2 hours, though, there are no indications of crystal formation visible in SEM. By 2 hours, however, small crystallites, visible in FIG. 6 have decorated the metal surface, and the calcium phosphate ratio has dropped to 1.3.

The formation of this seed layer on the titanium surface permits the successful growth of pLys-CP on the Ti surface. Table 5 below summarizes the coverage results from a variety of pre-seeding treatments.

TABLE 5

Dependence of pLys-CP Growth on Ti Surface Preseeding Method

| Preseeding treatment (24 hours unless otherwise indicated) | Subsequent pLys-CP coating growth |
|---|---|
| 2 mM $CaCl_2$ + 1.2 mM $Na_2HPO_4$ + pLys | Negligible |
| 2 mM $CaCl_2$ | Negligible |
| 1.2 mM $Na_2HPO_4$ | Negligible |
| 2 mM NaCl | Negligible |
| 2 mM $CaCl_2$ + 1.2 mM $Na_2HPO_4$ (10 minutes) | 25-50% coverage |
| 2 mM $CaCl_2$ + 1.2 mM $Na_2HPO_4$ (30 minutes) | 75% coverage |
| 2 mM $CaCl_2$ + 1.2 mM $Na_2HPO_4$ (>3 hours) | 100% surface coverage |

It is clear from the table that the pre-seeding treatment including both calcium and phosphate produced an adequate surface for growth of the pLys-OCP coating. Interestingly, the $CaCl_2$ pretreatment, which did result in the adsorption of calcium to the metal surface, was insufficient to promote subsequent pLys-CP growth. Similarly, the $Na_2HPO_4$ treatment alone did not promote subsequent pLys-CP formation on the metal surface. The pre-seeded layer of calcium phosphate mineral complexes were successful in promoting the uniform growth of the pLys-CP.

Figure 7:
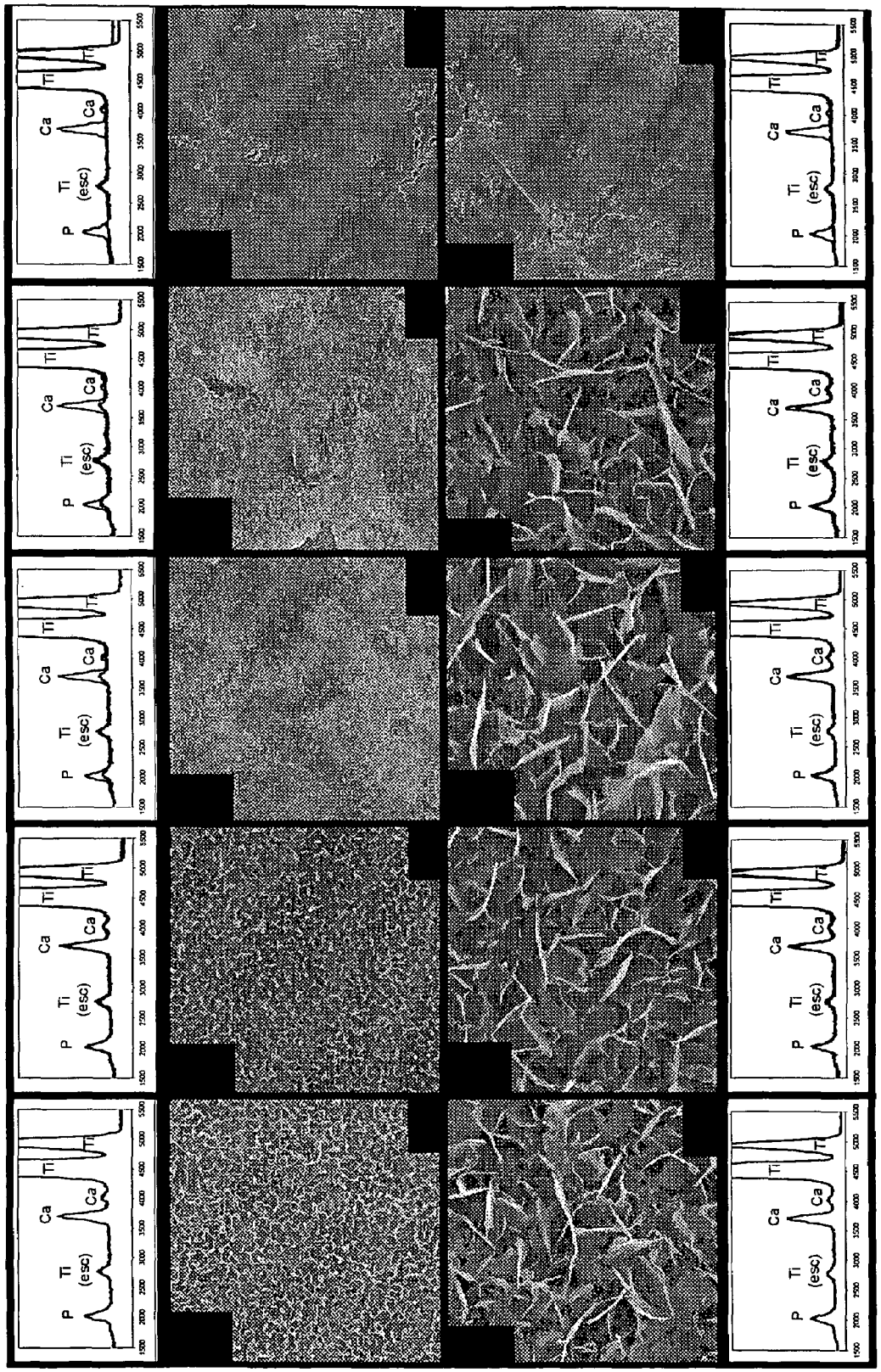
FIG. 7: Scanning electron micrograph digital images and corresponding EDS patterns showing different degradation behaviors of the OCP coating versus the pLys-CP coating. Scale bars are 1 micron. The x-axis on the EDS plots represents energy (eV) and EDS patterns have been normalized by the background intensity between 3000 and 3500 eV.

The pLys-CP coating was also found to be particularly susceptible to conditions of biologically relevant degradation. Table 6 summarizes these observations, while FIG. 7 illustrates the SEM micrographs with the corresponding EDS patterns to show the degradation effects on the coating.

TABLE 6

Coating Stability under Acidic and Enzymatic Degradation Conditions

| Degradation solution | OCP coating stable? | 1) pLys-OCP coating stable? |
|---|---|---|
| PH 7.4 buffer hanks balanced salt solution (HBSS) | yes | 2) yes |
| PH 7.4 buffer MEM-a culture medium with 10% fetal bovine serum | yes | 3) yes |
| PH 7.0 citrate buffer | yes | 4) no (seed layer stable) |
| PH 6.0 citrate buffer | no | 5) no |
| 0.2% trypsin in HBSS at pH 7.4 | yes | 6) no (seed layer stable) |
| 0.2% pronase in HBSS at pH 7.4 | yes | 7) no (seed layer stable) |

Tested over the course of 24 hours, both the OCP and pLys-CP coatings were found to be relatively stable in pH 7.4 buffered media. When the pH was reduced to 7, however, the OCP coating was largely stable, a slight drop in Ca and P EDS intensity illustrating very limited solubility. The textured pLys-CP coating was visibly dissolved, leaving behind what appear to be remnants of the inorganic pre-seed layer, evidenced by the texture seen in FIG. 7. The EDS analysis shows a substantial drop in the Ca and P peak intensities, but because of the residual inorganic seeds, stable at this pH, the peaks do not disappear altogether. Under slightly acidic conditions at pH 6, both coatings were fully dissolved. Micrographs of these substrates appear barren and the EDS scans show no evidence of calcium or phosphate. Treatment of the coatings with enzyme solutions of trypsin and pronase, buffered at pH 7.4, showed that the purely inorganic coating was stable, whereas the pLys-CP coating was again unstable, leaving behind only the inorganic preseed layer and small EDS peaks for Ca and P.

Figure 8:
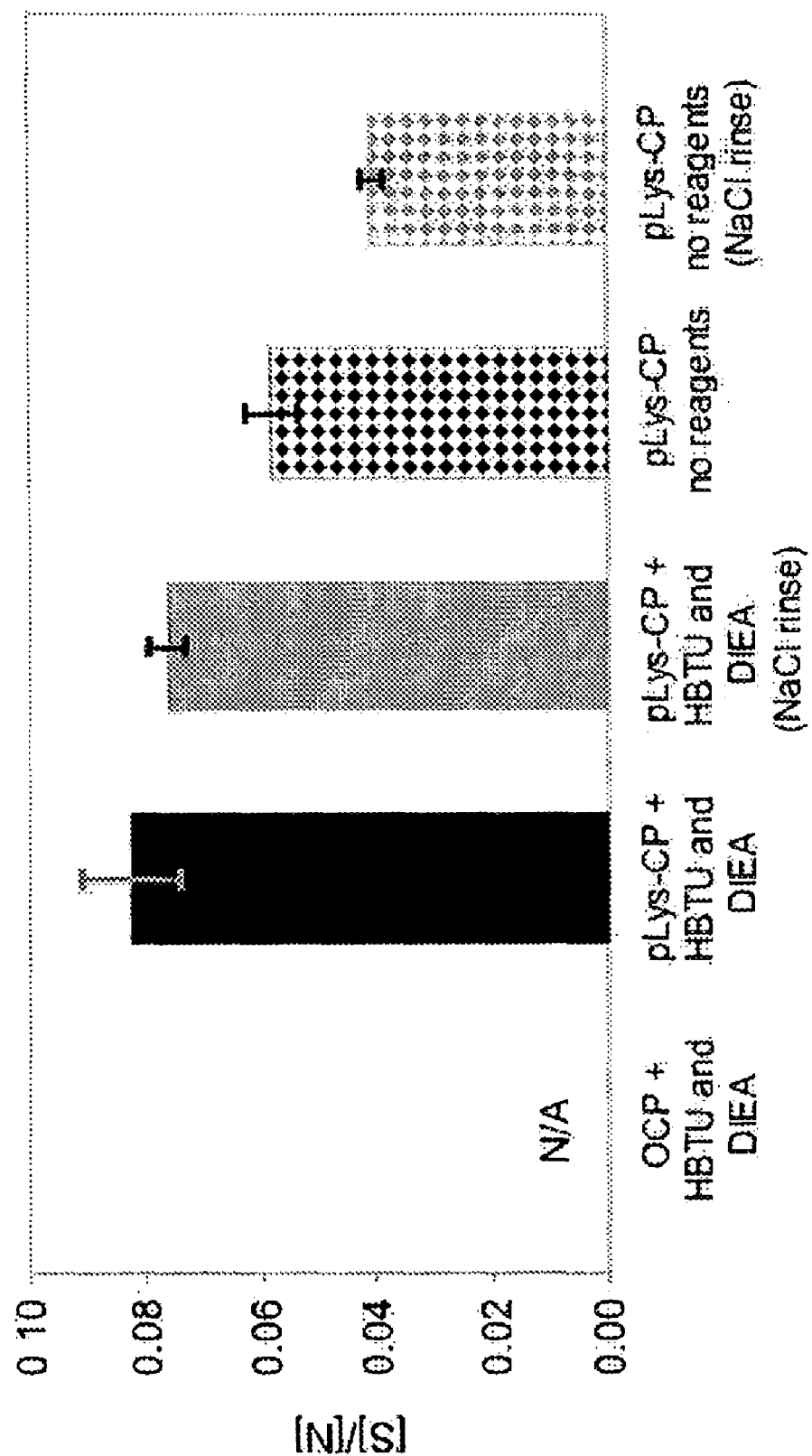
FIG. 8: S:N ratios determined by XPS illustrating binding affinity of cysteine to OCP and pLys-CP coatings. Neither sulfur nor nitrogen was substantially detected on OCP samples. Error bars represent ±1 standard deviation from duplicate measurements.

The incorporation of pLys into the Ca—P layer also introduced a valuable chemical tether for linking functional biomolecules to the coating. Poly(L-lysine)'s positively-charged free amine side chain may serve as a binding linker either through electrostatic interactions with the negatively-charged molecules, or through the formation of amide bonds between lysine's free amine and carboxylic acids on the target molecule. These binding schemes were demonstrated by attaching cysteine molecules to the pLys-CP coating. Cysteines bound to the surface are revealed by the appearance of a sulfur (is) binding energy peak at 164 eV in the XPS spectra of FIG. 8. Comparison of the S:N molar ratios for these spectra, shown in FIG. 8, provides a semiquantitative comparison of the sulfur content on the different samples. These data first illustrate that cysteine was bound only to pLys-CP, and that there was notably more cysteine present when HBTU and DIEA were added to the reaction, perhaps because of the increased bond stability of amide linkages formed. When these samples were rinsed in a saturated saline solution, the S:N ratio of samples treated in HBTU and DIEA remained statistically indistinguishable. Cysteines bound to the pLys-CP in the absence of HBTU and DIEA, were apparently displaced when washed with saturated saline, as evidenced by the substantial decrease in the S:N ratio.

The observations above describe a new calcium phosphate-organic composite coating on titanium surfaces. Collectively, the XRD, RFTIR, XPS, TGA, and elemental analyses illustrate that incorporation of pLys into this new coating produces a poorly crystalline, calcium deficient composite of octacalcium phosphate. Examination by SEM reveals the strong distortional influence of pLys on the formation of the OCP crystals. The resulting coating consists of irregular, nanoscale features reminiscent on the clean, sharp crystals formed in the purely inorganic OCP coating. The incorporation of the pLys into the mineral phase is illustrated by the disruption of the coating crystallinity seen by XRD and FTIR as well as by the coating's enzymatic disintegration. Were the polymer merely coated onto exterior surfaces of the small, modified crystals those crystals would largely be expected to persist, as in the inorganic control. Upon enzymatic degradation of the organic component in the pLys-CP coating, however, the pLys-modified coating disintegrates leaving behind only the inorganic seed crystals. This result strongly illustrates that the pLys is incorporated throughout the calcium phosphate structure. The covalent amide coupling of the biomolecules to the free amine tethers in the pLys-CP was illustrated in a very basic demonstration utilizing cysteine. Naturally, the presence of amide bonds throughout the lysine polymer of the pLys-CP coating confound the direct identification of an amide linkage between the cysteine and the pLys. This coupling, however, may be revealed through empirical deduction. When examined by XPS, cysteine's sulfur content made it a chemically unique marker for cysteines bound to a sample surface. The selective appearance of the XPS sulfur peak in the pLys-CP sample illustrate that the cysteines are interacting with the pLys component of the coating. This interaction may take two forms: electrostatic and covalent. The electrostatic binding of the material involves the attraction between the negatively-charged free acid of the cysteine and the positively-charged free amine on the pLys side chains. It is this electrostatic attraction that is likely to have bound cysteines to the pLys-CP in the absence of HBTU and DIEA. Rinsing of samples experiencing this interaction with saline resulted in the displacement cysteines with chloride ions, and a significant reduction in the amount of sulfur present on the sample. This displacement supports the electrostatic character of the bond. In contrast, when the cysteines were introduced to the free amines in the presence of amide-linking reagents HBTU and DIEA, the amide bond formed allowed the cysteines to persist on the pLys-CP surface. The dependence of this persistence on the presence of the amide coupling agents and the insusceptibility of the bond to electrostatic replacement strongly illustrate that the cysteines are covalently, amide-coupled to the pLys coating.

While not wishing to be bound by theory, the mechanism for the growth of the pLys-CP coating on the oxidized titanium surface involves several sequential steps. Nucleation of calcium phosphates on titanium surfaces is believed to be related to hydroxyl ions decorating the naturally forming titanium dioxide ($TiO_2$) surface at physiologic pH. The XPS data presented above show that during the preseeding stages $Ca^{2+}$ alone, but not $PO_4^{3-}$ alone, are measurably bound to the oxidized titanium surface. Simultaneous introduction of both $Ca^{2+}$ and $PO_4^{3-}$, however, results in the rapid formation of calcium phosphate complexes whose Ca:P ratio of 1.55 corresponding to amorphous calcium phosphate. These complexes are nucleated on the metal surface, likely via an initial interaction between calcium ions and hydroxyls decorating the oxide surface. Over time, these aggregates mature, reorganizing to incorporate added phosphate into their structure. After several hours these aggregates grow to become the mineral features (OCP) seen in FIG. 6, whose Ca:P ratio drops from 1.55 to 1.33. When poly(L-lysine) is present during these nucleation stages, however, the calcium phosphate is not able to successfully nucleate directly on the metal surface, probably due to interference in the calcium-hydroxyl interaction by the positively-charged side chains on the pLys. It has been shown that the positively charged pLys is readily bound to titanium's hydroxylated oxide surface. It is reasonable, then, to conclude that the pLys may block the necessary nucleating hydroxyls on the oxide surface. This phenomenon explains why the pLys-CP is unable to grown directly on the bare Ti surface. When the surface is decorated with calcium phosphate seeds, however, there are many more available nucleation sites present, and the pLys is unable to completely inhibit the continued growth of the mineral phase. It is clear that these calcium phosphate seeds promote the uniform growth of the pLys-CP coating. Though the mechanism for this growth is not obvious, it is conceivable that the new mineral grows as part of a disrupted epitaxy. New mineral nucleates and grows out of the existing calcium and phosphate on the surface, the pLys distorting newly forming OCP crystals as it is incorporated into the coating.

The calcium deficiency revealed in the XPS Ca/P ratio of this pLys-CP coating illustrates that divalent calcium ions are excluded from newly forming crystals by positively charged polymer side chains, either through charge repulsion or crystal site obstruction. In addition, there may have been some preferential interaction between the positively-charged pLys side chains and the negatively-charged phosphate ions. This scenario may help to explain the early onset of mineral formation in the pH trace for pLys-CP. In the early stages of mineralization, such phosphate affinity would create locally phosphate-rich Ca—P aggregates, which could, in turn, trigger the early onset of crystallization. This sort of phosphate-binding affinity would certainly disrupt proper crystal formation and produce phosphate rich, or calcium deficient, OCP crystals. Either of the two interactions between the pLys and the constituents of the Ca—P mineral could be responsible for the formation of the distorted structures seen in the pLys-CP coating.

The pLys-CP coating of the present invention offers a number of advantages over other calcium phosphate coatings, particularly from a clinical standpoint. The solution phase growth of the coating make its application accessible to all surface types, including porous surfaces, where currently accepted methods of calcium phosphate growth such as a plasma spraying may not be feasible. The pLys-CP coating has very high surface area and feature sizes reasonably consistent with the apatite crystal found in natural bone. This nanoscale texture and high surface area are furthermore characteristics which would be expected to promote initial cell adhesion, spreading, and proliferation, important to forming a stable tissue implant interface. As an accent to this effect, poly(L-lysine) has been well-established as a cell adhesion promoter, and its significant presence in pLys-CP is expected to further enhance cellular adhesion to the implant coating. This pLys component not only adds bioactivity as a cellular adhesive, but it also provides chemically functional tethers for attachment of other bioactive agents. Such an approach could be easily adapted to attach biorelevant peptides, such as arg-gly-asp (RGD), therapeutic molecules such as bone morphogenetic proteins or anti-inflammatory drugs to the implant coating. Also advantageously, the coating is also susceptible to biological degradation, by both pH and enzymatically-mediated mechanisms, two primary mechanisms for osteoclastic resorption in natural bone. Coating dissolution may accelerate de novo bone formation and enhance implant interfacial strength. This coating has been engineered to act as an osteoconductive surface, which may be readily recycled, acting as a pool of building blocks for new biogenic mineralization.

The use of a pre-seeded layer may be used to facilitate the growth of other organically-modified materials onto a surface. In the present invention organic molecules introduced to mineral coatings exert an influence on properties such as coating morphology and degradation. The organic influence on degradation could be utilized to engineer the time-dependent release of therapeutic molecules incorporated into the mineral or chemically attached to pLys. Alternative organic constituents might also be utilized to vary morphological influences or rates of material degradation. It is clear that this approach to surface coatings offers a number of broad and varied potential applications with the capability to substantially influence orthopedic and dental implant coatings.

EXAMPLE 5

This example illustrate chemical attachment of peptide amphiphile nanofibers to a pLys-OCP coating on a titanium substrate: Peptide amphiphile nanofiber to pLys-OCP is based on a standard amide coupling reaction, applied to a pre-assembled, cross-linked peptide nanofiber. Specifically, a dilute solution of peptide amphiphile molecules, containing carboxylic acids at near the C-terminus of the peptide segments and at least 2 cysteines in the structural peptide segment (see FIG. 9 and Hartgerink et al., PNAS, vol 99, pp 5133-5138, 2002 and reference therein for methods and materials for making such peptides which are incorporated herein by reference in their entirety), maintained in a solution of a mild reducing agent (such as dithiolthreitol (DTT)), is self-assembled in acidic conditions to form peptide nanofibers. These nanofibers may be crosslinked by the addition of a non-destructive oxidizer, such as iodine, forming stable intermolecular, intrafiber disulfide bonds. The resulting suspension of these fibers is dialyzed against water to remove all reducing or oxidizing agents (such as DTT and iodine). This dialyzed suspension of cross-linked fibers is then lyophilized and the dried fibers are re-suspended by vigorous agitation and ultrasonication in a peptide-solublizing polar organic solvent, such as N,N-dimethylformarmide (DMF) or NMP. The covalent cross-linking of the fibers stabilizes them in the non-aqueous environment.

To the suspension of cross-linked nanofibers in N,N-dimethylformamide (DMF), solutions of O-Benzotriazole-N,N, N',N'-tetramethyl-uronium-hexafluoro-phosphate (HBTU) and diisopropylethylamine (DIEA) were added to provide slightly less than about 1 equivalent (0.95) of HBTU for every free carboxylic acid on the nanofibers and approximately 6 equivalents of DIEA for every estimated free amine exposed on the lysine-modified calcium phosphate coating titanium surface. This solution was allowed to incubate for several minutes before exposure to the coated titanium surface. Once introduced, the calcium-phosphate coated titanium is shaken for least 1 hour in the nanofiber reaction solution before thorough rinsing with water and drying at room temperature. FIG. 10A is a scanning electron micrograph showing bundles of fibers attached to the textured coating surface. FIG. 10B is a higher magnification image revealing layers of individual fibers coating the textured structures of the calcium phosphate coating.

Preliminary in vitro experiments with preosteoblastic mouse calvaria cells have demonstrated the biocompatibility of the pLys-CP coating. Titanium foil samples were coated as described above with inorganic OCP as well as poly(L-lysine)-modified calcium phosphate. Substrates were autoclaved at 115° C. for 30 minutes before placing them in sterile, tissue-culture polystyrene 24-well plates.

Immortalized mouse calvarial preosteoblasts (MC3T3-E1), were cultured in T-75 flasks in MEM-α containing 10% fetal bovine serum (Hyclone, Logan Utah) and 1% penicillin/streptomycin. Media was supplemented with 30 mM P-glycerolphosphate and 50 µg/mL ascorbic acid. At approximately 90% confluence, cells were removed from the T-flask by treatment with 0.25% trypsin, 1 mM ethylenediaminetetraacetic acid (EDTA). Trypsinization was stopped by addition of culture medium and cells were pelleted by centrifugation. Cells were resuspended in medium and plated onto coated foil substrates at a density of $5 \times 10^3$ cells/cm$^2$. Fresh medium was added to a total volume of 1 mL/sample. Cells were cultured for 7 days in an incubator at 37° C. and 5% $CO_2$, changing medium every 3 days.

Samples were removed from their culture wells at intervals of 1 day, 4 days, and 7 days and were fixed in 2.5% glutaraldehyde in 0.1M sodium cacodylate buffer. After thorough rinsing in sodium cacodylate buffer, samples were post-fixed for 1 hour in 1% osmium tetroxide in 0.1M sodium cacodylate buffer for 1 hour. Fixed samples were then dehydrated in graded ethanol solutions (50%, 70%, 80%, 90%, 95%, 100%) and critical point dried by ethanol-$CO_2$ exchange. Dried samples were sputter-coated with 3 nm of gold-palladium and examined by scanning electron microscopy.

Results of in vitro study show that cells cultured on these substrates remain viable, spreading and proliferating to form confluent cell layers on the pLys-CP coating over the course of 7 days. FIG. 11A shows individual cells spreading on the coating after 1 day, while FIG. 11B shows multiple cells spreading on the surface after 4 days. In FIG. 11C, a confluent cell layer formed by proliferating cells after 7 days is visible. This experiment demonstrates that the material is non-toxic and does promote cellular adhesion and spreading, behaviors critical to normal osteoblastic function.

The methods and materials of embodiments of the present invention would be most readily suited to coating titanium-based orthopedic implant materials with an osteogenic calcium-phosphate coating. The detailed examples described above illustrate that this coating material consists is highly textured and may completely coat surfaces exposed to the reaction solutions. Such a coating may have a favorable influence on cellular attachment, spreading, proliferation, and possibly osteoblastic differentiation. Such influence could offer significant improvements in tissue integration with an implant surface. The incorporation of the organic macromolecules within the coating adds chemical functionality which could be used to bind biologically functional materials to the coating surface, including peptidic micelles, individual peptide sequences, or other therapeutic molecules such as drugs or growth factors. The low crystallinity of the material and the integration of enzyme-vulnerable macromolecules may make the material a useful system for slow release of these macromolecules. Similarly, the potential degradability of this coating makes is a ready source of calcium and phosphate material for subsequent biological mineralization of de novo bone matrix.

Although the present invention has been described in considerable detail with reference to certain preferred embodiments thereof, other versions are possible. For example therapeutic macromolecules could be incorporated directly into the mineral phase in place of the polyamine. Substitution of the polyamine like poly(L-lysine) need not be limited to therapeutic molecules, but other amino acids, possible containing free acids (like glutamic acid or aspartic acid) could be incorporated into the mineral phase. These molecules would present different chemical functionalities on the material surface, and may even change the way the inorganic material is modified. Furthermore, variations of the calcium-phosphate ratios and concentrations, different phases of calcium phosphate, such as hydroxyapatite, tricalcium phosphate, brushite, or monetite, could be coated on the substrate surface using the methods herein described in order to create coatings with differing chemistries, textures, or materials properties. Therefore the spirit and scope of the appended claims should not be limited to the description and the preferred versions contain within this specification.

We claim:

1. A nanotextured biocompatible composite, comprising a biocompatible substrate and a mineral phase on said substrate comprising a calcium phosphate component, nanofibers of peptide amphiphiles, and poly(L-lysine), wherein said nanofibers are coupled to the poly(L-lysine) on said calcium phosphate component.

2. The composite of claim 1 wherein the calcium content of said mineral phase is less than stoichiometric, and said poly(L-lysine) is incorporated within said calcium phosphate.

3. The composite of claim 1 wherein said mineral phase is reactive with at least one of an acid and degradative enzyme.

4. The composite of claim 1 wherein at least one of said peptide amphiphiles comprises a carboxy functionality.

5. The composite of claim 4 wherein at least one of said peptide amphiphiles comprises the sequence, RGD.

6. The composite of claim 4 further comprising a mammalian preosteoblast cell culture.

7. The composite of claim 1 wherein said substrate comprises titanium.

* * * * *

UNITED STATES PATENT AND TRADEMARK OFFICE
CERTIFICATE OF CORRECTION

PATENT NO. : 7,390,526 B2
APPLICATION NO. : 10/777030
DATED : June 24, 2008
INVENTOR(S) : Samuel I. Stupp et al.

It is certified that error appears in the above-identified patent and that said Letters Patent is hereby corrected as shown below:

On the Title Pg. Item (56) In the "Other Publications" section, please insert the following reference:
--Richardson, P. M., U. M. McGuinness, and A. J. Aguayo. March 20, 1980. "Axons from CNS Neurones Regenerate into PNS Grafts." Nature. Vol. 284, pp. 264-265.--

In column 8, line 38, please change "seine" to --serine--.

In column 26, lines 40-41, please change "N,N-dimethylformamide" to --N,N-dimethylformarnide--.

In column 30, line 11, before the word "bands" there is a superscript number "3". Please add a superscript minus (-) symbol after the number 3.

In column 30, Table 4, in the last column of the table and the row that begins with "Preseed 2 hours", please change "0.30" to --1.30--.

In column 32, line 21, please change "(is)" to --(1s)--.

In column 35, lines 41-42, please change the "P" in "P-glycerolphosphate" to an uppercase beta symbol.

Signed and Sealed this

Fourteenth Day of April, 2009

JOHN DOLL
*Acting Director of the United States Patent and Trademark Office*